(12) United States Patent
Baker et al.

(10) Patent No.: US 8,168,614 B2
(45) Date of Patent: May 1, 2012

(54) BORON-CONTAINING SMALL MOLECULES AS ANTI-INFLAMMATORY AGENTS

(75) Inventors: Stephen J. Baker, Mountain View, CA (US); Virginia Sanders, San Francisco, CA (US); Tsutomu Akama, Sunnyvale, CA (US); Carolyn Bellinger-Kawahara, Redwood City, CA (US); Yvonne Freund, Los Altos, CA (US); Kirk R. Maples, San Jose, CA (US); Jacob J. Plattner, Berkeley, CA (US); Yong-Kang Zhang, San Jose, CA (US); Huchen Zhou, Shanghai (CN); Vincent S. Hernandez, Watsonville, CA (US)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 1069 days.

(21) Appl. No.: 11/676,120

(22) Filed: Feb. 16, 2007

(65) Prior Publication Data

US 2007/0293457 A1    Dec. 20, 2007

Related U.S. Application Data

(60) Provisional application No. 60/774,532, filed on Feb. 16, 2006, provisional application No. 60/823,888, filed on Aug. 29, 2006.

(51) Int. Cl.
*A61K 31/69* (2006.01)
(52) U.S. Cl. .......................................... 514/64
(58) Field of Classification Search .............. 514/64
See application file for complete search history.

(56) References Cited

U.S. PATENT DOCUMENTS

| | | | |
|---|---|---|---|
| 2,260,336 A | 10/1941 | Prescott et al. | |
| 3,873,279 A | 3/1975 | Singer | |
| 4,602,011 A | 7/1986 | West et al. | |
| 4,716,035 A | 12/1987 | Sampathkamar | |
| 4,766,113 A | 8/1988 | West et al. | |
| 4,894,220 A | 1/1990 | Nabi et al. | |
| 5,348,947 A | 9/1994 | Patel et al. | |
| 5,348,948 A | 9/1994 | Patel et al. | |
| 5,591,731 A | 1/1997 | Kennedy et al. | |
| 5,668,258 A | 9/1997 | Stolowitz | |
| 5,688,928 A | 11/1997 | Stolowitz | |
| 5,831,045 A | 11/1998 | Stolowitz et al. | |
| 5,880,188 A * | 3/1999 | Austin et al. .................. | 524/109 |
| 5,962,498 A | 10/1999 | Driedger et al. | |
| 6,083,903 A | 7/2000 | Adams et al. | |
| 6,306,628 B1 | 10/2001 | Rothschild et al. | |
| 6,369,098 B1 | 4/2002 | Pershadsingh et al. | |
| 6,521,619 B2 | 2/2003 | Link et al. | |
| 6,800,645 B1 | 10/2004 | Cox et al. | |
| 6,855,848 B2 | 2/2005 | Scherer et al. | |
| 7,217,701 B2 | 5/2007 | Mikoshiba et al. | |
| 7,390,806 B2 | 6/2008 | Lee et al. | |
| 7,393,856 B2 | 7/2008 | Bellinger-Kawahara et al. | |
| 7,465,836 B2 | 12/2008 | Lee et al. | |
| 7,582,621 B2 | 9/2009 | Baker et al. | |
| 7,652,000 B2 | 1/2010 | Perry et al. | |
| 7,767,657 B2 | 8/2010 | Baker et al. | |
| 7,816,344 B2 | 10/2010 | Baker et al. | |
| 7,888,356 B2 | 2/2011 | Lee et al. | |
| 8,039,451 B2 | 10/2011 | Baker et al. | |
| 2002/0028831 A1 | 3/2002 | Manley | |
| 2002/0161230 A1 | 10/2002 | Meudt et al. | |
| 2003/0032673 A1 | 2/2003 | Nagy | |
| 2004/0077601 A1 | 4/2004 | Adams et al. | |
| 2004/0224923 A1 | 11/2004 | Lee et al. | |
| 2005/0054644 A1 | 3/2005 | Lee et al. | |
| 2005/0125852 A1 | 6/2005 | Caenepeel et al. | |
| 2005/0239170 A1 | 10/2005 | Hedley et al. | |
| 2006/0009386 A1 | 1/2006 | Stossel et al. | |
| 2006/0222671 A1 | 10/2006 | Weidner | |
| 2006/0234981 A1 | 10/2006 | Baker et al. | |
| 2007/0155699 A1 | 7/2007 | Baker et al. | |
| 2007/0286822 A1 | 12/2007 | Sanders et al. | |
| 2007/0293457 A1 | 12/2007 | Baker et al. | |
| 2009/0227541 A1 | 9/2009 | Baker et al. | |
| 2010/0256092 A1 | 10/2010 | Xia et al. | |
| 2010/0267981 A1 | 10/2010 | Baker et al. | |

FOREIGN PATENT DOCUMENTS

| | | |
|---|---|---|
| EP | 0969531 | 1/2000 |
| EP | 1155698 A1 | 11/2001 |
| EP | 1 444 981 A1 | 8/2004 |
| WO | WO 9533754 | 5/1995 |
| WO | WO 9622023 A1 | 7/1996 |
| WO | WO 9812206 A1 | 3/1998 |
| WO | WO 0044387 A1 | 8/2000 |
| WO | WO 0075142 A2 | 12/2000 |
| WO | WO 0149303 A1 | 7/2001 |
| WO | WO 0244184 | 6/2002 |
| WO | WO 03033002 A1 | 4/2003 |
| WO | WO 03059916 A2 | 7/2003 |
| WO | WO 2004056322 A2 | 7/2004 |
| WO | WO 2005/013892 A2 * | 2/2005 |
| WO | WO 2005/013892 A3 | 2/2005 |
| WO | WO 2006007384 | 1/2006 |
| WO | WO 2006062731 A1 | 6/2006 |
| WO | WO 2006079843 A1 | 8/2006 |
| WO | WO 2006089067 A2 | 8/2006 |
| WO | WO 2007022437 A2 | 2/2007 |
| WO | WO 2007078340 A2 | 7/2007 |
| WO | WO 2007095638 A2 | 8/2007 |
| WO | WO 2007146965 A2 | 12/2007 |
| WO | WO 2008157726 A1 | 12/2008 |
| WO | WO 2009111676 A2 | 9/2009 |
| WO | WO 2009014309 A2 | 11/2009 |
| WO | WO 2010028005 A1 | 3/2010 |
| WO | WO 2010045503 A | 4/2010 |
| WO | WO 2010045505 A1 | 4/2010 |

OTHER PUBLICATIONS

Patani, George, et al , "Bioterrorism: A Rational Approach to Drug Design," Chem. Rev. vol. 96, pp. 3147-3176 (1996).*

(Continued)

*Primary Examiner* — Raymond Henley, III
(74) *Attorney, Agent, or Firm* — Morgan, Lewis & Bockius LLP

(57) ABSTRACT

Methods of treating anti-inflammatory conditions through the use of boron-containing small molecules are disclosed.

36 Claims, 21 Drawing Sheets

OTHER PUBLICATIONS

McMillin, David, et al, "Systemic Aspects of Psoriasis: An Integrative Model Based on Intestinal Etiology," Int. Med. vol. 2, Issue 2/3 (1999).*

Bessis, N., "Gene Therapy for Rheumatoid Arthritis," *J. Gene Med*, 4:581-591 (2002).

Zhou, Huchen, et al., "Hemodextrin: a Self-assembled Cyclodextrin-Porphyrin Construct That Binds Dioxygen," *Biophysical Chemistry*, 105:639-648 (2003).

Zhou, Huchen, et al., "Structure-activity Studies on a Library of Potent Calix[4]arene-based PDGF Antagonists that Inhibit PDGF-stimulated PDGFR Tyrosine Phosphorylation," *Org. Biomol. Chem.*, 4:2376-2386 (2006).

Zhou, Huchen, et al., "Pattern Recognition of Proteins Based on an Array of Functionalized Porphyrins," *J. Am. Chem. Soc.*, 128:2421-2425 (2006).

Sudaxshina Murdan, "Drug Delivery to the Nail Following Topical Application," *International Journal of Pharmaceutics*, 236:1-26 (2002).

S. J. Baker, et al., "Progress on New Therapeutics for Fungal Nail Infections," *Annual Reports in Medicinal Chemistry*, 40:323-335 (2005).

Austin, et al., "Oxaboroles and Salts and their Use of Biocides for Plastics", CAS, vol. 124, pp. 234-024, (1996).

Bailey, et al., "Boron-Containing Antibacterial Agents: Effects on Growth and Morphology of Bacteria Under Various Culture Conditions," Antimicrobial Agents and Chemotherapy, 17(04):549-553, (Apr. 1980).

Baker, et al., "Discovery of New Boron-Containing Antifungal Agent, 5-Fluoro-1,3-dihydro-1-hydroxy-2, 1-benzoxaborole (AN2690) for Potential Treatment of Onychomoycosis", Journal of Medicinal Chemistry, vol. 49, No. 15; pp. 4447-4450, (Jul. 27, 2006).

Brown, et al., "Chiral Synthesis Via Organoboranes. 35. Simple Procedures for the Efficient Recycling of the Terpenyl Chiral Auxiliaries and Convenient Isolation of the Homoallylic Alcohols in Asymmetric Allyl- and Crotylboration of Aldehydes," J. Org. Chem., vol. 57, No. 24; pp. 6608-6614, (1992).

Cairns, et al., "Derivatives of 1,4-Xylene-2,5-diboronic acid and 1,4-xylene-2-boronic acid", J. Org. Chem. vol. 29; pp. 2810-2812, (1964).

Chander, et al. "Prevalence of Fungal Corneal Ulcers in Northern India", Infections, vol. 22, No. 3; pp. 207-209, (1994).

Chemical Abstracts Registry No. 845302-09-2, Entered STN Mar. 11, 2005.

Cui, et al., "Organoboron Compounds with an 8-Hydroxyquinolato Chelate and Its Derivatives: Substituent Effects on Structures and Luminescence," Inorganic Chemistry, vol. 44, No. 03; pp. 601-609, (Feb. 7, 2005).

Dale, et al., "Substituted Styrenes VIII Syntheses and some Reactions of the Vinylbenzeneboronic Acids" J. Org. Chem. vol. 27; pp. 2598-2603, (1962).

Denis, "Pharmacology 1104 Lecture: Drug Classifications & Characteristics of Antimicrobials" (2003).

Farfan, et al., "Through-Bond Modulation on N-B Ring Formation Shown by NMR and X-Ray Diffraction Studies of Borate Derivatives of Pyridyl Alcohols," J. Chem. Soc. Perkin Trans., vol. 2; pp. 527-532 (1992).

Ferrer, Targeting Aminocytl-tRNA Synthetases for the Treatment of Fungal Infections, Drug News Perspective, vol. 19, No. 6; pp. 347-348, (Jul./Aug. 2006).

Fungicide: Definition from Answer.com, (1998).

Grassberger, et al., "Degradation of 1,2-dihydro-1-hydroxy-2-(organosulfonyl)2,3,1-benzodiasaborines and -thieno[3,2-d][1,,3]diazaborines in Alkaline Aqueous Solutions", Liebigs Annalen Der Chemie, vol. 4; pp. 683-688, (1985).

Guo-Zheng, et al., "Single Site Transarylation of 2,2'-Dimetalized-1,1'-Binaphthyl to Aminocloroborates and Synthesis of 2-Binaphthyl Boron Compounds," Youji Huaxue/Organic Chemistry, Science Press, vol. 16, No. 02; pp. 139-144, (1996) (English Abstract).

Haynes, et al., "Arylboronic Acids VIII. Reactions of boronphthalide" J. Org. Chem. vol. 29, No. 11; pp. 3229-3233, (1964).

Hauck, et al., "Preparation and Anticonvulsant Activity of Some Arydialkkylsuccinimides" Research Lab of Parke Davis Co. (1967).

He, et al., "Small-Molecule Inhibition of TNF-alpha", Science, vol. 310, No. 5750; pp. 1022-1025, (Nov. 11, 2005).

Lampe, et al., "Synthesis and Protien Kinase Inhibitory Activity of Balanol Analogues with Modified Benzophenone Subunits", J. Med. Chem., vol. 45; pp. 2624-2643, (2002).

Lennarz, et al., "Arylboronic Acids. IV. Reactions of Boronophthalide" J. Am. Chem. Soc. vol. 82; pp. 2172-2175, (1960).

Li, et al., "An Improved Protocol for Preparation of 3-Pyridyl- and Some Arylboronic Acids", J. Org. Chem., vol. 67; pp. 5394-5397, (2002).

Koster, et al., "Cyclisierugen von Bor-Stickstoff-Verbindugen in der Hietz" Liebigs Ann. Chem., vol. 720; pp. 23-31, (1968).

Koster, et al., "Boron Compounds. XXXIX. Alkenoxy(diorgany)boranes Substituted at the Alkeonxy Group from 2-methylacrolein and triorganylboranes," Justus Liebigs Annalen Der Chemie, No. 06; pp. 1116-1134, (1976).

Moeder, et al., "Kinetic Analysis of the Asymmetric Amplification exhibited by B-chlorodiisopinocampheylborane," Journal of Physical Organic Chemistry, vol. 17, No. 4; pp. 317-324, (Apr. 2004).

Morissette, et al., "High-throughput Crystallization: Polymorphs, Salts, Co-Crystals and Solvates of Pharmaceutical Solids", Advanced Drug Delivery Reviews, vol. 56; pp. 273-300, (2004).

Qin, et al., "Luminescent Organoboron Quinolate Polymers," Journal of the American Chemical Society, vol. 126, No. 22; pp. 7015-7018, (Jun. 9, 2004).

Rock, et al., "An Antifungal Agents Inhibits Aminoacyl-tRNA Synthetase by Trapping tRNA in the Editing Site", Science, vol. 316, No. 5832; pp. 1759-1761, (Jun. 22, 2007).

Snyder, et al. "Common Bacteria Whose Susceptibility to Antimicrobials in no longer Predictable" J. Med. Liban, vol. 48 No. 4; pp. 208-214, (2000).

Sugar, et al., "Comparison of Three Methods of Antifungal Susceptibility Testing with the Proposed NCCLS Stardard Broth Macrodilution Assay: Lack of Effect of Phenol Red" Diagn. Microbiol. Infect. Dis. vol. 21; pp. 129-133, (1995).

Tabuchi, et al., "Anticoccidial Activity of some Azacyclo Organoborinates," Heterocycles, vol. 60, No. 01; pp. 177-182, (2003).

Toporcer, et al., "Preparation and Properties of some Tetracoordinate Boron Compounds. The Pseudo-metal Ion Concept," Inorganic Chemistry, vol. 4, No. 11; pp. 649-1655, (Nov. 1965).

Trujillo, et al., "X-Ray Crystallographic Study of Boroxazolidones, Obtained from L-ornithine, L-methionine, Kainic acid and 2,6-pyridinedicarboxylic acid", Journal of Organometallic Chemistry, vol. 571; pp. 21-29, (1998).

Tschampel, et al., "Arylboronic Acids. VII. Some Reactions to o-Formybenzeneboronic Acids", J. Org. Chem. vol. 29, No. 8; pp. 2168-2172, (1964).

Turner, et al., Current Pharmaceutical Design, vol. 2; pp. 209-224 (1996).

Vippagunta, "Crystalline Solids", Advanced Drug Delivery Reviews, vol. 48; pp. 3-26, (2001).

Wang, et al., "Expression, Purification and Characterization of Human cAMP-Specific Phosphodiesterase (PDE4) Subtypes A, B, C, and D", Biochemical and Biophysical Research Communications, vol. 234; pp. 320-324, (1997).

Ye, et al., "Convenient and Versatile Syntheis of formyl-substituted Benzoxaboroles", Tetrahedron, vol. 65; pp. 8738-8744, (2009).

Zhdankin, et al., "Synthesis and Structure of Benzoboroxoles: Novel Organboron Heterocycles," Tetrahedron Letters, vol. 40; pp. 6705-6708, (1999).

Zixing, et al., "Synthesis of Aromatic Nitrogen-containing Heterocyclic Derivatives of Asymmetric Diarylborinic Acids," Wuhan Daxue Xuebo-Wuhan University Journal, vol. 3; pp. 67-71, (1990), (English Abstract).

Alley, et al., "Recent Progress on Topical Therapy of Onychomycosis", Expert Opinion Investigate Drugs(Feb. 2007) 16(2): 157-67.

Baker, et al., "Discovery of a New Boron-Containing Antifungal Agent, 5-Fluoro-1,3-dihydro-1-hydroxy-2,1-benzoxaborole (AN2690), for Potential Treatment of Onychomycosis", Journal of Medicinal Chemistry, (2006): 49(16) 4447-4450.

Baker, et al., "Identification of a Novel Boron-Containing Antibacterial Agent (AN0128) with Anti-inflammatory activity, for the Potential Treatment of Cutaneous Diseases", Bioorganic & Medicinal Chemistry Letters (2006) 16(23): 5963-5967.

Baker, et al., "Synthesis of Isotopically labelled (3-$^{14}$C)- and (3,3-$^{2}$H$_2$)-5-fluoro-1,3-dihydro-1-hydroxy-2,1-benzoxaborole (AN2690), a new antifugal agent for the potential treatment of onychomycosis", J. Label Compd Radiopharm, (2007) 50:245-250.

Hui, et al., "In Vitro Penetration of a Novel Oxaborole Antifungal (AN2690) into the Human Nail Plate", Journal of Pharmaceutical Sciences (2007) 96(10): 2622-2631.

Rock, et al., "An Antifungal Agent Inhibits an Aminoacyl-tRNA Synthetase by Trapping tRNA in the Editing Site", Science, (Jun. 22, 2007) 316:1759-1761.

"Preclinical Toxicology of AN2728, a Novel Borinic Acid Ester with Anti-Inflammatory Activity", American Academy of Dermatology, 65th Annual Meeting, Washington, DC, Feb. 2-6, 2007.

"AN0128 Inhibits Pro-Inflammatory Cytokin Production in a Macrophae Cell Line by Inhibiting the P38 MAP Kinase Signal Transduction Pathway" American Academy of Dermatology, 65th Annual Meeting, Washington, DC, Feb. 2-6, 2007.

"AN2728, a Novel Oxaborole with Broad-Spectrum In Vitro Anti-Inflammatory Activity", American Academy of Dermatology, 65th Annual Meeting, Washington, DC, Feb. 2-6, 2007.

"A Randomized, Double-Blind, Vehicle-Controlled, Multi-Center Study to Evaluate the Safety and Efficacy of Topically Applied AN0128 1% Cream for the Treatment of Mild to Moderate Atopic Dermatitis" American Academy of Dermatology, 65th Annual Meeting, Washington, DC, Feb. 2-6, 2007.

"In Vitro Nail Penetration of AN2690, Effect of Vehicle and Co-Efficient of Efficacy", American Academy of Dermatology, 65th Annual Meeting, Washington, DC, Feb. 2-6, 2007.

"Interim Results of a Multi-Center Study to Evaluate the Safety and Efficacy of Topically Applied AN2690 5.0% and 7.5% Solutions for the Treatment of Onychomycosis of the Great Toenail", American Academy of Dermatology, 65th Annual Meeting, Washington, DC, Feb. 2-6, 2007.

"In vivo Nail Residence Time of AN2690, a Novel Broad-Spectrum Antifungal Agent in Development for the Topical Treatment of Onychomycosis", American Academy of Dermatology, 65th Annual Meeting, Washington, DC, Feb. 2-6, 2007.

"An Open-Label, Multi-dose Study of Absorption and Systemic Pharmacokinetics of AN2690 Applied as a 7.5% Solution to All Toenails of Adult Patients with Moderate to Severe Onychomycosis", American Academy of Dermatology, 65th Annual Meeting, Washington, DC, Feb. 2-6, 2007.

"Medicinal Chemistry Development of AN2728, A Novel Oxaborole in Development for the Topical Treatment of Psoriasis", American Academy of Dermatology, 65th Annual Meeting, Washington, DC, Feb. 2-6, 2007.

"Skin Penetration and Anti-Inflammatory Activity of AN2728, a Novel Oxaborole", American Academy of Dermatology, 65th Annual Meeting, Washington, DC, Feb. 2-6, 2007.

"Nail Penetration and Nail Concentration of AN2690, a Novel Broad-Spectrum Antifungal Agent in Development for the Topical Treatment of Onychomycosis", Scientific Presentation at the American Associate of Pharmaceutical Scientist, Annual Meeting, San Antonio, TX, Oct. 29-Nov. 2, 2006.

"New AN0128 Formulations Improve In Vitro Skin Penetration and In Vivo Efficacy" European Society for Dermatological Research, 36th Annual Meeting, Paris, France, Sep. 7-9, 2006.

"AN0128 Inhibits Pro-Inflammatory Cytokine Production in a Macrophase Cell Line by Inhibiting the p38 MAP Kinase Signal Transduction Pathway" European Society for Dermatological Research, 36th Annual Meeting, Paris, France, Sep. 7-9, 2006.

"A Randomized, Double-Blind, Vehicle-Controlled, Multicenter Study to Evaluate the Safety and Efficacy of Topically Applied AN0128 1% Cream for the Treatment of Mild to Moderate Atopic Dermatitis" European Society for Dermatological Research, 36th Annual Meeting, Paris, France, Sep. 7-9, 2006.

"AN0128, A Novel Borinic Acid Ester with In Vitro and In Vivo Anti-Inflammatory Activity", American Academy of Dermatology, 64th Annual Meeting, San Francisco, CA, Mar. 3-7, 2006.

"Preclinical Toxicology of AN0128, a Novel Borinic Acid Ester with Combined Antimicrobial and Anti-Inflammatory Activity" American Academy of Dermatology, 64th Annual Meeting, San Francisco, CA, Mar. 3-7, 2006.

"Clinical Safety of AN0128, a Novel Borinic Ester" American Academy of Dermatology, 64th Annual Meeting, San Francisco, CA, Mar. 3-7, 2006.

* cited by examiner

| Structure | % Inhibition | | | |
|---|---|---|---|---|
| | TNF-a (10uM) | IL-1b (10uM) | IFN-g (10 uM) | IL-4 (10uM) |
| 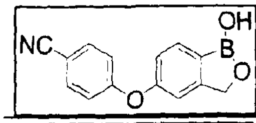 | 100 | 67 | 100 | 76 |
| 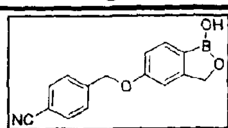 | 91 | 25 | 94 | 59 |
| 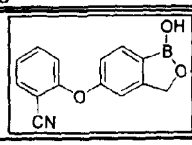 | 86.5 | 34.9 | 95.2 | 59.7 |
| 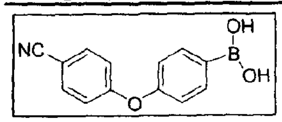 | 60 | 57.8 | 93 | 45 |
| 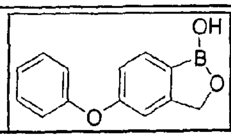 | 52 | | | |
| 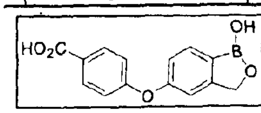 | 51 | 33 | 43 | 3 |
| 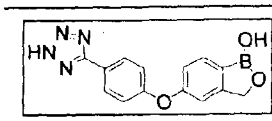 | 50.8 | -43.8 | 55.9 | -1 |
| 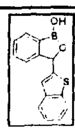 | 37.1 | -31.3 | 44.2 | 22.1 |
| 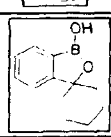 | 35 | -19.3 | 41 | -0.7 |
| 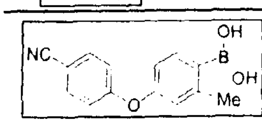 | 29 | 42 | 55 | 10 |
| 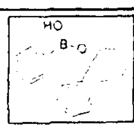 | 17.9 | -4.9 | 56.1 | 41.7 |

| Structure | | | | |
|---|---|---|---|---|
| 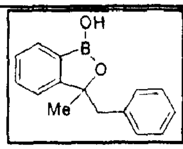 | 17.1 | -28.3 | 2.6 | -14.2 |
| 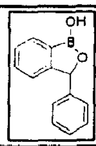 | 16.8 | 8.1 | 11 | -4.4 |
| 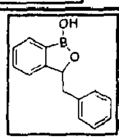 | 15.2 | -29.2 | 12 | 13.3 |
| 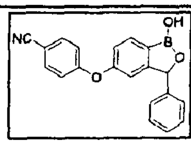 | -2 | -12 | 18 | 24 |
| 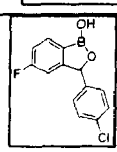 | -38 | -34 | 7 | -7 |
| 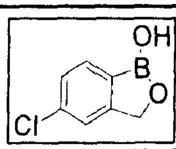 | -54 | 3 | 48 | 54 |
|  | | | 2 | 9 |

| No. | $R^{9a}$ | $R^{10a}$ | $R^{11a}$ | $R^{12a}$ |
|---|---|---|---|---|
| 1 | F | H | H | H |
| 2 | H | F | H | H |
| 3 | H | H | F | H |
| 4 | H | H | H | F |
| 5 | F | F | H | H |
| 6 | H | F | F | H |
| 7 | H | H | F | F |
| 8 | F | H | F | H |
| 9 | H | F | H | F |
| 10 | F | H | H | F |
| 11 | H | F | F | F |
| 12 | F | H | F | F |
| 13 | F | F | H | F |
| 14 | F | F | F | H |
| 15 | F | F | F | F |
| 16 | Cl | H | H | H |
| 17 | H | Cl | H | H |
| 18 | H | H | Cl | H |
| 19 | H | H | H | Cl |
| 20 | Cl | Cl | H | H |
| 21 | H | Cl | Cl | H |
| 22 | H | H | Cl | Cl |
| 23 | Cl | H | Cl | H |
| 24 | H | Cl | H | Cl |
| 25 | Cl | H | H | Cl |
| 26 | H | Cl | Cl | Cl |
| 27 | Cl | H | Cl | Cl |
| 28 | Cl | Cl | H | Cl |
| 29 | Cl | Cl | Cl | H |
| 30 | Cl | Cl | Cl | Cl |
| 31 | Br | H | H | H |

FIGURE 2B

| No. | $R^{9a}$ | $R^{10a}$ | $R^{11a}$ | $R^{12a}$ |
|---|---|---|---|---|
| 32 | H | Br | H | H |
| 33 | H | H | Br | H |
| 34 | H | H | H | Br |
| 35 | Br | Br | H | H |
| 36 | H | Br | Br | H |
| 37 | H | H | Br | Br |
| 38 | Br | H | Br | H |
| 39 | H | Br | H | Br |
| 40 | Br | H | H | Br |
| 41 | H | Br | Br | Br |
| 42 | Br | H | Br | Br |
| 43 | Br | Br | H | Br |
| 44 | Br | Br | Br | H |
| 45 | Br | Br | Br | Br |
| 46 | -CN | H | H | H |
| 47 | H | -CN | H | H |
| 48 | H | H | -CN | H |
| 49 | H | H | H | -CN |
| 50 | -CN | -CN | H | H |
| 51 | H | -CN | -CN | H |
| 52 | H | H | -CN | -CN |
| 53 | -CN | H | -CN | H |
| 54 | H | -CN | H | -CN |
| 55 | -CN | H | H | -CN |
| 56 | H | -CN | -CN | -CN |
| 57 | -CN | H | -CN | -CN |
| 58 | -CN | -CN | H | -CN |
| 59 | -CN | -CN | -CN | H |
| 60 | -CN | -CN | -CN | -CN |
| 61 | -Me | H | H | H |
| 62 | H | -Me | H | H |
| 63 | H | H | -Me | H |
| 64 | H | H | H | -Me |
| 65 | -Me | -Me | H | H |
| 66 | H | -Me | -Me | H |
| 67 | H | H | -Me | -Me |
| 68 | -Me | H | -Me | H |
| 69 | H | -Me | H | -Me |
| 70 | -Me | H | H | -Me |
| 71 | H | -Me | -Me | -Me |
| 72 | -Me | H | -Me | -Me |

FIGURE 2C

| No. | $R^{9a}$ | $R^{10a}$ | $R^{11a}$ | $R^{12a}$ |
|---|---|---|---|---|
| 73 | -Me | -Me | H | -Me |
| 74 | -Me | -Me | -Me | H |
| 75 | -Me | -Me | -Me | -Me |
| 76 | -CH$_2$OH | H | H | H |
| 77 | H | -CH$_2$OH | H | H |
| 78 | H | H | -CH$_2$OH | H |
| 79 | H | H | H | -CH$_2$OH |
| 80 | -CH$_2$OH | -CH$_2$OH | H | H |
| 81 | H | -CH$_2$OH | -CH$_2$OH | H |
| 82 | H | H | -CH$_2$OH | -CH$_2$OH |
| 83 | -CH$_2$OH | H | -CH$_2$OH | H |
| 84 | H | -CH$_2$OH | H | -CH$_2$OH |
| 85 | -CH$_2$OH | H | H | -CH$_2$OH |
| 86 | H | -CH$_2$OH | -CH$_2$OH | -CH$_2$OH |
| 87 | -CH$_2$OH | H | -CH$_2$OH | -CH$_2$OH |
| 88 | -CH$_2$OH | -CH$_2$OH | H | -CH$_2$OH |
| 89 | -CH$_2$OH | -CH$_2$OH | -CH$_2$OH | H |
| 90 | -CH$_2$OH | -CH$_2$OH | -CH$_2$OH | -CH$_2$OH |
| 91 | -benzyl | H | H | H |
| 92 | H | -benzyl | H | H |
| 93 | H | H | -benzyl | H |
| 94 | H | H | H | -benzyl |
| 95 | -benzyl | -benzyl | H | H |
| 96 | H | -benzyl | -benzyl | H |
| 97 | H | H | -benzyl | -benzyl |
| 98 | -benzyl | H | -benzyl | H |
| 99 | H | -benzyl | H | -benzyl |
| 100 | -benzyl | H | H | -benzyl |
| 101 | H | -benzyl | -benzyl | -benzyl |
| 102 | -benzyl | H | -benzyl | -benzyl |
| 103 | -benzyl | -benzyl | H | -benzyl |
| 104 | -benzyl | -benzyl | -benzyl | H |
| 105 | -benzyl | -benzyl | -benzyl | -benzyl |
| 106 | -OMe | H | H | H |
| 107 | H | -OMe | H | H |
| 108 | H | H | -OMe | H |
| 109 | H | H | H | -OMe |
| 110 | -OMe | -OMe | H | H |
| 111 | H | -OMe | -OMe | H |
| 112 | H | H | -OMe | -OMe |
| 113 | -OMe | H | -OMe | H |

FIGURE 2D

| No. | $R^{9a}$ | $R^{10a}$ | $R^{11a}$ | $R^{12a}$ |
|---|---|---|---|---|
| 114 | -OMe | H | H | -OMe |
| 115 | H | -OMe | -OMe | -OMe |
| 116 | -OMe | H | -OMe | -OMe |
| 117 | -OMe | -OMe | H | -OMe |
| 118 | -OMe | -OMe | -OMe | H |
| 119 | -OMe | -OMe | -OMe | -OMe |
| 120 | -4-cyanophenoxy | H | H | H |
| 121 | H | -4-cyanophenoxy | H | H |
| 122 | H | H | -4-cyanophenoxy | H |
| 123 | H | H | H | -4-cyanophenoxy |
| 124 | -4-cyanophenoxy | -4-cyanophenoxy | H | H |
| 125 | H | -4-cyanophenoxy | -4-cyanophenoxy | H |
| 126 | H | H | -4-cyanophenoxy | -4-cyanophenoxy |
| 127 | -4-cyanophenoxy | H | -4-cyanophenoxy | H |
| 128 | H | -4-cyanophenoxy | H | -4-cyanophenoxy |
| 129 | -4-cyanophenoxy | H | H | -4-cyanophenoxy |
| 130 | H | -4-cyanophenoxy | -4-cyanophenoxy | -4-cyanophenoxy |
| 131 | -4-cyanophenoxy | H | -4-cyanophenoxy | -4-cyanophenoxy |
| 132 | -4-cyanophenoxy | -4-cyanophenoxy | H | -4-cyanophenoxy |
| 133 | -4-cyanophenoxy | -4-cyanophenoxy | -4-cyanophenoxy | H |
| 134 | -4-cyanophenoxy | -4-cyanophenoxy | -4-cyanophenoxy | -4-cyanophenoxy |
| 135 | -3-cyanophenoxy | H | H | H |
| 136 | H | -3-cyanophenoxy | H | H |
| 137 | H | H | -3-cyanophenoxy | H |
| 138 | H | H | H | -3-cyanophenoxy |
| 139 | -3-cyanophenoxy | -3-cyanophenoxy | H | H |
| 140 | H | -3-cyanophenoxy | -3-cyanophenoxy | H |
| 141 | H | H | -3-cyanophenoxy | -3-cyanophenoxy |
| 142 | -3-cyanophenoxy | H | -3-cyanophenoxy | H |
| 143 | H | -3-cyanophenoxy | H | -3-cyanophenoxy |
| 144 | -3-cyanophenoxy | H | H | -3-cyanophenoxy |
| 145 | H | -3-cyanophenoxy | -3-cyanophenoxy | -3-cyanophenoxy |
| 146 | -3-cyanophenoxy | H | -3-cyanophenoxy | -3-cyanophenoxy |
| 147 | -3-cyanophenoxy | -3-cyanophenoxy | H | -3-cyanophenoxy |
| 148 | -3-cyanophenoxy | -3-cyanophenoxy | -3-cyanophenoxy | H |
| 149 | -3-cyanophenoxy | -3-cyanophenoxy | -3-cyanophenoxy | -3-cyanophenoxy |
| 150 | -2-cyanophenoxy | H | H | H |
| 151 | H | -2-cyanophenoxy | H | H |
| 152 | H | H | -2-cyanophenoxy | H |
| 153 | H | H | H | -2-cyanophenoxy |

FIGURE 2E

| No. | $R^{9a}$ | $R^{10a}$ | $R^{11a}$ | $R^{12a}$ |
|---|---|---|---|---|
| 154 | -2-cyanophenoxy | -2-cyanophenoxy | H | H |
| 155 | H | -2-cyanophenoxy | -2-cyanophenoxy | H |
| 156 | H | H | -2-cyanophenoxy | -2-cyanophenoxy |
| 157 | -2-cyanophenoxy | H | -2-cyanophenoxy | H |
| 158 | H | -2-cyanophenoxy | H | -2-cyanophenoxy |
| 159 | -2-cyanophenoxy | H | H | -2-cyanophenoxy |
| 160 | H | -2-cyanophenoxy | -2-cyanophenoxy | -2-cyanophenoxy |
| 161 | -2-cyanophenoxy | H | -2-cyanophenoxy | -2-cyanophenoxy |
| 162 | -2-cyanophenoxy | -2-cyanophenoxy | H | -2-cyanophenoxy |
| 163 | -2-cyanophenoxy | -2-cyanophenoxy | -2-cyanophenoxy | H |
| 164 | -2-cyanophenoxy | -2-cyanophenoxy | -2-cyanophenoxy | -2-cyanophenoxy |
| 165 | -4-chlorophenoxy | H | H | H |
| 166 | H | -4-chlorophenoxy | H | H |
| 167 | H | H | -4-chlorophenoxy | H |
| 168 | H | H | H | -4-chlorophenoxy |
| 169 | -4-chlorophenoxy | -4-chlorophenoxy | H | H |
| 170 | H | -4-chlorophenoxy | -4-chlorophenoxy | H |
| 171 | H | H | -4-chlorophenoxy | -4-chlorophenoxy |
| 172 | -4-chlorophenoxy | H | -4-chlorophenoxy | H |
| 173 | H | -4-chlorophenoxy | H | -4-chlorophenoxy |
| 174 | -4-chlorophenoxy | H | H | -4-chlorophenoxy |
| 175 | H | -4-chlorophenoxy | -4-chlorophenoxy | -4-chlorophenoxy |
| 176 | -4-chlorophenoxy | H | -4-chlorophenoxy | -4-chlorophenoxy |
| 177 | -4-chlorophenoxy | -4-chlorophenoxy | H | -4-chlorophenoxy |
| 178 | -4-chlorophenoxy | -4-chlorophenoxy | -4-chlorophenoxy | H |
| 179 | -4-chlorophenoxy | -4-chlorophenoxy | -4-chlorophenoxy | -4-chlorophenoxy |
| 180 | -3-chlorophenoxy | H | H | H |
| 181 | H | -3-chlorophenoxy | H | H |
| 182 | H | H | -3-chlorophenoxy | H |
| 183 | H | H | H | -3-chlorophenoxy |
| 184 | -3-chlorophenoxy | -3-chlorophenoxy | H | H |
| 185 | H | -3-chlorophenoxy | -3-chlorophenoxy | H |
| 186 | H | H | -3-chlorophenoxy | -3-chlorophenoxy |
| 187 | -3-chlorophenoxy | H | -3-chlorophenoxy | H |
| 188 | H | -3-chlorophenoxy | H | -3-chlorophenoxy |
| 189 | -3-chlorophenoxy | H | H | -3-chlorophenoxy |
| 190 | H | -3-chlorophenoxy | -3-chlorophenoxy | -3-chlorophenoxy |
| 191 | -3-chlorophenoxy | H | -3-chlorophenoxy | -3-chlorophenoxy |
| 192 | -3-chlorophenoxy | -3-chlorophenoxy | H | -3-chlorophenoxy |
| 193 | -3-chlorophenoxy | -3-chlorophenoxy | -3-chlorophenoxy | H |
| 194 | -3-chlorophenoxy | -3-chlorophenoxy | -3-chlorophenoxy | -3-chlorophenoxy |

FIGURE 2F

| No. | $R^{9a}$ | $R^{10a}$ | $R^{11a}$ | $R^{12a}$ |
|---|---|---|---|---|
| 195 | -2-chlorophenoxy | H | H | H |
| 196 | H | -2-chlorophenoxy | H | H |
| 197 | H | H | -2-chlorophenoxy | H |
| 198 | H | H | H | -2-chlorophenoxy |
| 199 | -2-chlorophenoxy | -2-chlorophenoxy | H | H |
| 200 | H | -2-chlorophenoxy | -2-chlorophenoxy | H |
| 201 | H | H | -2-chlorophenoxy | -2-chlorophenoxy |
| 202 | -2-chlorophenoxy | H | -2-chlorophenoxy | H |
| 203 | H | -2-chlorophenoxy | H | -2-chlorophenoxy |
| 204 | -2-chlorophenoxy | H | H | -2-chlorophenoxy |
| 205 | H | -2-chlorophenoxy | -2-chlorophenoxy | -2-chlorophenoxy |
| 206 | -2-chlorophenoxy | H | -2-chlorophenoxy | -2-chlorophenoxy |
| 207 | -2-chlorophenoxy | -2-chlorophenoxy | H | -2-chlorophenoxy |
| 208 | -2-chlorophenoxy | -2-chlorophenoxy | -2-chlorophenoxy | H |
| 209 | -2-chlorophenoxy | -2-chlorophenoxy | -2-chlorophenoxy | -2-chlorophenoxy |
| 210 | -phenoxy | H | H | H |
| 211 | H | -phenoxy | H | H |
| 212 | H | H | -phenoxy | H |
| 213 | H | H | H | -phenoxy |
| 214 | -phenoxy | -phenoxy | H | H |
| 215 | H | -phenoxy | -phenoxy | H |
| 216 | H | H | -phenoxy | -phenoxy |
| 217 | -phenoxy | H | -phenoxy | H |
| 218 | H | -phenoxy | H | -phenoxy |
| 219 | -phenoxy | H | H | -phenoxy |
| 220 | H | -phenoxy | -phenoxy | -phenoxy |
| 221 | -phenoxy | H | -phenoxy | -phenoxy |
| 222 | -phenoxy | -phenoxy | H | -phenoxy |
| 223 | -phenoxy | -phenoxy | -phenoxy | H |
| 224 | -phenoxy | -phenoxy | -phenoxy | -phenoxy |
| 225 | -4-cyanophenylthio | H | H | H |
| 226 | H | -4-cyanophenylthio | H | H |
| 227 | H | H | -4-cyanophenylthio | H |
| 228 | H | H | H | -4-cyanophenylthio |
| 229 | -4-cyanophenylthio | -4-cyanophenylthio | H | H |
| 230 | H | -4-cyanophenylthio | -4-cyanophenylthio | H |
| 231 | H | H | -4-cyanophenylthio | -4-cyanophenylthio |
| 232 | -4-cyanophenylthio | H | -4-cyanophenylthio | H |
| 233 | H | -4-cyanophenylthio | H | -4-cyanophenylthio |
| 234 | -4-cyanophenylthio | H | H | -4-cyanophenylthio |
| 235 | H | -4-cyanophenylthio | -4-cyanophenylthio | -4-cyanophenylthio |

FIGURE 2G

| No. | $R^{9a}$ | $R^{10a}$ | $R^{11a}$ | $R^{12a}$ |
|---|---|---|---|---|
| 236 | -4-cyanophenylthio | H | -4-cyanophenylthio | -4-cyanophenylthio |
| 237 | -4-cyanophenylthio | -4-cyanophenylthio | H | -4-cyanophenylthio |
| 238 | -4-cyanophenylthio | -4-cyanophenylthio | -4-cyanophenylthio | H |
| 239 | -4-cyanophenylthio | -4-cyanophenylthio | -4-cyanophenylthio | -4-cyanophenylthio |
| 240 | -3-cyanophenylthio | H | H | H |
| 241 | H | 3-cyanophenylthio | H | H |
| 242 | H | H | -3-cyanophenylthio | H |
| 243 | H | H | H | -3-cyanophenylthio |
| 244 | -3-cyanophenylthio | -3-cyanophenylthio | H | H |
| 245 | H | -3-cyanophenylthio | -3-cyanophenylthio | H |
| 246 | H | H | -3-cyanophenylthio | -3-cyanophenylthio |
| 247 | -3-cyanophenylthio | H | -3-cyanophenylthio | H |
| 248 | H | -3-cyanophenylthio | H | -3-cyanophenylthio |
| 249 | -3-cyanophenylthio | H | H | -3-cyanophenylthio |
| 250 | H | -3-cyanophenylthio | -3-cyanophenylthio | -3-cyanophenylthio |
| 251 | -3-cyanophenylthio | H | -3-cyanophenylthio | -3-cyanophenylthio |
| 252 | -3-cyanophenylthio | -3-cyanophenylthio | H | -3-cyanophenylthio |
| 253 | -3-cyanophenylthio | -3-cyanophenylthio | -3-cyanophenylthio | H |
| 254 | -3-cyanophenylthio | -3-cyanophenylthio | -3-cyanophenylthio | -3-cyanophenylthio |
| 255 | -2-cyanophenylthio | H | H | H |
| 256 | H | -2-cyanophenylthio | H | H |
| 257 | H | H | -2-cyanophenylthio | H |
| 258 | H | H | H | -2-cyanophenylthio |
| 259 | -2-cyanophenylthio | -2-cyanophenylthio | H | H |
| 260 | H | -2-cyanophenylthio | -2-cyanophenylthio | H |
| 261 | H | H | -2-cyanophenylthio | -2-cyanophenylthio |
| 262 | -2-cyanophenylthio | H | -2-cyanophenylthio | H |
| 263 | H | -2-cyanophenylthio | H | -2-cyanophenylthio |
| 264 | -2-cyanophenylthio | H | H | -2-cyanophenylthio |
| 265 | H | -2-cyanophenylthio | -2-cyanophenylthio | -2-cyanophenylthio |
| 266 | 2-cyanophenylthio | H | -2-cyanophenylthio | -2-cyanophenylthio |
| 267 | 2-cyanophenylthio | -2-cyanophenylthio | H | -2-cyanophenylthio |
| 268 | 2-cyanophenylthio | -2-cyanophenylthio | -2-cyanophenylthio | H |
| 269 | 2-cyanophenylthio | -2-cyanophenylthio | -2-cyanophenylthio | -2-cyanophenylthio |
| 270 | -OCH$_2$C(O)OH | H | H | H |
| 271 | H | -OCH$_2$C(O)OH | H | H |
| 272 | H | H | -OCH$_2$C(O)OH | H |
| 273 | H | H | H | -OCH$_2$C(O)OH |
| 274 | F | -OCH$_2$C(O)OH | H | H |
| 275 | H | -OCH$_2$C(O)OH | F | H |

FIGURE 2H

| No. | $R^{9a}$ | $R^{10a}$ | $R^{11a}$ | $R^{12a}$ |
|---|---|---|---|---|
| 276 | H | -OCH$_2$C(O)OH | H | F |
| 277 | F | -OCH$_2$C(O)OH | F | H |
| 278 | H | -OCH$_2$C(O)OH | F | F |
| 279 | F | -OCH$_2$C(O)OH | F | F |
| 280 | -NMeS(O)$_2$Ph | H | H | H |
| 281 | H | -NMeS(O)$_2$Ph | H | H |
| 282 | H | H | -NMeS(O)$_2$Ph | H |
| 283 | H | H | H | -NMeS(O)$_2$Ph |
| 284 | F | -NMeS(O)$_2$Ph | H | H |
| 285 | H | -NMeS(O)$_2$Ph | F | H |
| 286 | H | -NMeS(O)$_2$Ph | H | F |
| 287 | F | -NMeS(O)$_2$Ph | F | H |
| 288 | H | -NMeS(O)$_2$Ph | F | F |
| 289 | F | -NMeS(O)$_2$Ph | F | F |
| 290 | -CH$_2$OH | H | H | H |
| 291 | H | -CH$_2$OH | H | H |
| 292 | H | H | -CH$_2$OH | H |
| 293 | H | H | H | -CH$_2$OH |
| 294 | -CH$_2$OH | F | H | H |
| 295 | -CH$_2$OH | H | F | H |
| 296 | -CH$_2$OH | H | H | F |
| 297 | -CH$_2$OH | Cl | H | H |
| 298 | -CH$_2$OH | H | Cl | H |
| 299 | -CH$_2$OH | H | H | Cl |
| 300 | F | -CH$_2$OH | H | H |
| 301 | H | -CH$_2$OH | F | H |
| 302 | H | -CH$_2$OH | H | F |
| 303 | Cl | -CH$_2$OH | H | H |
| 304 | H | -CH$_2$OH | Cl | H |
| 305 | H | -CH$_2$OH | H | Cl |
| 306 | F | H | -CH$_2$OH | H |
| 307 | H | F | -CH$_2$OH | H |
| 308 | H | H | -CH$_2$OH | F |
| 309 | Cl | H | -CH$_2$OH | H |
| 310 | H | Cl | -CH$_2$OH | H |
| 311 | H | H | -CH$_2$OH | Cl |
| 312 | F | H | H | -CH$_2$OH |
| 313 | H | F | H | -CH$_2$OH |
| 314 | H | H | F | -CH$_2$OH |
| 315 | Cl | H | H | -CH$_2$OH |
| 316 | H | Cl | H | -CH$_2$OH |

FIGURE 2I

| No. | $R^{9a}$ | $R^{10a}$ | $R^{11a}$ | $R^{12a}$ |
|---|---|---|---|---|
| 317 | H | H | Cl | -CH$_2$OH |
| 318 | F | -CH$_2$OH | F | H |
| 319 | H | -CH$_2$OH | F | F |
| 320 | F | -CH$_2$OH | F | F |
| 321 | H | -NH$_2$ | H | H |
| 322 | H | H | -NH$_2$ | H |
| 323 | H | H | H | -NH$_2$ |
| 324 | -NH$_2$ | F | H | H |
| 325 | -NH$_2$ | H | F | H |
| 326 | -NH$_2$ | H | H | F |
| 327 | -NH$_2$ | Cl | H | H |
| 328 | -NH$_2$ | H | Cl | H |
| 329 | -NH$_2$ | H | H | Cl |
| 330 | F | -NH$_2$ | H | H |
| 331 | H | -NH$_2$ | F | H |
| 332 | H | -NH$_2$ | H | F |
| 333 | Cl | -NH$_2$ | H | H |
| 334 | H | -NH$_2$ | Cl | H |
| 335 | H | -NH$_2$ | H | Cl |
| 336 | F | H | -NH$_2$ | H |
| 337 | H | F | -NH$_2$ | H |
| 338 | H | H | -NH$_2$ | F |
| 339 | Cl | H | -NH$_2$ | H |
| 340 | H | Cl | -NH$_2$ | H |
| 341 | H | H | -NH$_2$ | Cl |
| 342 | F | H | H | -NH$_2$ |
| 343 | H | F | H | -NH$_2$ |
| 344 | H | H | F | -NH$_2$ |
| 345 | Cl | H | H | -NH$_2$ |
| 346 | H | Cl | H | -NH$_2$ |
| 347 | H | H | Cl | -NH$_2$ |
| 348 | F | -NH$_2$ | F | H |
| 349 | H | -NH$_2$ | F | F |
| 350 | F | -NH$_2$ | F | F |
| 351 | -O(4-CN-Ph) | H | H | H |
| 352 | H | -O(4-CN-Ph) | H | H |
| 353 | H | H | -O(4-CN-Ph) | H |
| 354 | H | H | H | -O(4-CN-Ph) |
| 355 | F | -O(4-CN-Ph) | H | H |
| 356 | H | -O(4-CN-Ph) | F | H |
| 357 | H | -O(4-CN-Ph) | H | F |

FIGURE 2J

| No. | $R^{9a}$ | $R^{10a}$ | $R^{11a}$ | $R^{12a}$ |
|---|---|---|---|---|
| 358 | F | -O(4-CN-Ph) | F | H |
| 359 | H | -O(4-CN-Ph) | F | F |
| 360 | F | -O(4-CN-Ph) | F | F |
| 361 | 3-(phenylthio)-1H-indol-1-yl | H | H | H |
| 362 | H | 3-(phenylthio)-1H-indol-1-yl | H | H |
| 363 | H | H | 3-(phenylthio)-1H-indol-1-yl | H |
| 364 | H | H | H | 3-(phenylthio)-1H-indol-1-yl |
| 365 | F | 3-(phenylthio)-1H-indol-1-yl | H | H |
| 366 | H | 3-(phenylthio)-1H-indol-1-yl | F | H |
| 367 | H | 3-(phenylthio)-1H-indol-1-yl | H | F |
| 368 | F | 3-(phenylthio)-1H-indol-1-yl | F | H |
| 369 | H | 3-(phenylthio)-1H-indol-1-yl | F | F |
| 370 | F | 3-(phenylthio)-1H-indol-1-yl | F | F |
| 371 | dibenzylamino | H | H | H |
| 372 | H | dibenzylamino | H | H |
| 373 | H | H | dibenzylamino | H |
| 374 | H | H | H | dibenzylamino |
| 375 | F | dibenzylamino | H | H |
| 376 | H | dibenzylamino | F | H |
| 377 | H | dibenzylamino | H | F |
| 378 | F | dibenzylamino | F | H |
| 379 | H | dibenzylamino | F | F |
| 380 | F | dibenzylamino | F | F |
| 381 | -S(O)$_2$(4-Cl-Ph) | H | H | H |
| 382 | H | -S(O)$_2$(4-Cl-Ph) | H | H |
| 383 | H | H | -S(O)$_2$(4-Cl-Ph) | H |
| 384 | H | H | H | -S(O)$_2$(4-Cl-Ph) |
| 385 | F | -S(O)$_2$(4-Cl-Ph) | H | H |
| 386 | H | -S(O)$_2$(4-Cl-Ph) | F | H |
| 387 | H | -S(O)$_2$(4-Cl-Ph) | H | F |
| 388 | F | -S(O)$_2$(4-Cl-Ph) | F | H |
| 389 | H | -S(O)$_2$(4-Cl-Ph) | F | F |
| 390 | F | -S(O)$_2$(4-Cl-Ph) | F | F |
| 391 | -S(4-pyridyl) | H | H | H |
| 392 | H | -S(4-pyridyl) | H | H |
| 393 | H | H | -S(4-pyridyl) | H |

FIGURE 2K

| No. | $R^{9a}$ | $R^{10a}$ | $R^{11a}$ | $R^{12a}$ |
|---|---|---|---|---|
| 394 | H | H | H | -S(4-pyridyl) |
| 395 | F | -S(4-pyridyl) | H | H |
| 396 | H | -S(4-pyridyl) | F | H |
| 397 | H | -S(4-pyridyl) | H | F |
| 398 | F | -S(4-pyridyl) | F | H |
| 399 | H | -S(4-pyridyl) | F | F |
| 400 | F | -S(4-pyridyl) | F | F |
| 401 | -NHCH$_2$Ph | H | H | H |
| 402 | H | -NHCH$_2$Ph | H | H |
| 403 | H | H | -NHCH$_2$Ph | H |
| 404 | H | H | H | -NHCH$_2$Ph |
| 405 | F | -NHCH$_2$Ph | H | H |
| 406 | H | -NHCH$_2$Ph | F | H |
| 407 | H | -NHCH$_2$Ph | H | F |
| 408 | F | -NHCH$_2$Ph | F | H |
| 409 | H | -NHCH$_2$Ph | F | F |
| 410 | F | -NHCH$_2$Ph | F | F |

FIGURE 3A

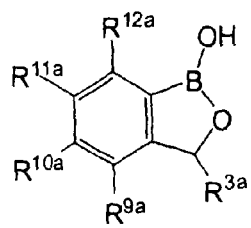

| No. | R³ᵃ | R⁹ᵃ | R¹⁰ᵃ | R¹¹ᵃ | R¹²ᵃ |
|---|---|---|---|---|---|
| 1 | -CH₂Ph | F | H | H | H |
| 2 | -CH₂Ph | H | F | H | H |
| 3 | -CH₂Ph | H | H | F | H |
| 4 | -CH₂Ph | H | H | H | F |
| 5 | -CH₂Ph | F | F | H | H |
| 6 | -CH₂Ph | H | F | F | H |
| 7 | -CH₂Ph | H | H | F | F |
| 8 | -CH₂Ph | F | H | F | H |
| 9 | -CH₂Ph | H | F | H | F |
| 10 | -CH₂Ph | F | H | H | F |
| 11 | -CH₂Ph | H | F | F | F |
| 12 | -CH₂Ph | F | H | F | F |
| 13 | -CH₂Ph | F | F | H | F |
| 14 | -CH₂Ph | F | F | F | H |
| 15 | -CH₂Ph | F | F | F | F |
| 16 | -CH₂Ph | -OCH₂C(O)OH | H | H | H |
| 17 | -CH₂Ph | H | -OCH₂C(O)OH | H | H |
| 18 | -CH₂Ph | H | H | -OCH₂C(O)OH | H |
| 19 | -CH₂Ph | H | H | H | -OCH₂C(O)OH |
| 20 | -CH₂Ph | F | -OCH₂C(O)OH | H | H |
| 21 | -CH₂Ph | H | -OCH₂C(O)OH | F | H |
| 22 | -CH₂Ph | H | -OCH₂C(O)OH | H | F |
| 23 | -CH₂Ph | F | -OCH₂C(O)OH | F | H |
| 24 | -CH₂Ph | H | -OCH₂C(O)OH | F | F |
| 25 | -CH₂Ph | F | -OCH₂C(O)OH | F | F |
| 26 | -CH₂Ph | -NMeS(O)₂Ph | H | H | H |
| 27 | -CH₂Ph | H | -NMeS(O)₂Ph | H | H |
| 28 | -CH₂Ph | H | H | -NMeS(O)₂Ph | H |
| 29 | -CH₂Ph | H | H | H | -NMeS(O)₂Ph |
| 30 | -CH₂Ph | F | -NMeS(O)₂Ph | H | H |
| 31 | -CH₂Ph | H | -NMeS(O)₂Ph | F | H |
| 32 | -CH₂Ph | H | -NMeS(O)₂Ph | H | F |
| 33 | -CH₂Ph | F | -NMeS(O)₂Ph | F | H |

FIGURE 3B

| No. | $R^{3a}$ | $R^{9a}$ | $R^{10a}$ | $R^{11a}$ | $R^{12a}$ |
|---|---|---|---|---|---|
| 34 | -CH$_2$Ph | H | -NMeS(O)$_2$Ph | F | F |
| 35 | -CH$_2$Ph | F | -NMeS(O)$_2$Ph | F | F |
| 36 | -CH$_2$Ph | H | -CH$_2$OH | H | H |
| 37 | -CH$_2$Ph | H | H | -CH$_2$OH | H |
| 38 | -CH$_2$Ph | H | H | H | -CH$_2$OH |
| 39 | -CH$_2$Ph | -CH$_2$OH | F | H | H |
| 40 | -CH$_2$Ph | -CH$_2$OH | H | F | H |
| 41 | -CH$_2$Ph | -CH$_2$OH | H | H | F |
| 42 | -CH$_2$Ph | -CH$_2$OH | Cl | H | H |
| 43 | -CH$_2$Ph | -CH$_2$OH | H | Cl | H |
| 44 | -CH$_2$Ph | -CH$_2$OH | H | H | Cl |
| 45 | -CH$_2$Ph | F | -CH$_2$OH | H | H |
| 46 | -CH$_2$Ph | H | -CH$_2$OH | F | H |
| 47 | -CH$_2$Ph | H | -CH$_2$OH | H | F |
| 48 | -CH$_2$Ph | Cl | -CH$_2$OH | H | H |
| 49 | -CH$_2$Ph | H | -CH$_2$OH | Cl | H |
| 50 | -CH$_2$Ph | H | -CH$_2$OH | H | Cl |
| 51 | -CH$_2$Ph | F | H | -CH$_2$OH | H |
| 52 | -CH$_2$Ph | H | F | -CH$_2$OH | H |
| 53 | -CH$_2$Ph | H | H | -CH$_2$OH | F |
| 54 | -CH$_2$Ph | Cl | H | -CH$_2$OH | H |
| 55 | -CH$_2$Ph | H | Cl | -CH$_2$OH | H |
| 56 | -CH$_2$Ph | H | H | -CH$_2$OH | Cl |
| 57 | -CH$_2$Ph | F | H | H | -CH$_2$OH |
| 58 | -CH$_2$Ph | H | F | H | -CH$_2$OH |
| 59 | -CH$_2$Ph | H | H | F | -CH$_2$OH |
| 60 | -CH$_2$Ph | Cl | H | H | -CH$_2$OH |
| 61 | -CH$_2$Ph | H | Cl | H | -CH$_2$OH |
| 62 | -CH$_2$Ph | H | H | Cl | -CH$_2$OH |
| 63 | -CH$_2$Ph | F | -CH$_2$OH | F | H |
| 64 | -CH$_2$Ph | H | -CH$_2$OH | F | F |
| 65 | -CH$_2$Ph | F | -CH$_2$OH | F | F |
| 66 | -CH$_2$Ph | H | -NH$_2$ | H | H |
| 67 | -CH$_2$Ph | H | H | -NH$_2$ | H |
| 68 | -CH$_2$Ph | H | H | H | -NH$_2$ |
| 69 | -CH$_2$Ph | -NH$_2$ | F | H | H |
| 70 | -CH$_2$Ph | -NH$_2$ | H | F | H |
| 71 | -CH$_2$Ph | -NH$_2$ | H | H | F |
| 72 | -CH$_2$Ph | -NH$_2$ | Cl | H | H |
| 73 | -CH$_2$Ph | -NH$_2$ | H | Cl | H |
| 74 | -CH$_2$Ph | -NH$_2$ | H | H | Cl |
| 75 | -CH$_2$Ph | F | -NH$_2$ | H | H |

FIGURE 3C

| No. | $R^{3a}$ | $R^{9a}$ | $R^{10a}$ | $R^{11a}$ | $R^{12a}$ |
|---|---|---|---|---|---|
| 76 | -CH$_2$Ph | H | -NH$_2$ | F | H |
| 77 | -CH$_2$Ph | H | -NH$_2$ | H | F |
| 78 | -CH$_2$Ph | Cl | -NH$_2$ | H | H |
| 79 | -CH$_2$Ph | H | -NH$_2$ | Cl | H |
| 80 | -CH$_2$Ph | H | -NH$_2$ | H | Cl |
| 81 | -CH$_2$Ph | F | H | -NH$_2$ | H |
| 82 | -CH$_2$Ph | H | F | -NH$_2$ | H |
| 83 | -CH$_2$Ph | H | H | -NH$_2$ | F |
| 84 | -CH$_2$Ph | Cl | H | -NH$_2$ | H |
| 85 | -CH$_2$Ph | H | Cl | -NH$_2$ | H |
| 86 | -CH$_2$Ph | H | H | -NH$_2$ | Cl |
| 87 | -CH$_2$Ph | F | H | H | -NH$_2$ |
| 88 | -CH$_2$Ph | H | F | H | -NH$_2$ |
| 89 | -CH$_2$Ph | H | H | F | -NH$_2$ |
| 90 | -CH$_2$Ph | Cl | H | H | -NH$_2$ |
| 91 | -CH$_2$Ph | H | Cl | H | -NH$_2$ |
| 92 | -CH$_2$Ph | H | H | Cl | -NH$_2$ |
| 93 | -CH$_2$Ph | F | -NH$_2$ | F | H |
| 94 | -CH$_2$Ph | H | -NH$_2$ | F | F |
| 95 | -CH$_2$Ph | F | -NH$_2$ | F | F |
| 96 | -CH$_2$Ph | -O(4-CN-Ph) | H | H | H |
| 97 | -CH$_2$Ph | H | -O(4-CN-Ph) | H | H |
| 98 | -CH$_2$Ph | H | H | -O(4-CN-Ph) | H |
| 99 | -CH$_2$Ph | H | H | H | -O(4-CN-Ph) |
| 100 | -CH$_2$Ph | F | -O(4-CN-Ph) | H | H |
| 101 | -CH$_2$Ph | H | -O(4-CN-Ph) | F | H |
| 102 | -CH$_2$Ph | H | -O(4-CN-Ph) | H | F |
| 103 | -CH$_2$Ph | F | -O(4-CN-Ph) | F | H |
| 104 | -CH$_2$Ph | H | -O(4-CN-Ph) | F | F |
| 105 | -CH$_2$Ph | F | -O(4-CN-Ph) | F | F |
| 106 | -CH$_2$Ph | 3-(phenylthio)-1H-indol-1-yl | H | H | H |
| 107 | -CH$_2$Ph | H | 3-(phenylthio)-1H-indol-1-yl | H | H |
| 108 | -CH$_2$Ph | H | H | 3-(phenylthio)-1H-indol-1-yl | H |
| 109 | -CH$_2$Ph | H | H | H | 3-(phenylthio)-1H-indol-1-yl |
| 110 | -CH$_2$Ph | F | 3-(phenylthio)-1H-indol-1-yl | H | H |
| 111 | -CH$_2$Ph | H | 3-(phenylthio)-1H-indol-1-yl | F | H |
| 112 | -CH$_2$Ph | H | 3-(phenylthio)-1H-indol-1-yl | H | F |
| 113 | -CH$_2$Ph | F | 3-(phenylthio)-1H-indol-1-yl | F | H |

FIGURE 3D

| No. | $R^{3a}$ | $R^{9a}$ | $R^{10a}$ | $R^{11a}$ | $R^{12a}$ |
|---|---|---|---|---|---|
| 114 | -CH₂Ph | H | 3-(phenylthio)-1H-indol-1-yl | F | F |
| 115 | -CH₂Ph | F | 3-(phenylthio)-1H-indol-1-yl | F | F |
| 116 | -CH₂Ph | dibenzylamino | H | H | H |
| 117 | -CH₂Ph | H | dibenzylamino | H | H |
| 118 | -CH₂Ph | H | H | dibenzylamino | H |
| 119 | -CH₂Ph | H | H | H | dibenzylamino |
| 120 | -CH₂Ph | F | dibenzylamino | H | H |
| 121 | -CH₂Ph | H | dibenzylamino | F | H |
| 122 | -CH₂Ph | H | dibenzylamino | H | F |
| 123 | -CH₂Ph | F | dibenzylamino | F | H |
| 124 | -CH₂Ph | H | dibenzylamino | F | F |
| 125 | -CH₂Ph | F | dibenzylamino | F | F |
| 126 | -CH₂Ph | -S(O)₂(4-Cl-Ph) | H | H | H |
| 127 | -CH₂Ph | H | -S(O)₂(4-Cl-Ph) | H | H |
| 128 | -CH₂Ph | H | H | -S(O)₂(4-Cl-Ph) | H |
| 129 | -CH₂Ph | H | H | H | -S(O)₂(4-Cl-Ph) |
| 130 | -CH₂Ph | F | -S(O)₂(4-Cl-Ph) | H | H |
| 131 | -CH₂Ph | H | -S(O)₂(4-Cl-Ph) | F | H |
| 132 | -CH₂Ph | H | -S(O)₂(4-Cl-Ph) | H | F |
| 133 | -CH₂Ph | F | -S(O)₂(4-Cl-Ph) | F | H |
| 134 | -CH₂Ph | H | -S(O)₂(4-Cl-Ph) | F | F |
| 135 | -CH₂Ph | F | -S(O)₂(4-Cl-Ph) | F | F |
| 136 | -CH₂Ph | -S(4-pyridyl) | H | H | H |
| 137 | -CH₂Ph | H | -S(4-pyridyl) | H | H |
| 138 | -CH₂Ph | H | H | -S(4-pyridyl) | H |
| 139 | -CH₂Ph | H | H | H | -S(4-pyridyl) |
| 140 | -CH₂Ph | F | -S(4-pyridyl) | H | H |
| 141 | -CH₂Ph | H | -S(4-pyridyl) | F | H |
| 142 | -CH₂Ph | H | -S(4-pyridyl) | H | F |
| 143 | -CH₂Ph | F | -S(4-pyridyl) | F | H |
| 144 | -CH₂Ph | H | -S(4-pyridyl) | F | F |
| 145 | -CH₂Ph | F | -S(4-pyridyl) | F | F |
| 146 | -CH₂Ph | -NHCH₂Ph | H | H | H |
| 147 | -CH₂Ph | H | -NHCH₂Ph | H | H |
| 148 | -CH₂Ph | H | H | -NHCH₂Ph | H |
| 149 | -CH₂Ph | H | H | H | -NHCH₂Ph |
| 150 | -CH₂Ph | F | -NHCH₂Ph | H | H |
| 151 | -CH₂Ph | H | -NHCH₂Ph | F | H |
| 152 | -CH₂Ph | H | -NHCH₂Ph | H | F |
| 153 | -CH₂Ph | F | -NHCH₂Ph | F | H |
| 154 | -CH₂Ph | H | -NHCH₂Ph | F | F |

FIGURE 3E

| No. | $R^{3a}$ | $R^{9a}$ | $R^{10a}$ | $R^{11a}$ | $R^{12a}$ |
|---|---|---|---|---|---|
| 155 | -CH$_2$Ph | F | -NHCH$_2$Ph | F | F |
| 156 | Me | F | H | H | H |
| 157 | Me | H | F | H | H |
| 158 | Me | H | H | F | H |
| 159 | Me | H | H | H | F |
| 160 | Me | F | F | H | H |
| 161 | Me | H | F | F | H |
| 162 | Me | H | H | F | F |
| 163 | Me | F | H | F | H |
| 164 | Me | H | F | H | F |
| 165 | Me | F | H | H | F |
| 166 | Me | H | F | F | F |
| 167 | Me | F | H | F | F |
| 168 | Me | F | F | H | F |
| 169 | Me | F | F | F | H |
| 170 | Me | F | F | F | F |
| 171 | Me | -OCH$_2$C(O)OH | H | H | H |
| 172 | Me | H | -OCH$_2$C(O)OH | H | H |
| 173 | Me | H | H | -OCH$_2$C(O)OH | H |
| 174 | Me | H | H | H | -OCH$_2$C(O)OH |
| 175 | Me | F | -OCH$_2$C(O)OH | H | H |
| 176 | Me | H | -OCH$_2$C(O)OH | F | H |
| 177 | Me | H | -OCH$_2$C(O)OH | H | F |
| 178 | Me | F | -OCH$_2$C(O)OH | F | H |
| 179 | Me | H | -OCH$_2$C(O)OH | F | F |
| 180 | Me | F | -OCH$_2$C(O)OH | F | F |
| 181 | Me | -NMeS(O)$_2$Ph | H | H | H |
| 182 | Me | H | -NMeS(O)$_2$Ph | H | H |
| 183 | Me | H | H | -NMeS(O)$_2$Ph | H |
| 184 | Me | H | H | H | -NMeS(O)$_2$Ph |
| 185 | Me | F | -NMeS(O)$_2$Ph | H | H |
| 186 | Me | H | -NMeS(O)$_2$Ph | F | H |
| 187 | Me | H | -NMeS(O)$_2$Ph | H | F |
| 188 | Me | F | -NMeS(O)$_2$Ph | F | H |
| 189 | Me | H | -NMeS(O)$_2$Ph | F | F |
| 190 | Me | F | -NMeS(O)$_2$Ph | F | F |
| 191 | Me | H | -CH$_2$OH | H | H |
| 192 | Me | H | H | -CH$_2$OH | H |
| 193 | Me | H | H | H | -CH$_2$OH |
| 194 | Me | -CH$_2$OH | F | H | H |
| 195 | Me | -CH$_2$OH | H | F | H |

FIGURE 3F

| No. | $R^{3a}$ | $R^{9a}$ | $R^{10a}$ | $R^{11a}$ | $R^{12a}$ |
|---|---|---|---|---|---|
| 196 | Me | -CH₂OH | H | H | F |
| 197 | Me | -CH₂OH | Cl | H | H |
| 198 | Me | -CH₂OH | H | Cl | H |
| 199 | Me | -CH₂OH | H | H | Cl |
| 200 | Me | F | -CH₂OH | H | H |
| 201 | Me | H | -CH₂OH | F | H |
| 202 | Me | H | -CH₂OH | H | F |
| 203 | Me | Cl | -CH₂OH | H | H |
| 204 | Me | H | -CH₂OH | Cl | H |
| 205 | Me | H | -CH₂OH | H | Cl |
| 206 | Me | F | H | -CH₂OH | H |
| 207 | Me | H | F | -CH₂OH | H |
| 208 | Me | H | H | -CH₂OH | F |
| 209 | Me | Cl | H | -CH₂OH | H |
| 210 | Me | H | Cl | -CH₂OH | H |
| 211 | Me | H | H | -CH₂OH | Cl |
| 212 | Me | F | H | H | -CH₂OH |
| 213 | Me | H | F | H | -CH₂OH |
| 214 | Me | H | H | F | -CH₂OH |
| 215 | Me | Cl | H | H | -CH₂OH |
| 216 | Me | H | Cl | H | -CH₂OH |
| 217 | Me | H | H | Cl | -CH₂OH |
| 218 | Me | F | -CH₂OH | F | H |
| 219 | Me | H | -CH₂OH | F | F |
| 220 | Me | F | -CH₂OH | F | F |
| 221 | Me | H | -NH₂ | H | H |
| 222 | Me | H | H | -NH₂ | H |
| 223 | Me | H | H | H | -NH₂ |
| 224 | Me | -NH₂ | F | H | H |
| 225 | Me | -NH₂ | H | F | H |
| 226 | Me | -NH₂ | H | H | F |
| 227 | Me | -NH₂ | Cl | H | H |
| 228 | Me | -NH₂ | H | Cl | H |
| 229 | Me | -NH₂ | H | H | Cl |
| 230 | Me | F | -NH₂ | H | H |
| 231 | Me | H | -NH₂ | F | H |
| 232 | Me | H | -NH₂ | H | F |
| 233 | Me | Cl | -NH₂ | H | H |
| 234 | Me | H | -NH₂ | Cl | H |
| 235 | Me | H | -NH₂ | H | Cl |
| 236 | Me | F | H | -NH₂ | H |
| 237 | Me | H | F | -NH₂ | H |

FIGURE 3G

| No. | $R^{3a}$ | $R^{9a}$ | $R^{10a}$ | $R^{11a}$ | $R^{12a}$ |
|---|---|---|---|---|---|
| 238 | Me | H | H | -NH$_2$ | F |
| 239 | Me | Cl | H | -NH$_2$ | H |
| 240 | Me | H | Cl | -NH$_2$ | H |
| 241 | Me | H | H | -NH$_2$ | Cl |
| 242 | Me | F | H | H | -NH$_2$ |
| 243 | Me | H | F | H | -NH$_2$ |
| 244 | Me | H | H | F | -NH$_2$ |
| 245 | Me | Cl | H | H | -NH$_2$ |
| 246 | Me | H | Cl | H | -NH$_2$ |
| 247 | Me | H | H | Cl | -NH$_2$ |
| 248 | Me | F | -NH$_2$ | F | H |
| 249 | Me | H | -NH$_2$ | F | F |
| 250 | Me | F | -NH$_2$ | F | F |
| 251 | Me | -O(4-CN-Ph) | H | H | H |
| 252 | Me | H | -O(4-CN-Ph) | H | H |
| 253 | Me | H | H | -O(4-CN-Ph) | H |
| 254 | Me | H | H | H | -O(4-CN-Ph) |
| 255 | Me | F | -O(4-CN-Ph) | H | H |
| 256 | Me | H | -O(4-CN-Ph) | F | H |
| 257 | Me | H | -O(4-CN-Ph) | H | F |
| 258 | Me | F | -O(4-CN-Ph) | F | H |
| 259 | Me | H | -O(4-CN-Ph) | F | F |
| 260 | Me | F | -O(4-CN-Ph) | F | F |
| 261 | Me | 3-(phenylthio)-1H-indol-1-yl | H | H | H |
| 262 | Me | H | 3-(phenylthio)-1H-indol-1-yl | H | H |
| 263 | Me | H | H | 3-(phenylthio)-1H-indol-1-yl | H |
| 264 | Me | H | H | H | 3-(phenylthio)-1H-indol-1-yl |
| 265 | Me | F | 3-(phenylthio)-1H-indol-1-yl | H | H |
| 266 | Me | H | 3-(phenylthio)-1H-indol-1-yl | F | H |
| 267 | Me | H | 3-(phenylthio)-1H-indol-1-yl | H | F |
| 268 | Me | F | 3-(phenylthio)-1H-indol-1-yl | F | H |
| 269 | Me | H | 3-(phenylthio)-1H-indol-1-yl | F | F |
| 270 | Me | F | 3-(phenylthio)-1H-indol-1-yl | F | F |
| 271 | Me | dibenzylamino | H | H | H |
| 272 | Me | H | dibenzylamino | H | H |
| 273 | Me | H | H | dibenzylamino | H |
| 274 | Me | H | H | H | dibenzylamino |

FIGURE 3H

| No. | $R^{3a}$ | $R^{9a}$ | $R^{10a}$ | $R^{11a}$ | $R^{12a}$ |
|---|---|---|---|---|---|
| 275 | Me | F | dibenzylamino | H | H |
| 276 | Me | H | dibenzylamino | F | H |
| 277 | Me | H | dibenzylamino | H | F |
| 278 | Me | F | dibenzylamino | F | H |
| 279 | Me | H | dibenzylamino | F | F |
| 280 | Me | F | dibenzylamino | F | F |
| 281 | Me | -S(O)$_2$(4-Cl-Ph) | H | H | H |
| 282 | Me | H | -S(O)$_2$(4-Cl-Ph) | H | H |
| 283 | Me | H | H | -S(O)$_2$(4-Cl-Ph) | H |
| 284 | Me | H | H | H | -S(O)$_2$(4-Cl-Ph) |
| 285 | Me | F | -S(O)$_2$(4-Cl-Ph) | H | H |
| 286 | Me | H | -S(O)$_2$(4-Cl-Ph) | F | H |
| 287 | Me | H | -S(O)$_2$(4-Cl-Ph) | H | F |
| 288 | Me | F | -S(O)$_2$(4-Cl-Ph) | F | H |
| 289 | Me | H | -S(O)$_2$(4-Cl-Ph) | F | F |
| 290 | Me | F | -S(O)$_2$(4-Cl-Ph) | F | F |
| 291 | Me | -S(4-pyridyl) | H | H | H |
| 292 | Me | H | -S(4-pyridyl) | H | H |
| 293 | Me | H | H | -S(4-pyridyl) | H |
| 294 | Me | H | H | H | -S(4-pyridyl) |
| 295 | Me | F | -S(4-pyridyl) | H | H |
| 296 | Me | H | -S(4-pyridyl) | F | H |
| 297 | Me | H | -S(4-pyridyl) | H | F |
| 298 | Me | F | -S(4-pyridyl) | F | H |
| 299 | Me | H | -S(4-pyridyl) | F | F |
| 300 | Me | F | -S(4-pyridyl) | F | F |
| 301 | Me | -NHCH$_2$Ph | H | H | H |
| 302 | Me | H | -NHCH$_2$Ph | H | H |
| 303 | Me | H | H | -NHCH$_2$Ph | H |
| 304 | Me | H | H | H | -NHCH$_2$Ph |
| 305 | Me | F | -NHCH$_2$Ph | H | H |
| 306 | Me | H | -NHCH$_2$Ph | F | H |
| 307 | Me | H | -NHCH$_2$Ph | H | F |
| 308 | Me | F | -NHCH$_2$Ph | F | H |
| 309 | Me | H | -NHCH$_2$Ph | F | F |
| 310 | Me | F | -NHCH$_2$Ph | F | F |

BORON-CONTAINING SMALL MOLECULES AS ANTI-INFLAMMATORY AGENTS

CROSS-REFERENCE TO RELATED APPLICATIONS

This application claims priority to U.S. Provisional Patent Application Ser. Nos. 60/823,888 filed on Aug. 29, 2006 and 60/774,532 filed on Feb. 16, 2006, which are herein incorporated by reference in its entirety for all purposes.

BACKGROUND FOR THE INVENTION

Irregular inflammation is a major component of a wide range of human diseases. People suffering from degenerative disorders often exhibit excess levels of pro-inflammatory regulators in their blood. One type of such pro-inflammatory regulators are cytokines including IL-1$\alpha$, $\beta$, IL-2, IL-3, IL-6, IL-7, IL-9, IL-12, IL-17, IL-18, IL-23, TNF-$\alpha$, LT, LIF, Oncostatin, and IFNc1$\alpha$, $\beta$, $\gamma$.

A non-limiting list of common medical problems that are directly caused by inflammatory cytokines include: arthritis where inflammatory cytokines can lead to lesions in the synovial membrane and destruction of joint cartilage and bone; kidney failure where inflammatory cytokines restrict circulation and damage nephrons; lupus where inflammatory cytokines exacerbate immune complex deposition and damage; asthma where inflammatory cytokines close the airway; psoriasis where inflammatory cytokines induce dermatitis; pancreatitis where inflammatory cytokines induce pancreatic cell injury; allergy where inflammatory cytokines induce vasopermeability and congestion; fibrosis where inflammatory cytokines attack traumatized tissue; surgical complications where inflammatory cytokines prevent healing; anemia where inflammatory cytokines attack erythropoietin production; and fibromyalgia where inflammatory cytokines are elevated in fibromyalgia patients.

Other diseases associated with chronic inflammation include cancer; heart attack where chronic inflammation contributes to coronary atherosclerosis; Alzheimer's disease where chronic inflammation destroys brain cells; congestive heart failure where chronic inflammation causes heart muscle wasting; stroke where chronic inflammation promotes thrombo-embolic events; and aortic valve stenosis where chronic inflammation damages heart valves. Arteriosclerosis, osteoporosis, Parkinson's disease, infection, inflammatory bowel disease including Crohn's disease and ulcerative colitis as well as multiple sclerosis (a typical autoimmune inflammatory-related disease) are also related to inflammation (Bebo, B. F., Jr., *J Neurosci Res*, 45: 340-348, (1996); Mennicken, F., *Trends Pharmacol Sci*, 20: 73-78, (1999); Watanabe, T, *Int J Cardiol*, 66 Suppl 1: S45-53; discussion S55, (1998); Sullivan, G. W., *J Leukoc Biol*, 67: 591-602, (2000); Franceschi, C., Ann N Y Acad Sci, 908: 244-254, (2000); Rogers, J, Ann N Y Acad Sci, 924: 132-135, (2000); Li, Y. J., Hum Mol Genet, 12: 3259-3267, (2003); Maccarrone, M., *Curr Drug Targets Inflamm Allergy*, 1: 53-63, (2002); Lindsberg, P. J., *Stroke*, 34: 2518-2532, (2003); DeGraba, T. J., *Adv Neurol*, 92: 29-42, (2003); . Ito, H., *Curr Drug Targets Inflamm Allergy*, 2: 125-130, (2003); von der Thusen, J. H., *Pharmacol Rev*, 55: 133-166, (2003); Schmidt, M. I., *Clin Chem Lab Med*, 41: 1120-1130, (2003); Virdis, A., *Curr Opin Nephrol Hypertens*, 12: 181-187, (2003); Tracy, R. P., *Int J Clin Pract*, Suppl 10-17, (2003); Haugeberg, G., *Curr Opin Rheumatol*, 15: 469-475, (2003); Tanaka, Y., *J Bone Miner Metab*, 21: 61-66, (2003); Williams, J. D., *Clin Exp Dermatol*, 27: 585-590, (2002)). Some diseases in advanced stages can be life threatening. Several methodologies are available for the treatment of such inflammatory diseases; the results, however, are generally unsatisfactory as evidenced by a lack of efficacy and drug related side effects associated therewith.

Inflammatory Bowel Disease

Inflammatory bowel disease (IBD) comprises Crohn's disease (CD) and ulcerative colitis (UC), both of which are idiopathic chronic diseases occurring with an increasing frequency in many parts of the world. In the United States, more than 600,000 are affected every year. IBD can involve either small bowel, large bowel, or both. CD can involve any part of the gastrointestinal tract, but most frequently involves the distal small bowel and colon. It either spares the rectum, or causes inflammation or infection with drainage around the rectum. UC usually causes ulcers in the lower part of the large intestine, often starting at the rectum. Symptoms vary but may include diarrhea, fever, and pain. Patients with prolonged UC are at an increased risk of developing colon cancer. There is currently no satisfactory treatment, as the cause for IBD remains unclear although infectious and immunologic mechanisms have been proposed. IBD treatments aim at controlling inflammatory symptoms, conventionally using corticosteroids, aminosalicylates and standard immunosuppressive agents such as azathioprine (6-mercaptopurine), methotrexate and ciclosporine. Of these, the only disease-modifying therapies are the immunosuppressive agents azathioprine and methotrexate, both of which have a slow onset of action and only a moderate efficacy. Long-term therapy may cause liver damage (fibrosis or cirrhosis) and bone marrow suppression. Also patients often become refractory to such treatment. Other therapeutic regimes merely address symptoms (Rutgeerts, P. A, *J Gastroenterol Hepatol*, 17 Suppl: S176-185 (2002); Rutgeerts, P., *Aliment Pharmacol Ther*, 17: 185-192 (2003)).

Psoriasis

Psoriasis is one of the most common immune-mediated chronic skin diseases that comes in different forms and varied levels of severity, affecting approximately 2% of the population or more than 4.5 million people in the United States of which 1.5 million are considered to have a moderate to severe form of the disease. Ten to thirty percent of patients with psoriasis also develop a form of arthritis—psoriatic arthritis, which damages the bone and connective tissue around the joints. Psoriasis appears as patches of raised red skin covered by a flaky white buildup. It may also have a pimple-ish (pustular psoriasis) or burned (erythrodermic) appearance. Psoriasis may also cause intense itching and burning. Patients suffer psychologically as well as physically. Several modalities are currently available for treatment of psoriasis, including topical treatment, phototherapy, and systemic applications. However, they are generally considered to be only disease suppressive and disease modifying; none of them are curative. Moreover, many treatments are either cosmetically undesirable, inconvenient for long-term use, or associated with significant toxicity.

With increased understanding of the biological properties of psoriasis over the past two decades, biologic therapies targeting the activity of T lymphocytes and cytokines responsible for the inflammatory nature of this disease have become available. Currently, drugs prescribed for psoriasis include TNF-$\alpha$ inhibitors initially used for rheumatoid arthritis (RA) treatment, ENBREL® (etanercept), REMICADE® (infliximab) and HUMIRA® (adalimumab), and T-cell inhibitor AMEVIVE® (alefacept) from Biogen approved in 2002 and RAPTIVA® (efalizumab) from Genentech/Xoma approved in 2003 (Weinberg, J. M., *J Drugs Dermatol*, 1: 303-310, (2002)). AMEVIVE ALEFACEPT® is an immunoglobulin fusion protein composed of the first extracellular domain of human LFA-3 fused to the hinge, C(H)2 and C(H)3 domains of human IgG(1). It inhibits T cell proliferation through NK cells (Cooper, J. C., *Eur J Immunol*, 33: 666-675, (2003)). RAPTIVA® is also known as anti-CD11a, a humanized monoclonal antibody which targets the T cell adhesion molecule, leukocyte function-associated antigen-1 (LFA-1). Prevention of LFA-1 binding to its ligand (ICAM-1, intercellular adhesion molecule-1) inhibits lymphocyte activation and migration, resulting in a decreased lymphocyte infiltration, thereby limiting the cascade of events eventually leading to the signs and symptoms of psoriasis (Cather, J. C., *Expert Opin Biol Ther*, 3: 361-370, (2003)). Potential side effects for current TNF-α inhibitors of the prior art, however, are severe, including development of lymphoma (Brown, S. L., *Arthritis Rheum*, 46: 3151-3158, (2002)), worsening congestive heart failure, resulting in a serious infection and sepsis, and exacerbations of multiple sclerosis and central nervous system problems (Weisman, M. H., *J Rheumatol Suppl*, 65: 33-38, (2002); Antoni, C., *Clin Exp Rheumatol*, 20: S152-157, (2002)). While side effects of the T-cell inhibitor of AMEVIVE®/RAPTIVA® may be more tolerable in psoriasis treatment, RAPTIVA® is an immunosuppressive agent. Immunosuppressive agents have the potential to increase the risk of infection, reactivate latent, chronic infections or increase the risk of cancer development.

Although many advances have been made in the understanding of the biological properties of psoriasis over the past two decades and an unconventional treatment for psoriasis has become available as described above, much of the suffering it produces is still not adequately addressed. A survey of over 40,000 American patients with psoriasis performed by the National Psoriasis Foundation in 1998 showed 79% of the younger patients felt frustrated by the ineffectiveness of their treatment. Of those with severe disease, 32% felt their treatment was not aggressive enough (Mendonca, C. O., *Pharmacol Ther*, 99: 133-147, (2003); Schon, M. P., *J Invest Dermatol*, 112: 405-410, (1999)).

Rheumatoid Arthritis

Rheumatoid arthritis (RA) represents another example of troublesome inflammatory disorders. It is a common chronic inflammatory-related disease characterized by chronic inflammation in the membrane lining (the synovium) of the joints and/or other internal organs. The inflammatory cells can also invade and damage bone and cartilage. The joint involved can lose its shape and alignment, resulting in loss of movement. Patients with RA have pain, stiffness, warmth, redness and swelling in the joint, and other systemic symptoms like fever, fatigue, and anemia. Approximately 1% of the population or 2.1 million in the U.S. are currently affected, of which more are women (1.5 million) than men (0.6 million). The pathology of RA is not fully understood although the cascade of improper immunological reactions has been postulated as a mechanism. Conventional treatment is unfortunately inefficient in RA (Bessis, N., *J Gene Med*, 4: 581-591, (2002)) (29). The disease does not respond completely to symptomatic medications including corticosteroids and non-steroidal anti-inflammatory drugs (NSAIDs) used since the 1950s. Also, these medications carry a risk of serious adverse effects. The therapeutic effects of the disease-modifying antirheumatic drugs (DMARDs) such as Methotrexate (MTX) are often inconsistent and short-lived.

A new class of biologic DMARDs (disease-modifying antirheumatic drugs) for the treatment of RA has recently been developed based on an understanding of the role of cytokines, TNF-α and IL-1, in the inflammatory process. The FDA has approved several such DMARDs including ENBREL® (etanercept) from Immunex/Amgen Inc. in 1998, REMICADE® (infliximab) from Centocor/Johnson & Johnson, HUMIRA® (adalimumab) from Abbott Laboratories Inc. in 2002, and KINERET® (anakinra) from Amgen in 2001. ENBREL® is a soluble TNF receptor (TNFR) recombinant protein. REMICADE® is a humanized mouse (chimeric) anti-TNF-α monoclonal antibody. HUMIRA® is a fully human anti-TNF monoclonal antibody created using phage display technology resulting in an antibody with human-derived heavy and light chain variable regions and human IgG1:k constant regions. All these 3 protein-based drugs target and bind to TNF-α to block the effects of TNF-α. KINERET® is a recombinant IL-1 receptor antagonist, which is similar to native human IL-1Ra, except for the addition of a single methionine residue at its amino terminus. KINERET® blocks the biologic activity of IL-1 by competitively inhibiting IL-1 binding to the IL-1 type I receptor (IL-1RI) and consequently reducing the pro-inflammatory effects of IL-1.

The treatment with these biologic DMARDs relieves symptoms, inhibits the progression of structural damage, and improves physical function in patients with moderate to severe active RA. The three marketed TNF-α blocking agents have similar efficacy when combined with MTX, a widely used DMARD, in the treatment of patients with RA (Hochberg, M. C., *Ann Rheum Dis*, 62 Suppl 2: ii13-16, (2003)). While providing significant efficacy and a good overall safety profile in the short and medium term in many patients with RA, these biologic treatments may create serious problems and long-term side effects, such as in the liver, and still need to be evaluated. There has been a disturbing association between the use of both of ENBREL® or REMICADE® and the development of lymphoma, (S. L., *Arthritis Rheum*, 46: 3151-3158, (2002)). As described above, several reports have shown that patients treated with ENBREL® or REMICADE® worsen their congestive heart failure and develop serious infection and sepsis, and increase exacerbations of multiple sclerosis and other central nervous system problems (Antoni, C., *Clin Exp Rheumatol*, 20: S152-157, (2002); Mendonca, C. O., *Pharmacol Ther*, 99: 133-147, (2003)).

Multiple Sclerosis

Multiple Sclerosis (MS) is an autoimmune disease diagnosed in 350,000 to 500,000 people in the United States. Multiple areas of inflammation and loss of myelin in the brain and spinal cord signify the disease. Patients with MS exhibit varied degrees of neurological impairment depending on the location and extent of the loss of the myelin. Common symptoms of MS include fatigue, weakness, spasticity, balance problems, bladder and bowel problems, numbness, vision loss, tremors and depression. Current treatment of MS only alleviates symptoms or delays the progression of disability, and several new treatments for MS including stem cell transplantation and gene therapy are conservatory (Fassas, A., *Blood Rev*, 17: 233-240, (2003); Furlan, R., *Curr Pharm Des*, 9: 2002-2008, (2003)). While anti-TNF antibodies have shown protective effects in experimental autoimmune encephalomyelitis (EAE), they aggravate the disease in MS patients, suggesting that inhibition of TNF-α alone is not sufficient (Ghezzi, P., *Neuroimmunomodulation*, 9: 178-182, (2001)).

Neurodegenerative Disorders

Alzheimer's disease (AD) and Parkinson's disease (PK) are the two most common neurodegenerative disorders. AD seriously affects a person's ability to carry out daily activities. It involves the parts of the brain that control thought, memory, and language. About 4 million Americans, usually after age 60, are estimated to suffer from AD.

PK is a progressive disorder of the central nervous system affecting over 1.5 million people in the United States. Clinically, the disease is characterized by a decrease in spontaneous movements, gait difficulty, postural instability, rigidity and tremor. PK is caused by the degeneration of the pigmented neurons in the substantia nigra of the brain, resulting in decreased dopamine availability. The causes of these neurodegenerative disorders are unknown and there is currently no cure for the disease.

Thus, novel approaches for the treatment of the above and other inflammatory-related diseases are needed. Although inflammatory-related disease mechanisms remain unclear and often vary from each other, dysfunction of the immune system caused by deregulation of cytokines has been demonstrated to play an important role in the initiation and progression of inflammation (Schon, M. P., *J Invest Dermatol,* 112: 405-410, (1999); Andreakos, E. T., *Cytokine Growth Factor Rev,* 13: 299-313, (2002); Najarian, D. J., *J Am Acad Dermatol,* 48: 805-821, (2003)).

Cytokines can be generally classified into 3 types: pro-inflammatory (IL-1α, β, IL-2, IL-3, IL-6, IL-7, IL-9, IL-12, IL-17, IL-18, IL-23, TNF-α, LT, LIF, Oncostatin, and IFNc1α, β, γ); anti-inflammatory (IL-4, IL-10, IL-11, W-13 and TGF-β); and chemokines (IL-8, Gro-α, MIP-1, MCP-1, ENA-78, and RANTES).

In many inflammatory conditions, pro-inflammatory cytokines, especially TNF-α, IL-1β, and IL-6, as well as anti-inflammatory cytokine IL-10 appear to play an important role in the pathogenesis of various inflammatory-related diseases and therefore may serve as potential therapeutic targets. For example, elevated levels of some pro-inflammatory cytokines (TNF-α, IFNγ, IL-1, IL-2, IL-6 and IL-12) and chemokines (IL-8, MCP-1 and RANTES) have been observed in several inflammatory-related diseases such as CD, psoriasis, RA, Grave's disease and Hashimoto's thyroiditis (Andreakos, E. T., *Cytokine Growth Factor Rev,* 13: 299-313, (2002)), which parallels an increase in soluble TNF receptors, IL-1 receptor antagonists and the anti-inflammatory cytokine IL-10 (Noguchi, M., *Gut,* 43: 203-209, (1998); Autschbach, F., *Am J Pathol,* 153: 121-130, (1998)). IL-10 has been shown to suppress elevated pro-inflammatory cytokine production both in vitro in LPMC cultures and in vivo in patients (Schreiber, S., *Gastroenterology,* 108: 1434-1444, (1995)). Positive response of CD patients treated with IL-10 demonstrates that there might also be an imbalance between the production of pro-inflammatory and anti-inflammatory cytokines in CD.

In summary, the approach of treating inflammatory-related diseases has undergone an evolutionary change in recent years in part as a consequence of growing concerns of the severity of these diseases and in part due to considerable progress in the understanding of the important role of cytokines in their immuno-pathogenesis. The majority of the efforts have been focused on targeting TNF-α and IL-1 (Baugh, J. A., *Curr Opin Drug Discov Devel,* 4: 635-650, (2001)), and several products (TNF-αinhibitors: infliximab, a monoclonal anti-TNF-α antibody; and etanercept, the p75 TNF-α receptor) are currently marketed or in clinical trials for the treatment of RA, psoriasis and IBD as mentioned above. Several other drug candidates or strategies targeting IL-1 (Gabay, C., *Curr Opin Investig Drugs,* 4: 593-597, (2003)), IL-6 or IL-11α are under development (Gabay, C., *Curr Opin Investig Drugs,* 4: 593-597, (2003); Palladino, M. A., *Nat Rev Drug Discov,* 2: 736-746, (2003); Girolomoni, G., *Curr Opin Investig Drugs,* 3: 1590-1595, (2002)). These biological treatments provide significant efficacy in the short and medium term in many patients with RA (Elliott, M. J., *Lancet,* 344: 1125-1127, (1994); Moreland, L. W., *N Engl J Med,* 3377: 141-147, (1997); Campion, G. V., *Arthritis Rheum,* 39: 1092-1101, (1996); Feldmann, M., *Nat Immunol,* 2: 771-773, (2001)). Although these drugs are well tolerated and have a good overall safety profile, there remains a need in the art for additional drugs which can inhibit pro-inflammatory cytokines or stimulate anti-inflammatory cytokines.

Based on this concept, we examined several types of small molecules to test their ability in the regulation of multiple cytokines and explored their potential clinical applications for the treatment of a variety of inflammatory-related diseases.

SUMMARY OF THE INVENTION

In a first aspect, the invention provides a method of treating or preventing an inflammatory-related disease in a human or an animal, said method comprising administering to the human or the animal a therapeutically effective amount of a compound described herein. In an exemplary embodiment, the compound is a member selected from C1-C100. In an exemplary embodiment, the compound has a structure according to Formula I:

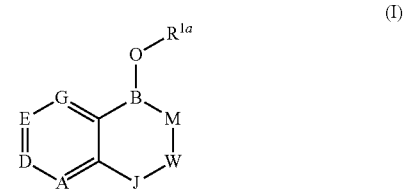

wherein B is boron. $R^{1a}$ is a member selected from a negative charge, a salt counterion, H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. M is a member selected from oxygen, sulfur and $NR^{2a}$. $R^{2a}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. J is a member selected from $(CR^{3a}R^{4a})_{n1}$ and $CR^{5a}$. $R^{3a}$, $R^{4a}$, and $R^{5a}$ are members independently selected from H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index n1 is an integer selected from 0 to 2. W is a member selected from C=O (carbonyl), $(CR^{6a}R^{7a})_{m1}$ and $CR^{8a}$. $R^{6a}$, $R^{7a}$, and $R^{8a}$ are members independently selected from H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index m1 is an integer selected from 0 and 1. A is a member selected from $CR^{9a}$ and N. D is a member selected from $CR^{10a}$ and N. E is a member selected from $CR^{11a}$ and N. G is a member selected from $CR^{12a}$ and N. $R^{9a}$, $R^{10a}$, $R^{11a}$ and $R^{12a}$ are members independently selected from H, OR*, NR*R**, SR*, —S(O) R*, —S(O)$_2$R*, —S(O)$_2$NR*R**, —C(O)R*, —C(O)OR*, —C(O)NR*R**, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Each R* and R** are members independently selected from H, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The combination of nitrogens (A+D+E+G) is an integer selected from 0 to 3. A member selected from $R^{3a}$, $R^{4a}$ and $R^{5a}$ and a member selected from $R^{6a}$, $R^{7a}$ and $R^{8a}$, together with the atoms to which they are attached, are optionally joined to form a 4 to 7 membered ring. $R^{3a}$ and $R^{4a}$, together with the atoms to which they are attached, are optionally joined to form a 4 to 7 membered ring. $R^{6a}$ and $R^{7a}$, together with the atoms to which they are attached, are optionally joined to form a 4 to 7 membered ring. $R^{9a}$ and $R^{10a}$, together with the atoms to which they are attached, are optionally joined to form a 4 to 7 membered ring. $R^{10a}$ and $R^{11a}$, together with the atoms to which they are attached, are optionally joined to form a 4 to 7 membered ring. $R^{11a}$ and $R^{12a}$, together with the atoms to which they are attached, are optionally joined to form a 4 to 7 membered ring.

In a second aspect, the invention provides a method of treating or preventing an inflammatory-related disease in a human or an animal, said method comprising administering to the human or the animal a therapeutically effective amount of a compound having a structure according to Formula II:

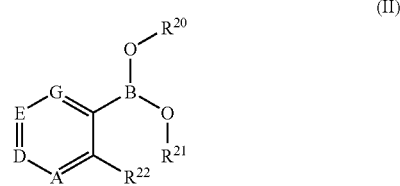

(II)

wherein B is boron. $R^{20}$, $R^{21}$ and $R^{22}$ are members independently selected from a negative charge, a salt counterion, H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. A is a member selected from $CR^{9a}$ and N. D is a member selected from $CR^{10a}$ and N. E is a member selected from $CR^{11a}$ and N. G is a member selected from $CR^{12a}$ and N. $R^{9a}$, $R^{10a}$, $R^{11a}$ and $R^{12a}$ are members independently selected from H, OR*, NR*R**, SR*, —S(O)R*, —S(O)$_2$R*, —S(O)$_2$NR*R**, —C(O)R*, —C(O)OR*, —C(O)NR*R**, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Each R* and R** are members independently selected from H, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The combination of nitrogens (A+D+E+G) is an integer selected from 0 to 3. A member selected from $R^{3a}$, $R^{4a}$ and $R^{5a}$ and a member selected from $R^{6a}$, $R^{7a}$ and $R^{8a}$, together with the atoms to which they are attached, are optionally joined to form a 4 to 7 membered ring. $R^{3a}$ and $R^{4a}$, together with the atoms to which they are attached, are optionally joined to form a 4 to 7 membered ring. $R^{6a}$ and $R^{7a}$, together with the atoms to which they are attached, are optionally joined to form a 4 to 7 membered ring. $R^{9a}$ and $R^{10a}$, together with the atoms to which they are attached, are optionally joined to form a 4 to 7 membered ring. $R^{10a}$ and $R^{11a}$, together with the atoms to which they are attached, are optionally joined to form a 4 to 7 membered ring. $R^{11a}$ and $R^{12a}$, together with the atoms to which they are attached, are optionally joined to form a 4 to 7 membered ring.

The invention also provides additional methods of using the compounds and pharmaceutical formulations of the compounds described herein.

BRIEF DESCRIPTION OF THE DRAWINGS

FIG. 3 displays exemplary compounds of the invention.

DETAILED DESCRIPTION OF THE INVENTION

I. Definitions and Abbreviations

Figure 1A:
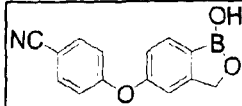
FIG. 1 describes the degree to which the compounds of the invention inhibited each of four cytokines: TNF-α, IL-β, IFN-γ, and IL-4.
Figure 1A:
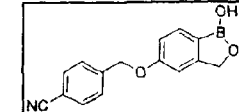
Figure 1A:
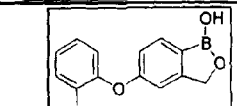
Figure 1A:
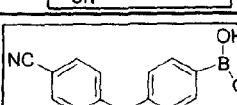
Figure 1A:
Figure 1A:
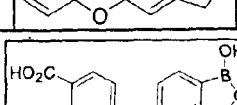
Figure 1A:
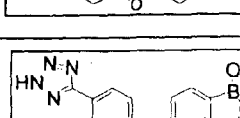
Figure 1A:
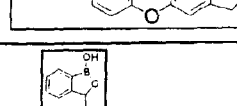
Figure 1A:
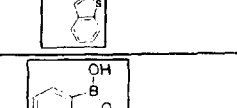
Figure 1A:
Figure 1A:
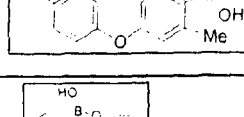
Figure 1B:
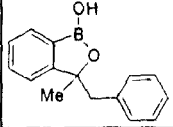
Figure 1B:
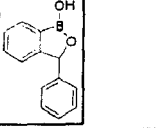
Figure 1B:
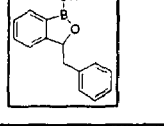
Figure 1B:
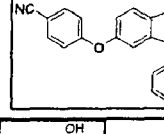
Figure 1B:
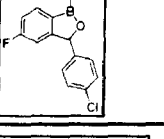
Figure 1B:
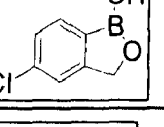
Figure 1B:
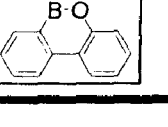

The abbreviations used herein generally have their conventional meaning within the chemical and biological arts.

"Compound of the invention," as used herein refers to the compounds discussed herein, pharmaceutically acceptable salts and prodrugs of these compounds.

"Inhibiting" and "blocking," are used interchangeably herein to refer to the partial or full blockade of the expression of a pro-inflammatory cytokine by a method of the invention, which leads to a decrease in the amount of the cytokine in the subject or patient.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "poly" as used herein means at least 2. For example, a polyvalent metal ion is a metal ion having a valency of at least 2.

"Moiety" refers to the radical of a molecule that is attached to another moiety.

The symbol ⌇, whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

"Ring" as used herein means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 to 7 atoms in the encircling arrangement. The ring optionally included a heteroatom. Thus, the term "5- to 7-membered ring" includes, for example pyridinyl and piperidinyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al) and boron (B).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of a active agent to provide the desired local or systemic effect. A "Topically effective," "Cosmetically effective," "pharmaceutically effective," or "therapeutically effective" amount refers to the amount of drug needed to effect the desired therapeutic result.

"Topically effective" refers to a material that, when applied to the skin, nail, hair, claw or hoof produces a desired pharmacological result either locally at the place of application or systemically as a result of transdermal passage of an active ingredient in the material.

"Cosmetically effective" refers to a material that, when applied to the skin, nail, hair, claw or hoof, produces a desired cosmetic result locally at the place of application of an active ingredient in the material.

The term "pharmaceutically acceptable salts" is meant to include salts of the compounds of the invention which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the present invention provides compounds which are in a prodrug form. Prodrugs of the compounds or complexes described herein readily undergo chemical changes under physiological conditions to provide the compounds of the present invention. Additionally, prodrugs can be converted to the compounds of the present invention by chemical or biochemical methods in an ex vivo environment.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium (3H), iodine-125 ($^{125}$I) or carbon-14 ($^{14}$C). All isotopic variations of the compounds of the present invention, whether radioactive or not, are intended to be encompassed within the scope of the present invention.

The term "pharmaceutically acceptable carrier" or "pharmaceutically acceptable vehicle" refers to any formulation or carrier medium that provides the appropriate delivery of an effective amount of a active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy*, 21st Ed., Lippincott, Williams & Wilkins (2005) which is incorporated herein by reference.

"Pharmaceutically acceptable topical carrier" and equivalent terms refer to pharmaceutically acceptable carriers, as described herein above, suitable for topical application. An inactive liquid or cream vehicle capable of suspending or dissolving the active agent(s), and having the properties of being nontoxic and non-inflammatory when applied to the skin, nail, hair, claw or hoof is an example of a pharmaceutically-acceptable topical carrier. This term is specifically intended to encompass carrier materials approved for use in topical cosmetics as well.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The terms "enhancement," "penetration enhancement" or "permeation enhancement" relate to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal or human skin, nail, hair, claw or hoof using a diffusion cell apparatus. A diffusion cell is described by Merritt et al. Diffusion Apparatus for Skin Penetration, *J of Controlled Release*, 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "excipients" is conventionally known to mean carriers, diluents and/or vehicles used in formulating drug compositions effective for the desired use.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to an broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

The term "transdermal delivery" refers to the diffusion of an agent across the barrier of the skin, nail, hair, claw or hoof resulting from topical administration or other application of a composition. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption or permeation through the remaining portion. Absorption through intact skin, nail, hair, claw or hoof can be enhanced by placing the active agent in an appropriate pharmaceutically acceptable vehicle before application to the skin, nail, hair, claw or hoof. Passive topical administration may consist of applying the active agent directly to the treatment site in combination with emollients or penetration enhancers. As used herein, transdermal delivery is intended to include delivery by permeation through or past the integument, i.e. skin, nail, hair, claw or hoof.

II. Introduction

The present invention is directed to methods of treating inflammatory-related diseases associated with pro-inflammatory cytokine expression and/or reduced anti-inflammatory expression. The methods of the present invention involve administering to a human or an animal in need of such treatment one or more compounds of the invention, either alone or as part of a pharmaceutical formulation. In a preferred embodiment, the compound being administered is in an amount sufficient to treat the inflammatory-related disease by inhibiting pro-inflammatory cytokine expression and/or by stimulating anti-inflammatory cytokines, but less than sufficient to substantially inhibit cyclin dependent kinases (CDKs).

III Compounds of Use in the Invention

In a first aspect, the invention provides a compound described herein. In an exemplary embodiment, the compound has a structure according to Formula I:

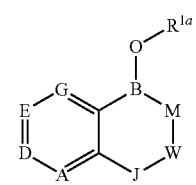

wherein B is boron. $R^{1a}$ is a member selected from a negative charge, a salt counterion, H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. M is a member selected from oxygen, sulfur and $NR^{2a}$. $R^{2a}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. J is a member selected from $(CR^{3a}R^{4a})_{n1}$ and $CR^{5a}$. $R^{3a}$, $R^{4a}$, and $R^{5a}$ are members independently selected from H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index n1 is an integer selected from 0 to 2. W is a member selected from C=O (carbonyl), $(CR^{6a}R^{7a})_{m1}$ and $CR^{8a}$. $R^{6a}$, $R^{7a}$, and $R^{8a}$ are members independently selected from H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index m1 is an integer selected from 0 and 1. A is a member selected from $CR^{9a}$ and N. D is a member selected from $CR^{10a}$ and N. E is a member selected from $CR^{11a}$ and N. G is a member selected from $CR^{12a}$ and N. $R^{9a}$, $R^{10a}$, $R^{11a}$ and $R^{12a}$ are members independently selected from H, OR*, NR*R**, SR*, —S(O)R*, —S(O)$_2$R*, —S(O)$_2$NR*R**, —C(O)R*, —C(O)OR*, —C(O)NR*R**, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Each R* and R** are members independently selected from H, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The combination of nitrogens (A+D+E+G) is an integer selected from 0 to 3. A member selected from $R^{3a}$, $R^{4a}$ and $R^{5a}$ and a member selected from $R^{6a}$, $R^{7a}$ and $R^{8a}$, together with the atoms to which they are attached, are optionally joined to form a 4 to 7 membered ring. $R^{3a}$ and $R^{4a}$, together with the atoms to which they are attached, are optionally joined to form a 4 to 7 membered ring. $R^{6a}$ and $R^{7a}$, together with the atoms to which they are attached, are optionally joined to form a 4 to 7 membered ring. $R^{9a}$ and $R^{10a}$, together with the atoms to which they are attached, are optionally joined to form a 4 to 7 membered ring. $R^{10a}$ and $R^{11a}$, together with the atoms to which they are attached, are optionally joined to form a 4 to 7 membered ring. $R^{11a}$ and $R^{12a}$, together with the atoms to which they are attached, are optionally joined to form a 4 to 7 membered ring.

In an exemplary embodiment, the compound has a structure according to Formula (Ia):

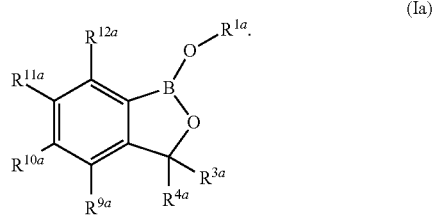

(Ia)

In another exemplary embodiment, each $R^{3a}$ and $R^{4a}$ is a member independently selected from H, cyano, substituted or unsubstituted methyl, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted mercaptomethyl, substituted or unsubstituted mercaptoalkyl, substituted or unsubstituted aminomethyl, substituted or unsubstituted alkylaminomethyl, substituted or unsubstituted dialkylaminomethyl, substituted or unsubstituted arylaminomethyl, substituted or unsubstituted indolyl and substituted or unsubstituted amido. In another exemplary embodiment, each $R^{3a}$ and $R^{4a}$ is a member independently selected from cyano, substituted or unsubstituted methyl, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted mercaptomethyl, substituted or unsubstituted mercaptoalkyl, substituted or unsubstituted aminomethyl, substituted or unsubstituted alkylaminomethyl, substituted or unsubstituted dialkylaminomethyl, substituted or unsubstituted arylaminomethyl, substituted or unsubstituted indolyl, substituted or unsubstituted amido.

In another exemplary embodiment, each $R^{3a}$ and $R^{4a}$ is a member selected from H, substituted or unsubstituted methyl, substituted or unsubstituted ethyl, substituted or unsubstituted propyl, substituted or unsubstituted isopropyl, substituted or unsubstituted butyl, substituted or unsubstituted t-butyl, substituted or unsubstituted phenyl and substituted or unsubstituted benzyl. In another exemplary embodiment, $R^{3a}$ and $R^{4a}$ is a member selected from methyl, ethyl, propyl, isopropyl, butyl, t-butyl, phenyl and benzyl. In another exemplary embodiment, $R^{3a}$ is H and $R^{4a}$ is a member selected from methyl, ethyl, propyl, isopropyl, butyl, t-butyl, phenyl and benzyl. In another exemplary embodiment, $R^{3a}$ is H and $R^{4a}$H.

In another exemplary embodiment, each $R^{9a}$, $R^{10a}$, $R^{11a}$ and $R^{12a}$ is a member independently selected from H, OR*, NR*R**, SR*, —S(O)R*, —S(O)$_2$R*, —S(O)$_2$NR*R**, —C(O)R*, —C(O)OR*, —C(O)NR*R**, halogen, cyano, nitro, substituted or unsubstituted methoxy, substituted or unsubstituted methyl, substituted or unsubstituted ethoxy, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted phenyloxy, substituted or unsubstituted phenyl methoxy, substituted or unsubstituted thiophenyloxy, substituted or unsubstituted pyridinyloxy, substituted or unsubstituted pyrimidinyloxy, substituted or unsubstituted benzylfuran, substituted or unsubstituted methylthio, substituted or unsubstituted mercaptomethyl, substituted or unsubstituted mercaptoalkyl, substituted or unsubstituted phenylthio, substituted or unsubstituted thiophenylthio, substituted or unsubstituted phenyl methylthio, substituted or unsubstituted pyridinylthio, substituted or unsubstituted pyrimidinylthio, substituted or unsubstituted benzylthiofuranyl, substituted or unsubstituted phenylsulfonyl, substituted or unsubstituted benzylsulfonyl, substituted or unsubstituted phenylmethylsulfonyl, substituted or unsubstituted thiophenylsulfonyl, substituted or unsubstituted pyridinylsulfonyl, substituted or unsubstituted pyrimidinylsulfonyl, substituted or unsubstituted sulfonamidyl, substituted or unsubstituted phenylsulfinyl, substituted or unsubstituted benzylsulfinyl, substituted or unsubstituted phenylmethylsulfinyl, substituted or unsubstituted thiophenylsulfinyl, substituted or unsubstituted pyridinylsulfinyl, substituted or unsubstituted pyrimidinylsulfinyl, substituted or unsubstituted amino, substituted or unsubstituted alkylamino, substituted or unsubstituted dialkylamino, substituted or unsubstituted trifluoromethylamino, substituted or unsubstituted aminomethyl, substituted or unsubstituted alkylaminomethyl, substituted or unsubstituted dialkylaminomethyl, substituted or unsubstituted arylaminomethyl, substituted or unsubstituted benzylamino, substituted or unsubstituted phenylamino, substituted or unsubstituted thiophenylamino, substituted or unsubstituted pyridinylamino, substituted or unsubstituted pyrimidinylamino, substituted or unsubstituted indolyl, substituted or unsubstituted morpholino, substituted or unsubstituted alkylamido, substituted or unsubstituted arylamido, substituted or unsubstituted ureido, substituted or unsubstituted carbamoyl, and substituted or unsubstituted piperizinyl. In an exemplary embodiment, $R^{9a}$, $R^{10a}$, $R^{11a}$ and $R^{12a}$ are selected from the previous list of substituents with the exception of —C(O)R*, —C(O)OR*, —C(O)NR*R**.

In another exemplary embodiment, $R^{9a}$, $R^{10a}$, $R^{11a}$ and $R^{12a}$ are members independently selected from fluoro, chloro, bromo, nitro, cyano, amino, methyl, hydroxylmethyl, trifluoromethyl, methoxy, trifluoromethyoxy, ethyl, diethylcarbamoyl, pyridin-2-yl, pyridin-3-yl, pyridin-4-yl, pyrimidinyl, piperizino, piperizinyl, piperizinocarbonyl, piperizinylcarbonyl, carboxyl, 1-tetrazolyl, 1-ethoxycarbonylmethoxy, carboxymethoxy, thiophenyl, 3-(butylcarbonyl)phenylmethoxy, 1H-tetrazol-5-yl, 1-ethoxycarbonylmethyloxy-, 1-ethoxycarbonylmethyl-, 1-ethoxycarbonyl-, carboxymethoxy-, thiophen-2-yl, thiophen-2-ylthio-, thiophen-3-yl, thiophen-3-ylthio, 4-fluorophenylthio, butylcarbonylphenylmethoxy, butylcarbonylphenylmethyl, butylcarbonylmethyl, 1-(piperidin-1-yl)carbonyl)methyl, 1-(piperidin-1-yl)carbonyl)methoxy, 1-(piperidin-2-yl)carbonyl)methoxy, 1-(piperidin-3-yl)carbonyl)methoxy, 1-(4-(pyrimidin-2-yl)piperazin-1-yl)carbonyl)methoxy, 1-(4-(pyrimidin-2-yl)piperazin-1-yl)carbonyl)methyl, 1-(4-(pyrimidin-2-yl)piperazin-1-yl)carbonyl, 1-4-(pyrimidin-2-yl)piperazin-1-yl, 1-(4-(pyridin-2-yl)piperazin-1-yl)carbonyl), 1-(4-(pyridin-2-yl)piperazin-1-yl)carbonylmethyl, (1-(4-(pyridin-2-yl)piperazin-1-yl)carbonyl)-methoxy), 1-(4-(pyridin-2-yl)piperazin-1-yl, 1H-indol-1-yl, morpholino-, morpholinyl, morpholinocarbonyl, morpholinylcarbonyl, phenylureido, phenylcarbamoyl, acetamido, 3-(phenylthio)-1H-indol-1-yl, 3-(2-cyanoethylthio)-1H-indol-1-yl, benzylamino, 5-methoxy-3-(phenylthio)-1H-indol-1-yl, 5-methoxy-3-(2-cyanoethylthio)-1H-indol-1-yl)), 5-chloro-1H-indol-1-yl, 5-chloro-3-(2-cyanoethylthio)-1H -indol-1-yl)), dibenzylamino, benzylamino, 5-chloro-3-(phenylthio)-1H -indol-1-yl)), 4-(1H-tetrazol-5-yl)phenoxy, 4-(1H-tetrazol-5-yl)phenyl, 4-(1H-tetrazol-5-yl)phenylthio, 2-cyanophenoxy, 3-cyanophenoxy, 4-cyanophenoxy, 2-cyanophenylthio, 3-cyanophenylthio, 4-cyanophenylthio, 2-chlorophenoxy, 3-chlorophenoxy, 4-chlorophenoxy, 2-fluorophenoxy, 3-fluorophenoxy, 4-fluorophenoxy, 2-cyanobenzyloxy, 3-cyanobenzyloxy, 4-cyanobenzyloxy, 2-chlorobenzyloxy, 3-chlorobenzyloxy, 4-chlorobenzyloxy, 2-fluorobenzyloxy, 3-fluorobenzyloxy, 4-fluorobenzyloxy, unsubstituted phenyl, unsubstituted benzyl. In an exemplary embodiment, $R^{9a}$ is H and $R^{12a}$ is H.

In an exemplary embodiment, the compound according to Formula (I) or Formula (Ia) is a member selected from:

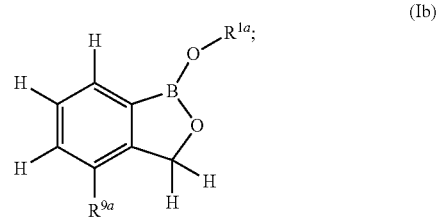
(Ib)

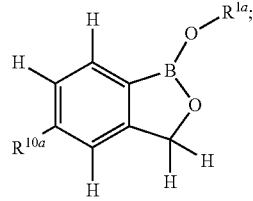
(Ic)

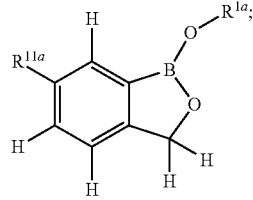
(Id)

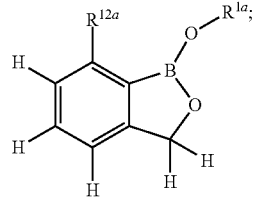
(Ie)

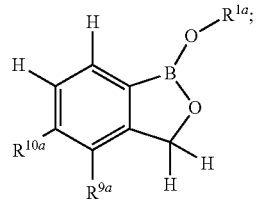
(If)

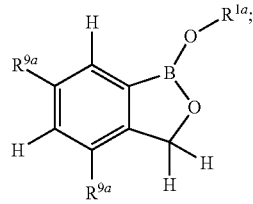
(Ig)

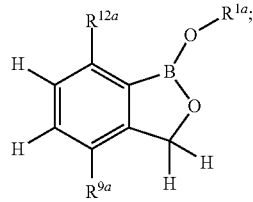
(Ih)

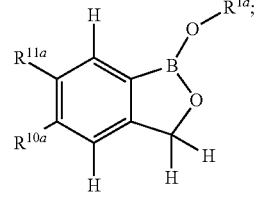
(Ii)

(Ij)

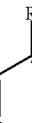
(Ik)

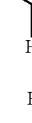
(Il)

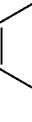
(Im)

(In)

(Io)

In an exemplary embodiment, the compound has a structure according to one of Formulae I-Io with substituent selections for $R^{9a}$, $R^{10a}$, $R^{11a}$ and $R^{12a}$ including all the possibilities contained in paragraph 69 except for H. In an exemplary embodiment, the compound has a structure according to one of Formulae Ib-Io with substituent selections for $R^{9a}$, $R^{10a}$, $R^{11a}$ and $R^{12a}$ including all the possibilities contained in paragraph 70 except for H.

In an exemplary embodiment, the compound has a formula according to Formulae (Ib)-(Ie) wherein $R^{1a}$ is a member selected from H, a negative charge and a salt counterion and the remaining R group ($R^{9a}$ in Ib, $R^{10a}$ in Ic, $R^{11a}$ in Id, and $R^{12a}$ in Ie) is a member selected from fluoro, chloro, bromo, nitro, cyano, amino, methyl, hydroxylmethyl, trifluoromethyl, methoxy, trifluoromethyoxy, ethyl, diethylcarbamoyl, pyridin-2-yl, pyridin-3-yl, pyridin-4-yl, pyrimidinyl, piperizino, piperizinyl, piperizinocarbonyl, piperizinylcarbonyl, carboxyl, 1-tetrazolyl, 1-ethoxycarbonylmethoxy, carboxymethoxy, thiophenyl, 3-(butylcarbonyl)phenylmethoxy, 1H-tetrazol-5-yl, 1-ethoxycarbonylmethyloxy-, 1-ethoxycarbonylmethyl-, 1-ethoxycarbonyl-, carboxymethoxy-, thiophen-2-yl, thiophen-2-ylthio-, thiophen-3-yl, thiophen-3-ylthio, 4-fluorophenylthio, butylcarbonylphenylmethoxy, butylcarbonylphenylmethyl, butylcarbonylmethyl, 1-(piperidin-1-yl)carbonyl)methyl, 1-(piperidin-1-yl)carbonyl)methoxy, 1-(piperidin-2-yl)carbonyl)methoxy, 1-(piperidin-3-yl)carbonyl)methoxy, 1-(4-(pyrimidin-2-yl)piperazin-1-yl)carbonyl)methoxy, 1-(4-(pyrimidin-2-yl)piperazin-1-yl)carbonyl)methyl, 1-(4-(pyrimidin-2-yl)piperazin-1-yl)carbonyl, 1-4-(pyrimidin-2-yl)piperazin-1-yl, 1-(4-(pyridin-2-yl)piperazin-1-yl)carbonyl), 1-(4-(pyridin-2-yl)piperazin-1-yl)carbonylmethyl, (1-(4-(pyridin-2-yl)piperazin-1-yl)carbonyl)-methoxy), 1-(4-(pyridin-2-yl)piperazin-1-yl, 1H-indol-1-yl, morpholino-, morpholinyl, morpholinocarbonyl, morpholinylcarbonyl, phenylureido, phenylcarbamoyl, acetamido, 3-(phenylthio)-1H-indol-1-yl, 3-(2-cyanoethylthio)-1H-indol-1-yl, benzylamino, 5-methoxy-3-(phenylthio)-1H-indol-1-yl, 5-methoxy-3-(2-cyanoethylthio)-1H-indol-1-yl)), 5-chloro-1H-indol-1-yl, 5-chloro-3-(2-cyanoethylthio)-1H-indol-1-yl)), dibenzylamino, benzylamino, 5-chloro-3-(phenylthio)-1H-indol-1-yl)), 4-(1H-tetrazol-5-yl)phenoxy, 4-(1H-tetrazol-5-yl)phenyl, 4-(1H-tetrazol-5-yl)phenylthio, 2-cyanophenoxy, 3-cyanophenoxy, 4-cyanophenoxy, 2-cyanophenylthio, 3-cyanophenylthio, 4-cyanophenylthio, 2-chlorophenoxy, 3-chlorophenoxy, 4-chlorophenoxy, 2-fluorophenoxy, 3-fluorophenoxy, 4-fluorophenoxy, 2-cyanobenzyloxy, 3-cyanobenzyloxy, 4-cyanobenzyloxy, 2-chlorobenzyloxy, 3-chlorobenzyloxy, 4-chlorobenzyloxy, 2-fluorobenzyloxy, 3-fluorobenzyloxy and 4-fluorobenzyloxy.

In an exemplary embodiment, the compound has a formula according to Formulae (If)-(Ik) wherein $R^{1a}$ is a member selected from H, a negative charge and a salt counterion and each of the remaining two R groups ($R^{9a}$ and $R^{10a}$ in If, $R^{9a}$ and $R^{11a}$ in Ig, $R^{9a}$ and $R^{12a}$ in Ih, $R^{10a}$ and $R^{11a}$ in Ii, $R^{10a}$ and $R^{12a}$ in Ij, $R^{11a}$ and $R^{12a}$ in Ik) is a member independently selected from fluoro, chloro, bromo, nitro, cyano, amino, methyl, hydroxylmethyl, trifluoromethyl, methoxy, trifluoromethyoxy, ethyl, diethylcarbamoyl, pyridin-2-yl, pyridin-3-yl, pyridin-4-yl, pyrimidinyl, piperizino, piperizinyl, piperizinocarbonyl, piperizinylcarbonyl, carboxyl, 1-tetrazolyl, 1-ethoxycarbonylmethoxy, carboxymethoxy, thiophenyl, 3-(butylcarbonyl)phenylmethoxy, 1H-tetrazol-5-yl, 1-ethoxycarbonylmethyloxy-, 1-ethoxycarbonylmethyl-, 1-ethoxycarbonyl-, carboxymethoxy-, thiophen-2-yl, thiophen-2-ylthio-, thiophen-3-yl, thiophen-3-ylthio, 4-fluorophenylthio, butylcarbonylphenylmethoxy, butylcarbonylphenylmethyl, butylcarbonylmethyl, 1-(piperidin-1-yl)carbonyl)methyl, 1-(piperidin-1-yl)carbonyl)methoxy, 1-(piperidin-2-yl)carbonyl)methoxy, 1-(piperidin-3-yl)carbonyl)methoxy, 1-(4-(pyrimidin-2-yl)piperazin-1-yl)carbonyl)methoxy, 1-(4-(pyrimidin-2-yl)piperazin-1-yl)carbonyl)methyl, 1-(4-(pyrimidin-2-yl)piperazin-1-yl)carbonyl, 1-4-(pyrimidin-2-yl)piperazin-1-yl, 1-(4-(pyridin-2-yl)piperazin-1-yl)carbonyl), 1-(4-(pyridin-2-yl)piperazin-1-yl)carbonylmethyl, (1-(4-(pyridin-2-yl)piperazin-1-yl)carbonyl)-methoxy), 1-(4-(pyridin-2-yl)piperazin-1-yl, 1H-indol-1-yl, morpholino-, morpholinyl, morpholinocarbonyl, morpholinylcarbonyl, phenylureido, phenylcarbamoyl, acetamido, 3-(phenylthio)-1H-indol-1-yl, 3-(2-cyanoethylthio)-1H-indol-1-yl, benzylamino, 5-methoxy-3-(phenylthio)-1H-indol-1-yl, 5-methoxy-3-(2-cyanoethylthio)-1H-indol-1-yl)), 5-chloro-1H-indol-1-yl, 5-chloro-3-(2-cyanoethylthio)-1H-indol-1-yl)), dibenzylamino, benzylamino, 5-chloro-3-(phenylthio)-1H-indol-1-yl)), 4-(1H-tetrazol-5-yl)phenoxy, 4-(1H-tetrazol-5-yl)phenyl, 4-(1H-tetrazol-5-yl)phenylthio, 2-cyanophenoxy, 3-cyanophenoxy, 4-cyanophenoxy, 2-cyanophenylthio, 3-cyanophenylthio, 4-cyanophenylthio, 2-chlorophenoxy, 3-chlorophenoxy, 4-chlorophenoxy, 2-fluorophenoxy, 3-fluorophenoxy, 4-fluorophenoxy, 2-cyanobenzyloxy, 3-cyanobenzyloxy, 4-cyanobenzyloxy, 2-chlorobenzyloxy, 3-chlorobenzyloxy, 4-chlorobenzyloxy, 2-fluorobenzyloxy, 3-fluorobenzyloxy, and 4-fluorobenzyloxy.

In an exemplary embodiment, the compound has a formula according to Formulae (Il)-(Io) wherein $R^{1a}$ is a member selected from H, a negative charge and a salt counterion and each of the remaining three R groups ($R^{9a}$, $R^{10a}$, $R^{11a}$ in (Il), $R^{9a}$, $R^{10a}$, $R^{12a}$ in (Im), $R^{9a}$, $R^{11a}$, $R^{12a}$ in (In), $R^{10a}$, $R^{11a}$, $R^{12a}$ in (Io)) is a member independently selected from fluoro, chloro, bromo, nitro, cyano, amino, methyl, hydroxylmethyl, trifluoromethyl, methoxy, trifluoromethyoxy, ethyl, diethylcarbamoyl, pyridin-2-yl, pyridin-3-yl, pyridin-4-yl, pyrimidinyl, piperizino, piperizinyl, piperizinocarbonyl, piperizinylcarbonyl, carboxyl, 1-tetrazolyl, 1-ethoxycarbonylmethoxy, carboxymethoxy, thiophenyl, 3-(butylcarbonyl)phenylmethoxy, 1H-tetrazol-5-yl, 1-ethoxycarbonylmethyloxy-, 1-ethoxycarbonylmethyl-, 1-ethoxycarbonyl-, carboxymethoxy-, thiophen-2-yl, thiophen-2-ylthio-, thiophen-3-yl, thiophen-3-ylthio, 4-fluorophenylthio, butylcarbonylphenylmethoxy, butylcarbonylphenylmethyl, butylcarbonylmethyl, 1-(piperidin-1-yl)carbonyl)methyl, 1-(piperidin-1-yl)carbonyl)methoxy, 1-(piperidin-2-yl)carbonyl)methoxy, 1-(piperidin-3-yl)carbonyl)methoxy, 1-(4-(pyrimidin-2-yl)piperazin-1-yl)carbonyl)methoxy, 1-(4-(pyrimidin-2-yl)piperazin-1-yl)carbonyl)methyl, 1-(4-(pyrimidin-2-yl)piperazin-1-yl)carbonyl, 1-4-(pyrimidin-2-yl)piperazin-1-yl, 1-(4-(pyridin-2-yl)piperazin-1-yl)carbonyl), 1-(4-(pyridin-2-yl)piperazin-1-yl)carbonylmethyl, (1-(4-(pyridin-2-yl)piperazin-1-yl)carbonyl)-methoxy), 1-(4-(pyridin-2-yl)piperazin-1-yl, 1H-indol-1-yl, morpholino-, morpholinyl, morpholinocarbonyl, morpholinylcarbonyl, phenylureido, phenylcarbamoyl, acetamido, 3-(phenylthio)-1H-indol-1-yl, 3-(2-cyanoethylthio)-1H-indol-1-yl, benzylamino, 5-methoxy-3-(phenylthio)-1H-indol-1-yl, 5-methoxy-3-(2-cyanoethylthio)-1H-indol-1-yl)), 5-chloro-1H-indol-1-yl, 5-chloro-3-(2-cyanoethylthio)-1H -indol-1-yl)), dibenzylamino, benzylamino, 5-chloro-3-(phenylthio)-1H -indol-1-yl)), 4-(1H-tetrazol-5-yl)phenoxy, 4-(1H-tetrazol-5-yl)phenyl, 4-(1H-tetrazol-5-yl)phenylthio, 2-cyanophenoxy, 3-cyanophenoxy, 4-cyanophenoxy, 2-cyanophenylthio, 3-cyanophenylthio, 4-cyanophenylthio, 2-chlorophenoxy, 3-chlorophenoxy, 4-chlorophenoxy, 2-fluorophenoxy, 3-fluorophenoxy, 4-fluorophenoxy, 2-cyanobenzyloxy, 3-cyanobenzyloxy, 4-cyanobenzyloxy, 2-chlorobenzyloxy, 3-chlorobenzyloxy, 4-chlorobenzyloxy, 2-fluorobenzyloxy, 3-fluorobenzyloxy, and 4-fluorobenzyloxy.

In an exemplary embodiment, the compound of the invention has a structure which is a member selected from:

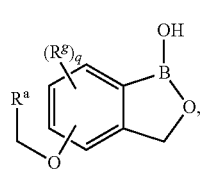
(Iab)

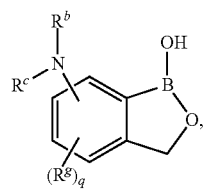
(Iac)

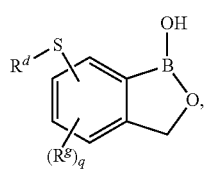
(Iad)

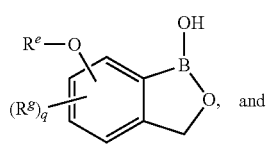
(Ia)

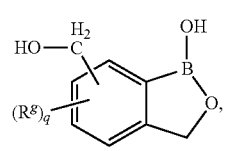
(Iaf)

in which q is a number between 0 and 1. $R^g$ is halogen. $R^a$, $R^b$, $R^c$, $R^d$ and $R^e$ are members independently selected from a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, there is a proviso that the compound is not a member selected from

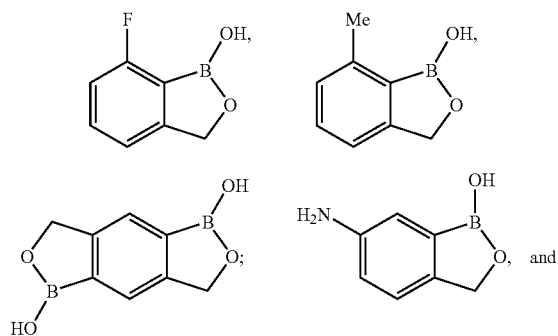

In an exemplary embodiment, the compound has a structure is a member selected from:

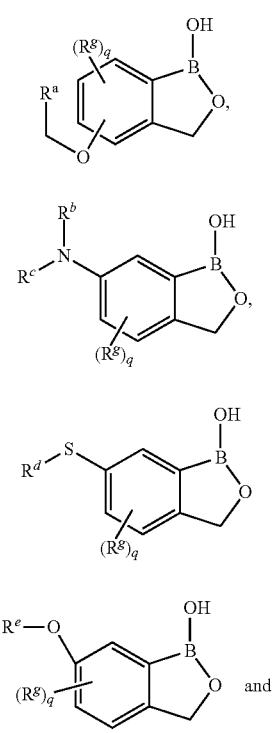
In an exemplary embodiment, $R^a$, $R^d$ and $R^e$ are each members independently selected from:
[structures shown]
In an exemplary embodiment, $R^b$ and $R^c$ are members independently selected from H, methyl,
[structures shown]

-continued

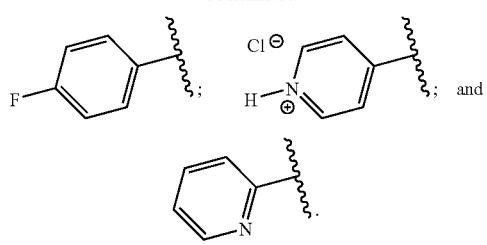

In another exemplary embodiment, $R^b$ is H and $R^c$ is a member selected from H, methyl,

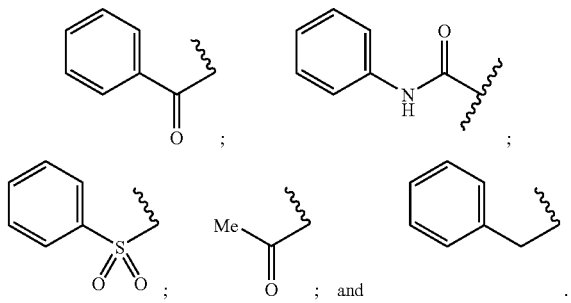

In another exemplary embodiment, $R^b$ and $R^c$ are, together with the nitrogen to which they are attached, optionally joined to form a member selected from

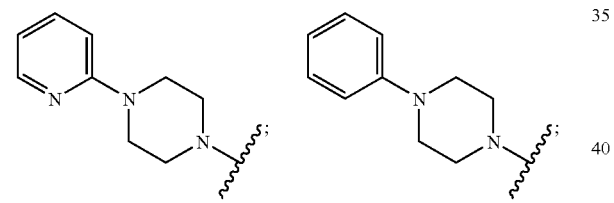

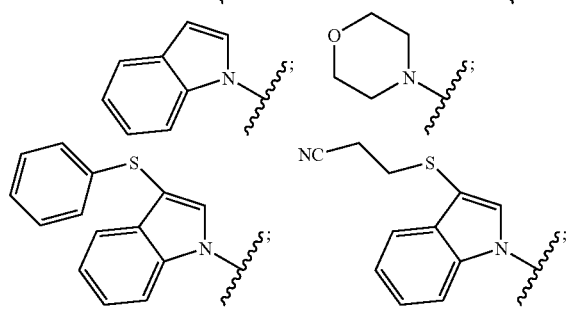

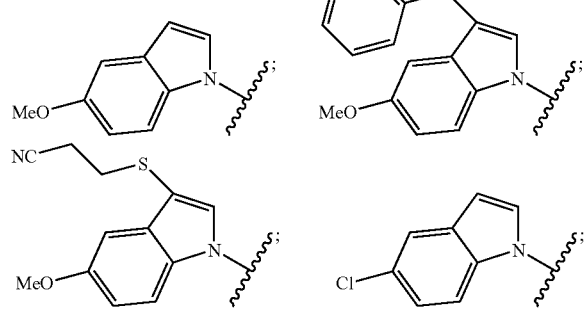

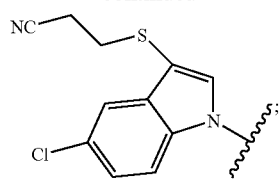

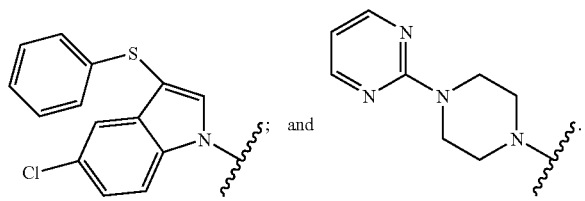

In an exemplary embodiment, $R^a$ is a member selected from

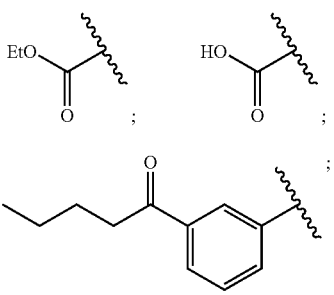

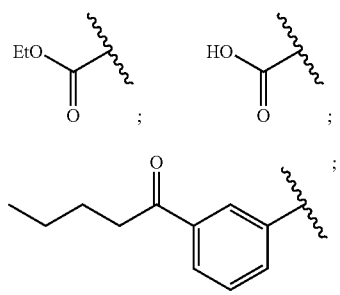

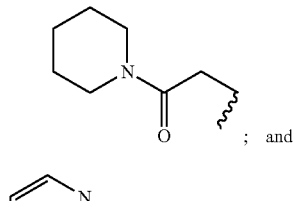

In an exemplary embodiment, $R^d$ is a member selected from

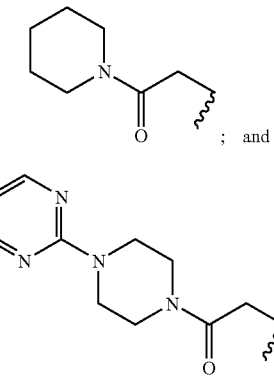

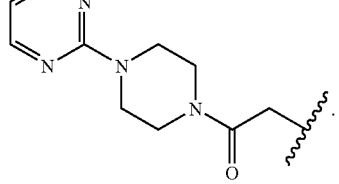

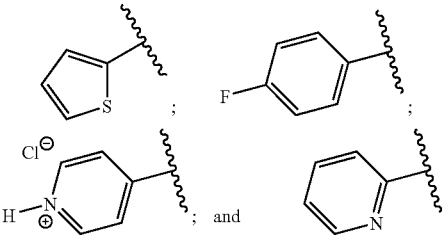

In an exemplary embodiment, $R^e$ is a member selected from

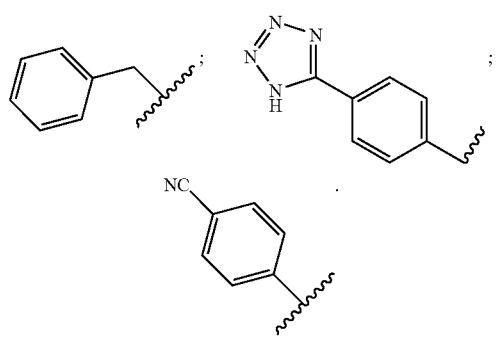
In an exemplary embodiment, the compound is a member selected from
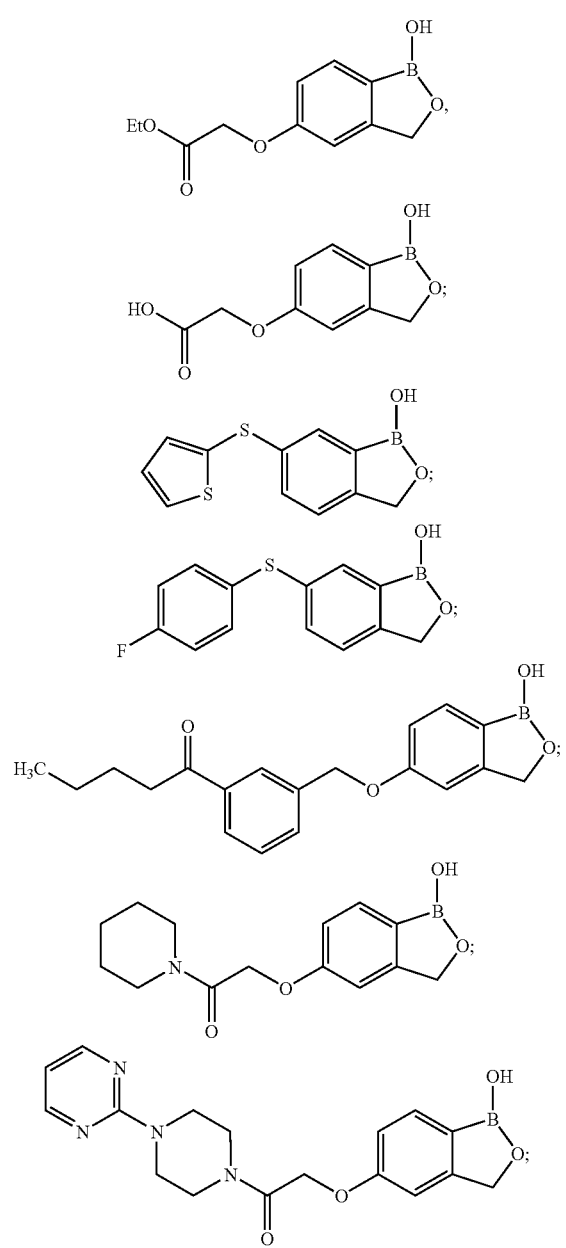
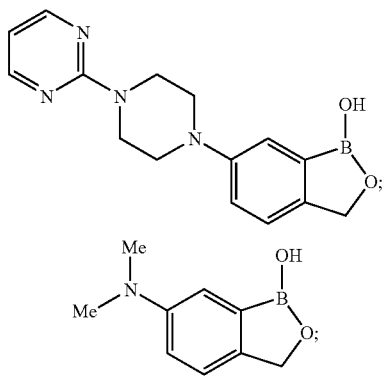
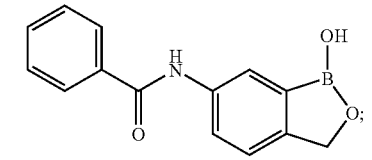
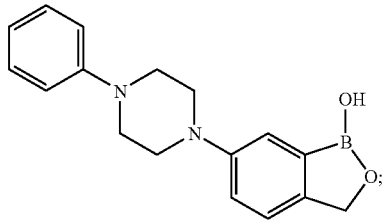
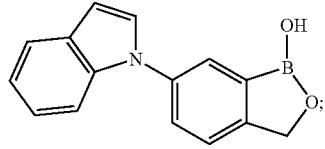
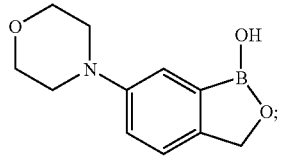
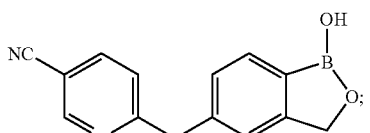
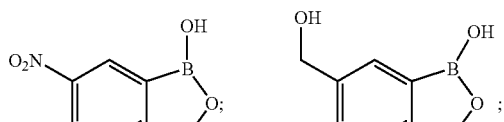
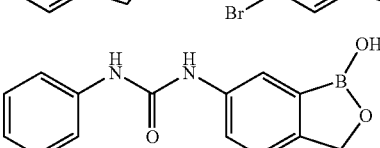
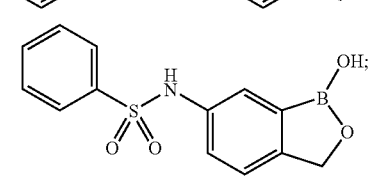

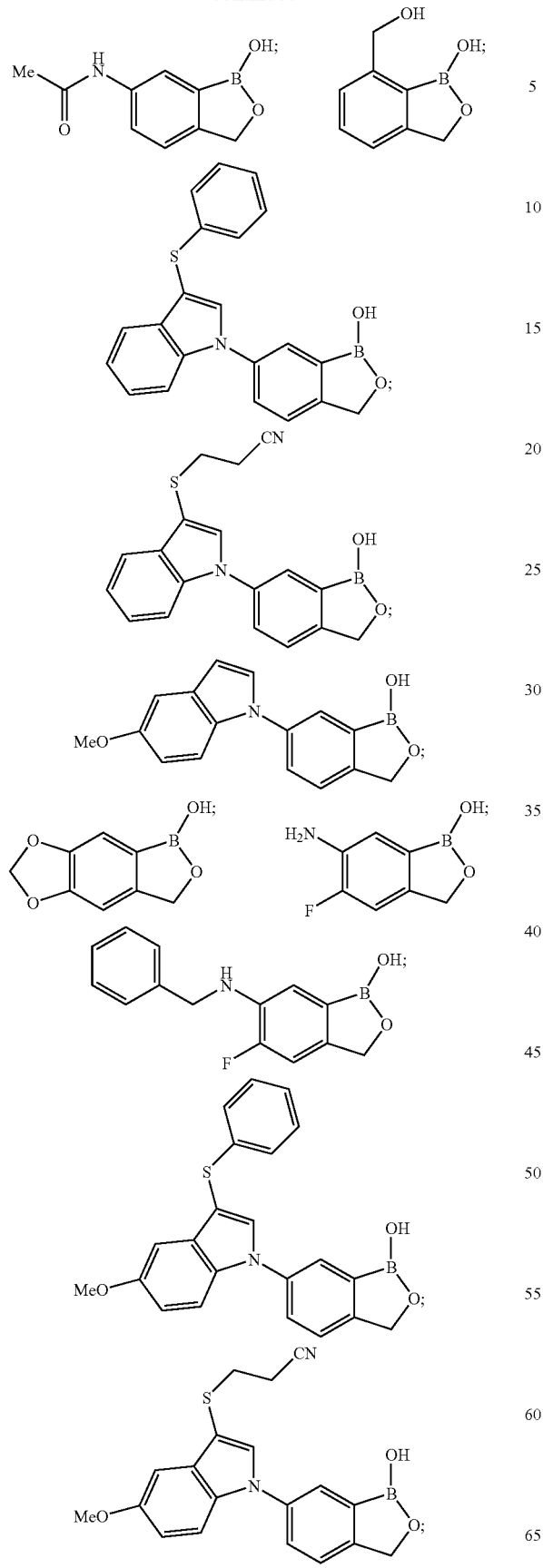
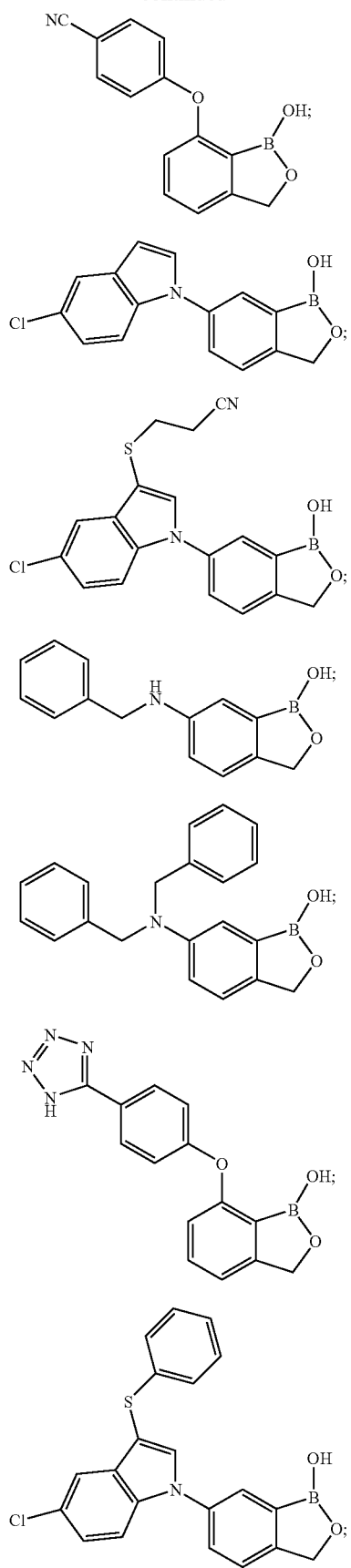

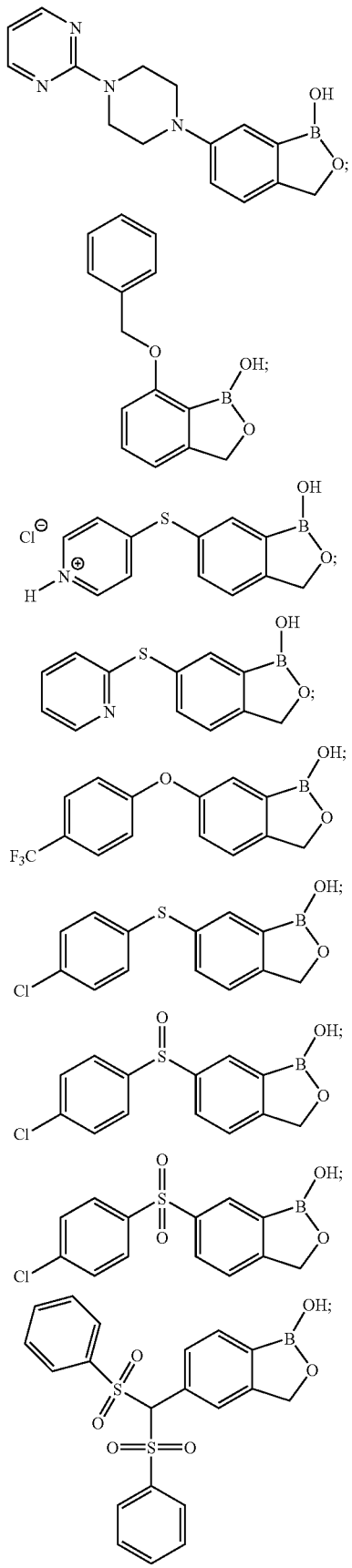

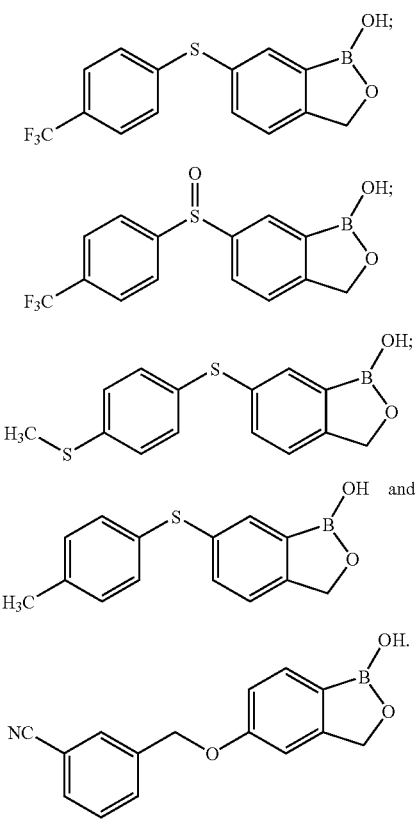

Figure 2A:
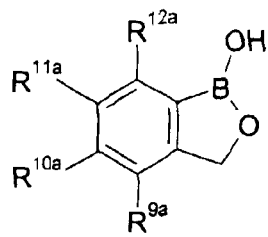
FIG. 2 displays exemplary compounds of the invention.

In an exemplary embodiment, the compound has a structure which is described in FIG. 2. In an exemplary embodiment, the compound has a structure which is described in FIG. 3.

In an exemplary embodiment, the compound has a structure according to a member selected from Formulae I(b), I(c), I(d), and I(e) wherein said remaining R group ($R^{9a}$ for I(b), $R^{10a}$ for I(c), $R^{11a}$ for I(d) and $R^{12a}$ for I(e)) is carboxymethoxy.

In an exemplary embodiment, the compound has a structure which is a member selected from Formulae (If)-(Ik), wherein either $R^{9a}$ or $R^{10a}$ for Formula (If), either $R^{9a}$ or $R^{11a}$ for Formula (Ig), either $R^{9a}$ or $R^{12a}$ for Formula (Ih), either $R^{10a}$ or $R^{11a}$ for Formula (Ii), either $R^{10a}$ or $R^{12a}$ for Formula (Ij), either $R^{11a}$ or $R^{12a}$ for Formula (Ik) is halogen, and the other substituent in the pairing (ex. if $R^{9a}$ is F in Formula (If), then $R^{10a}$ is selected from the following substituent listing), is a member selected from $NH_2$, $N(CH_3)H$, and $N(CH_3)_2$.

In another exemplary embodiment, the compound has a structure which is a member selected from:

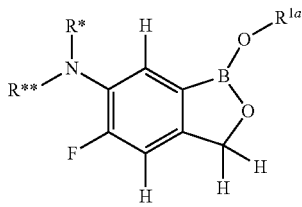

-continued

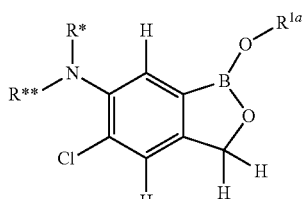

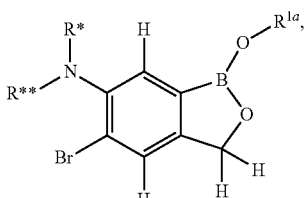

in which R* and R** are members selected from: H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, the compound is a member selected from

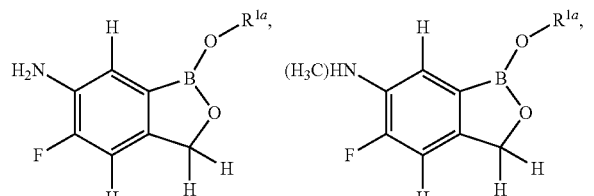

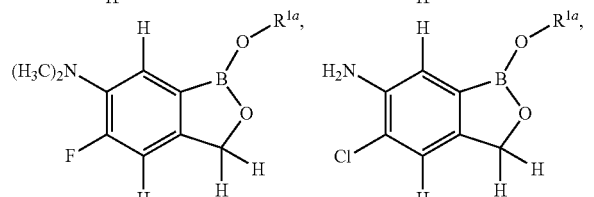

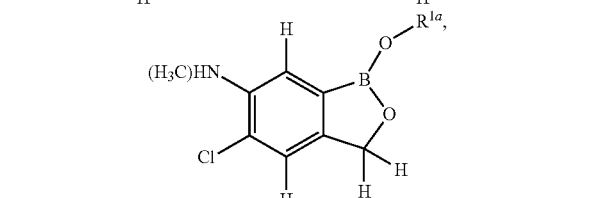

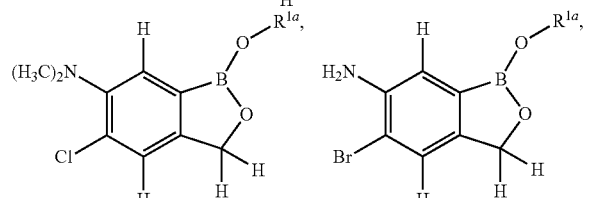

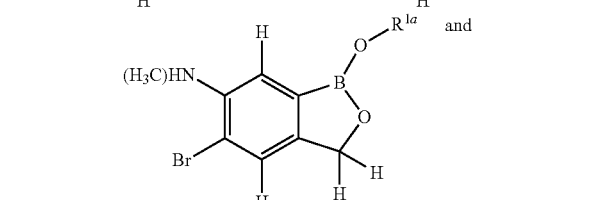

-continued

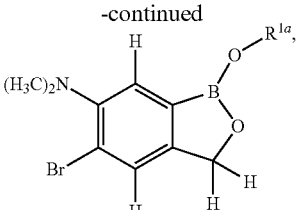

wherein $R^{1a}$ is a member selected from a negative charge, H and a salt counterion.

In another exemplary embodiment, the compound has a structure which is a member selected from:

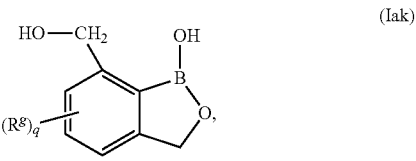

(Iak)

wherein q is 1 and $R^g$ is a member selected from fluoro, chloro and bromo.

In another exemplary embodiment, the compounds and embodiments described above in Formulae (I)-(Io) can form a hydrate with water, a solvate with an alcohol (e.g. methanol, ethanol, propanol); an adduct with an amino compound (e.g. ammonia, methylamine, ethylamine); an adduct with an acid (e.g. formic acid, acetic acid); complexes with ethanolamine, quinoline, amino acids, and the like.

In another exemplary embodiment, the compound has a structure according to Formula (Ip):

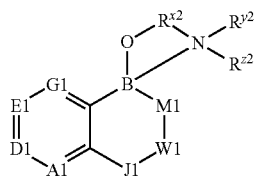

(Ip)

in which $R^{x2}$ is a member selected from substituted or unsubstituted $C_1$-$C_5$ alkyl and substituted or unsubstituted $C_1$-$C_5$ heteroalkyl. $R^{y2}$ and $R^{z2}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In another exemplary embodiment, the compound has a structure according to Formula (Iq):

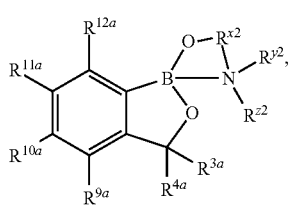

(Iq)

wherein B is boron. $R^{x2}$ is a member selected from substituted or unsubstituted $C_1$-$C_5$ alkyl and substituted or unsubstituted $C_1$-$C_5$ heteroalkyl. $R^{y2}$ and $R^{z2}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In another exemplary embodiment, at least one member selected from $R^{3a}$, $R^{4a}$, $R^{5a}$, $R^{6a}$, $R^{7a}$, $R^{8a}$, $R^{9a}$, $R^{10a}$, $R^{11a}$ and $R^{12a}$ is a member selected from nitro, cyano and halogen.

In another exemplary embodiment, the compound has a structure which is a member selected from the following Formulae:

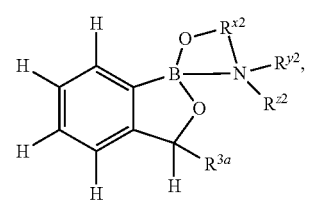
(Ir)

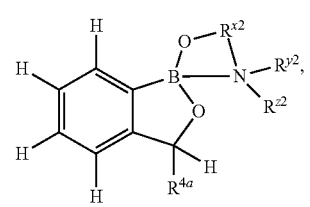
(Is)

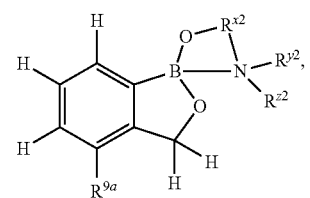
(It)

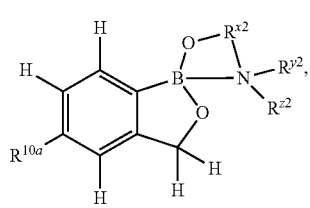
(Iu)

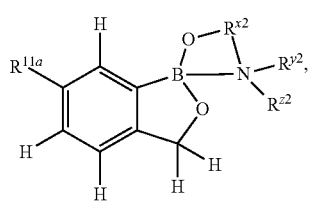
(Iv)

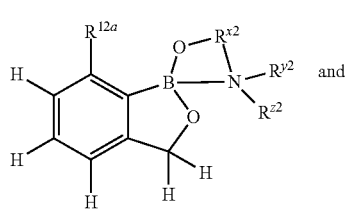
(Iw)

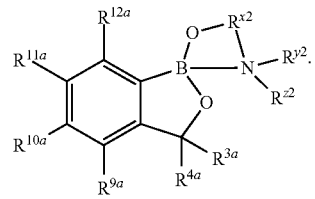
(Iz)

In another exemplary embodiment, the compound has a formula according to Formulae (Ib)-(Ie) wherein at least one member selected from $R^{3a}$, $R^{4a}$, $R^{5a}$, $R^{6a}$, $R^{7a}$, $R^{8a}$, $R^{9a}$, $R^{10a}$, $R^{11a}$ and $R^{12a}$ is a member selected from nitro, cyano, fluoro, chloro, bromo and cyanophenoxy. In another exemplary embodiment, the compound is a

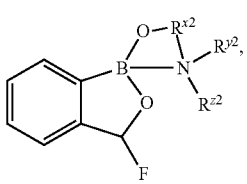 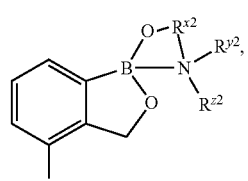

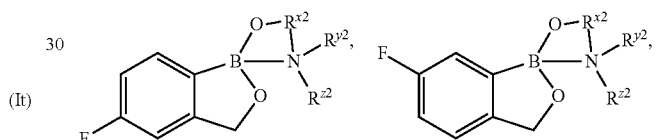

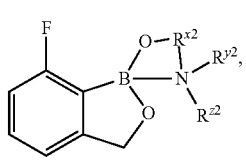

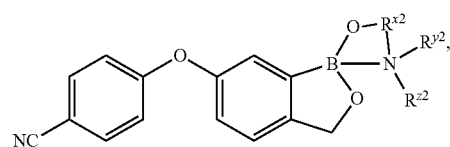

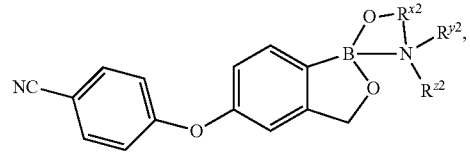

and

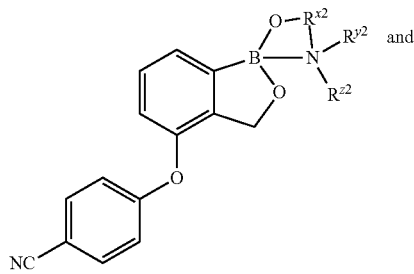

-continued

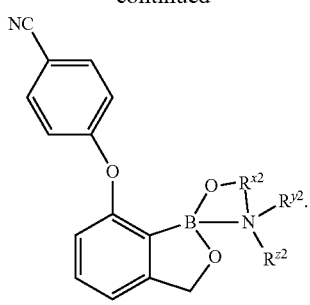

In another exemplary embodiment, the compound is a member selected from

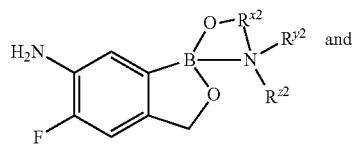

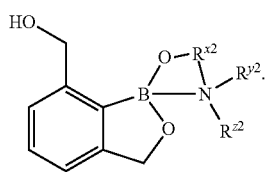

In another exemplary embodiment, the invention provides poly- or multi-valent species of the compounds of the invention. In an exemplary embodiment, the invention provides a dimer of the compounds described herein. In an exemplary embodiment, the invention provides a dimer of the compounds described herein. In an exemplary embodiment, the invention provides a dimer of a compound which is a member selected from C1-C100. In an exemplary embodiment the dimer is a member selected from

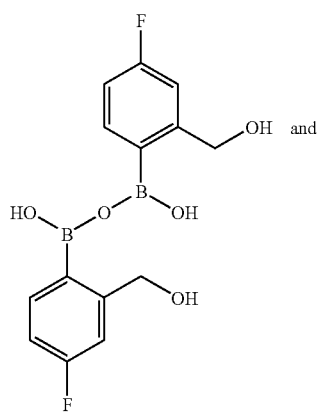

-continued

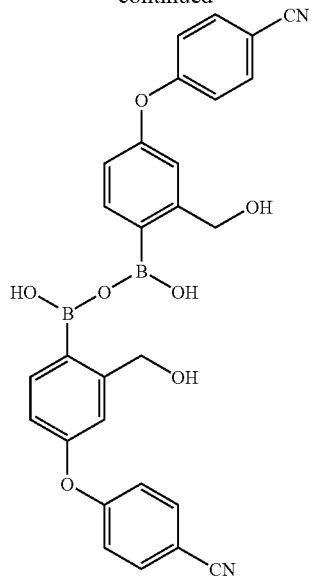

In an exemplary embodiment, the invention provides an anhydride of the compounds described herein. In an exemplary embodiment, the invention provides an anhydride of the compounds described herein. In an exemplary embodiment, the invention provides an anhydride of a compound which is a member selected from C1-C100. In an exemplary embodiment the anhydride is a member selected from

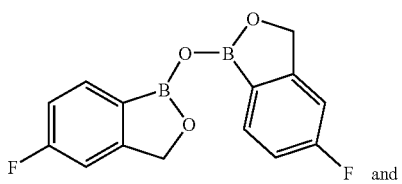

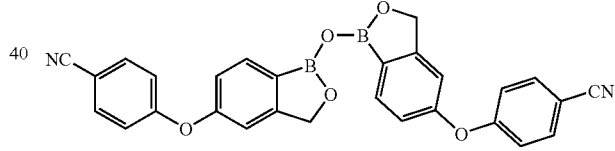

In an exemplary embodiment, the invention provides a trimer of the compounds described herein. In an exemplary embodiment, the invention provides a trimer of the compounds described herein. In an exemplary embodiment, the invention provides a trimer of a compound which is a member selected from C1-C100. In an exemplary embodiment the trimer is a member selected from

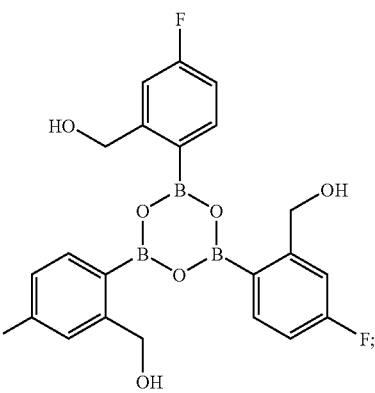

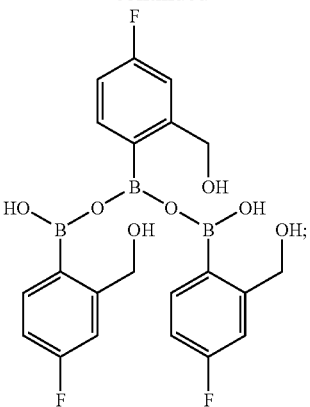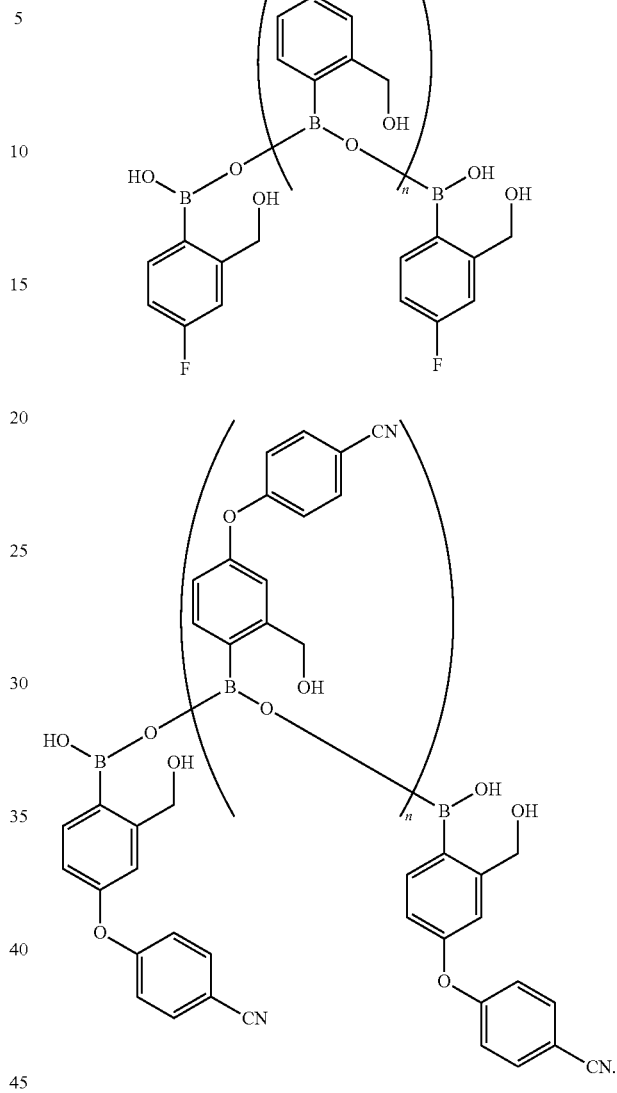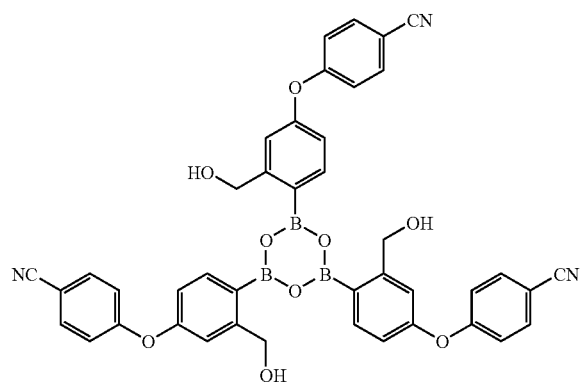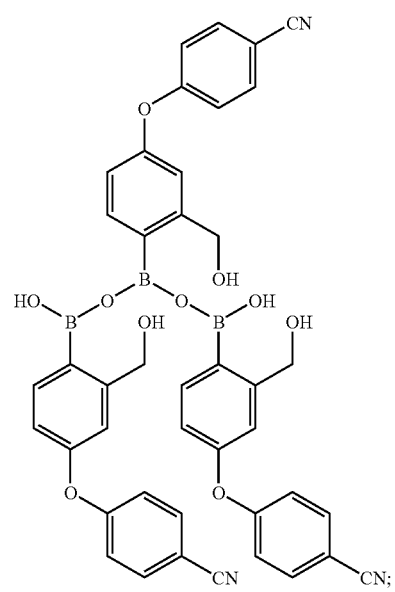
In another exemplary embodiment, the compound has a structure which is a member selected from:
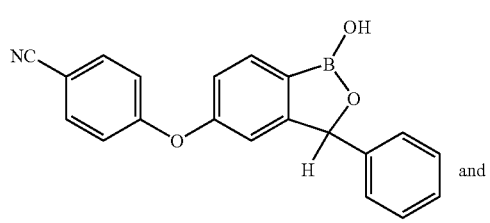 and
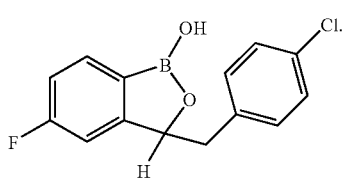

In another exemplary embodiment, the compound is

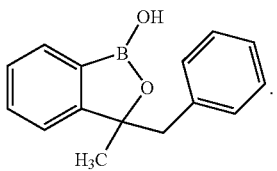

In another exemplary embodiment, the compound is a member selected from:

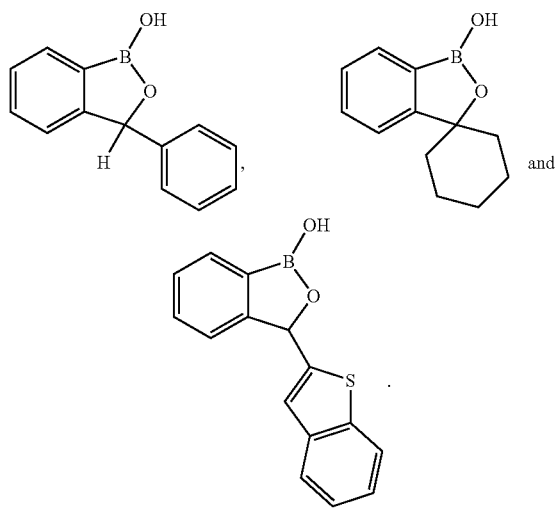

In another exemplary embodiment, the compound is a member selected from:

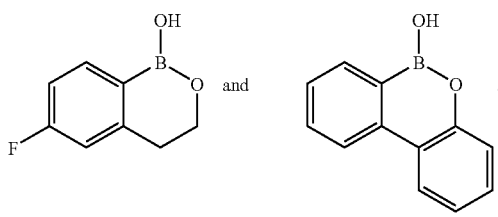

In another exemplary embodiment, $R^{1a}$ is H. In another exemplary embodiment, $R^{10a}$ and $R^{11a}$ are H. In another exemplary embodiment, one member selected from $R^{10a}$ and $R^{11a}$ is H and the other member selected from $R^{10a}$ and $R^{11a}$ is a member selected from halogen, methyl, cyano, methoxy, hydroxymethyl and p-cyanophenyloxy. In another exemplary embodiment, $R^{10a}$ and $R^{11a}$ are members independently selected from fluoro, chloro, methyl, cyano, methoxy, hydroxymethyl, and p-cyanophenyl.

Additional compounds which are useful in the methods of the invention are disclosed in U.S. Prov. Pat. App. 60/654,060; Filed Feb. 16, 2005; U.S. patent application Ser. No. 11/357,687, Filed Feb. 16, 2006; U.S. patent application Ser. No. 11/505,591, Filed Aug. 16, 2006, which are herein incorporated by reference in their entirety for all purposes. Methods of producing the compounds of the invention are also described in these patent applications.

IIIa. Compositions of Matter

The invention also provides novel compositions of matter. In an exemplary embodiment, the composition of matter is described herein. In another exemplary embodiment, the composition of matter has a structure according to Formula II:

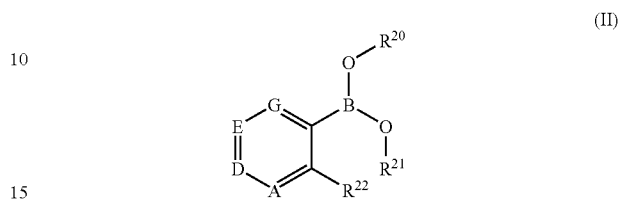

(II)

wherein B is boron. $R^{20}$, $R^{21}$ and $R^{22}$ are members independently selected from a negative charge, a salt counterion, H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. A is a member selected from $CR^{9a}$ and N. D is a member selected from $CR^{10a}$ and N. E is a member selected from $CR^{11a}$ and N. G is a member selected from $CR^{12a}$ and N. $R^{9a}$, $R^{10a}$, $R^{11a}$ and $R^{12a}$ are members independently selected from H, OR*, NR*R**, SR*, —S(O)R*, —S(O)$_2$R*, —S(O)$_2$NR*R**, —C(O)R*, —C(O)OR*, —C(O)NR*R**, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Each R* and R** are members independently selected from H, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The combination of nitrogens (A+D+E+G) is an integer selected from 0 to 3. $R^{9a}$ and $R^{10a}$, together with the atoms to which they are attached, are optionally joined to form a 4 to 7 membered ring. $R^{10a}$ and $R^{11a}$, together with the atoms to which they are attached, are optionally joined to form a 4 to 7 membered ring. $R^{11a}$ and $R^{12a}$, together with the atoms to which they are attached, are optionally joined to form a 4 to 7 membered ring.

In another exemplary embodiment, the compound has a structure according to Formula (IIa):

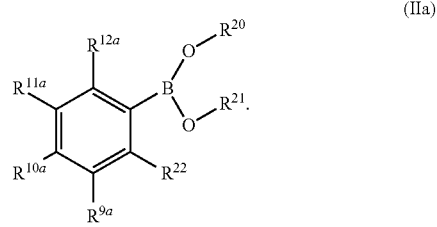

(IIa)

In another exemplary embodiment, the compound has a structure according to the following formula:

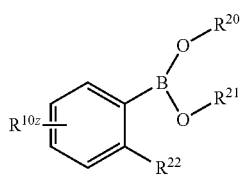

wherein $R^{10z}$ is a member selected from substituted or unsubstituted cyanophenoxy and substituted or unsubstituted cyanophenylthio and $R^{22}$ is a member selected from H, substituted or unsubstituted methyl, substituted or unsubstituted ethyl and substituted or unsubstituted propyl. In an exemplary embodiment, $R^{10z}$ is a member selected from para-cyanophenoxy and paracyanophenylthio. In an exemplary embodiment, $R^{20}$ and $R^{21}$ are members independently selected from a negative charge, a salt counterion and H.

In another exemplary embodiment, the compound has a structure which is a member selected from:

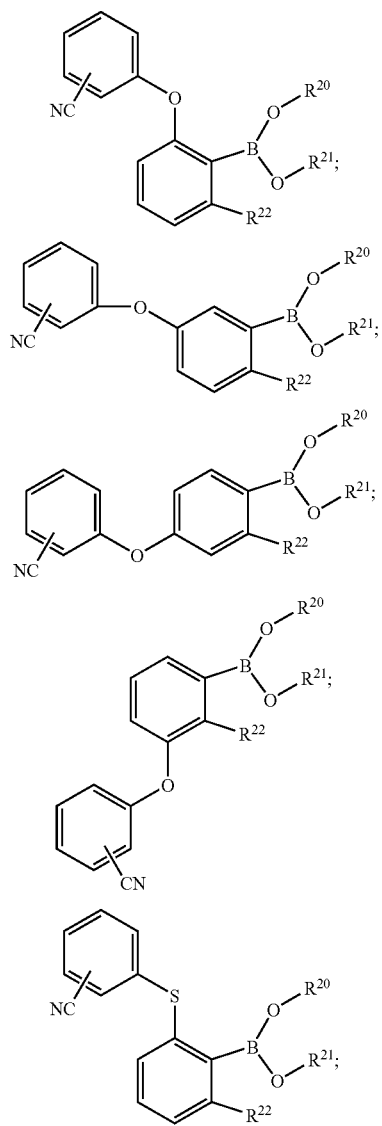

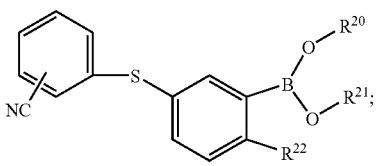

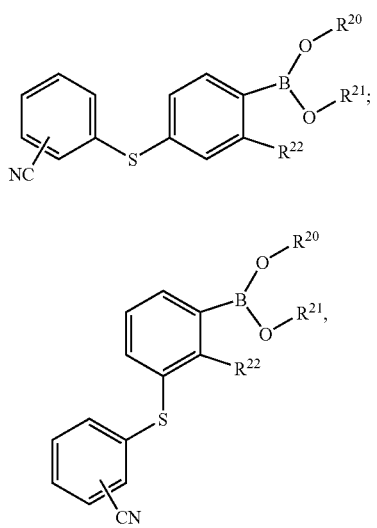

wherein $R^{22}$ is a member selected from H, substituted or unsubstituted methyl, substituted or unsubstituted ethyl and substituted or unsubstituted propyl. In an exemplary embodiment, $R^{20}$ and $R^{21}$ are members independently selected from a negative charge, a salt counterion and H.

In another exemplary embodiment, the compound has a structure which is a member selected from:

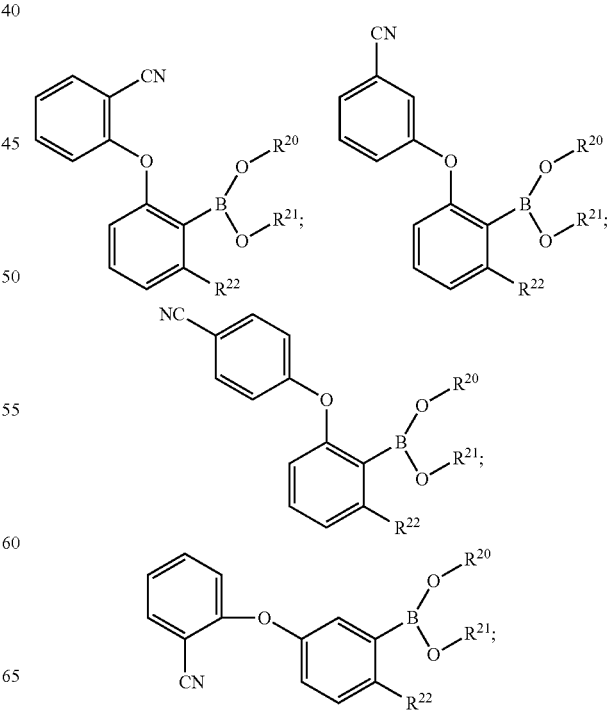

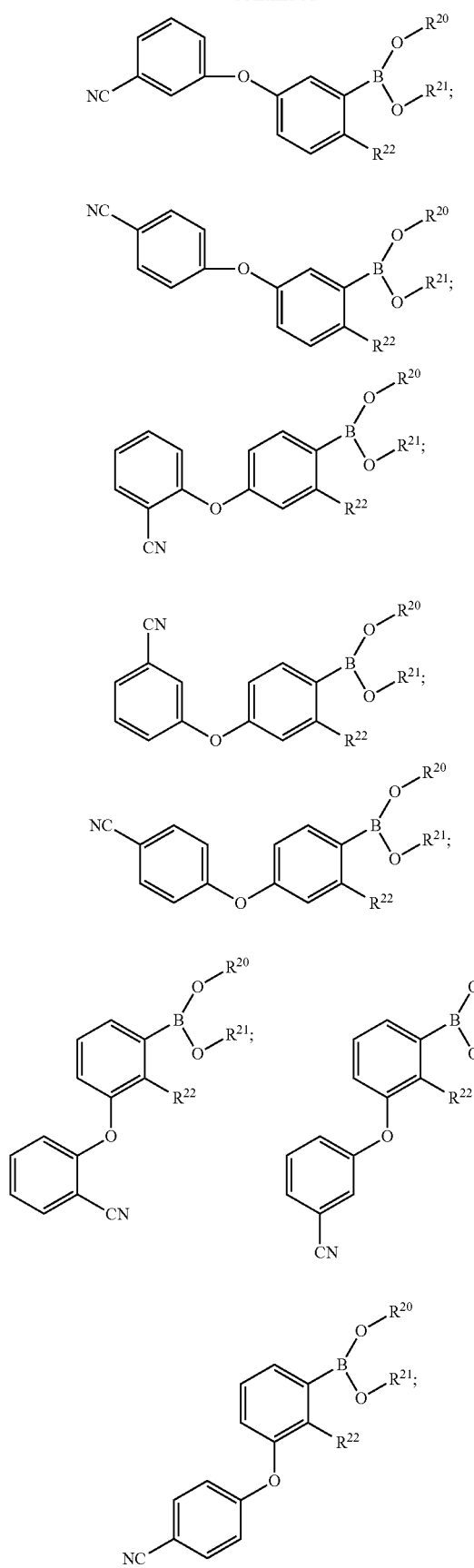
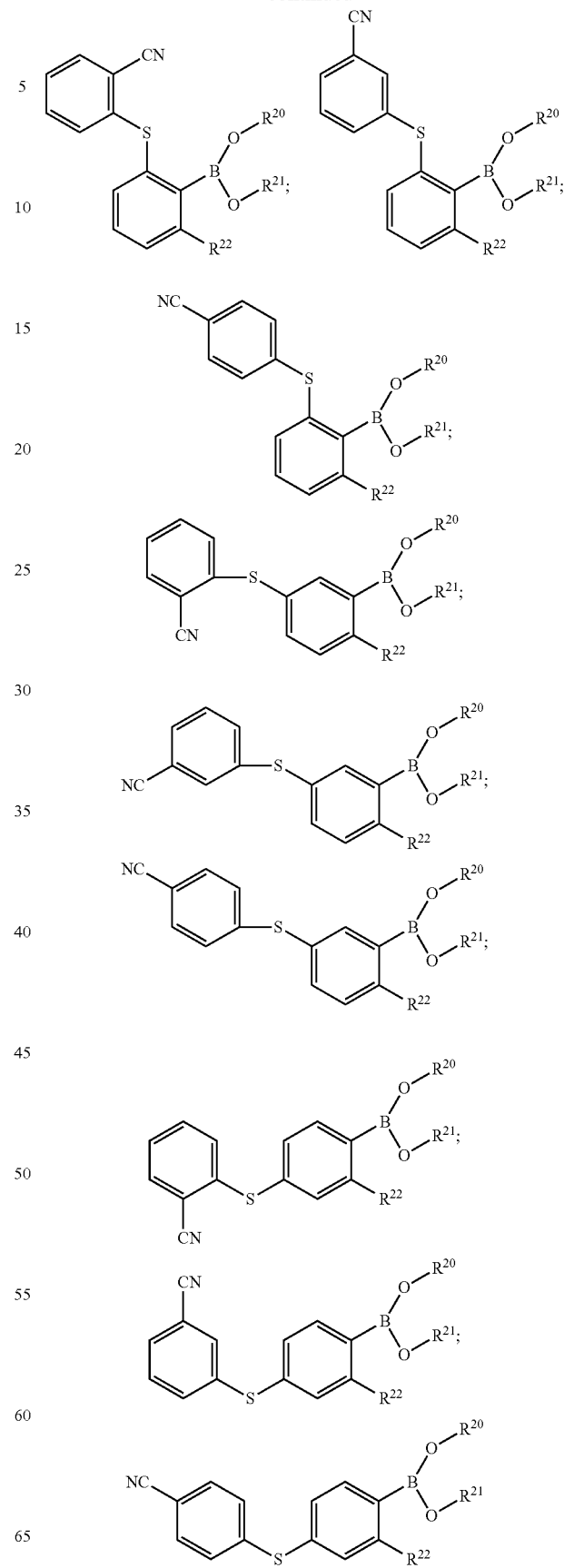

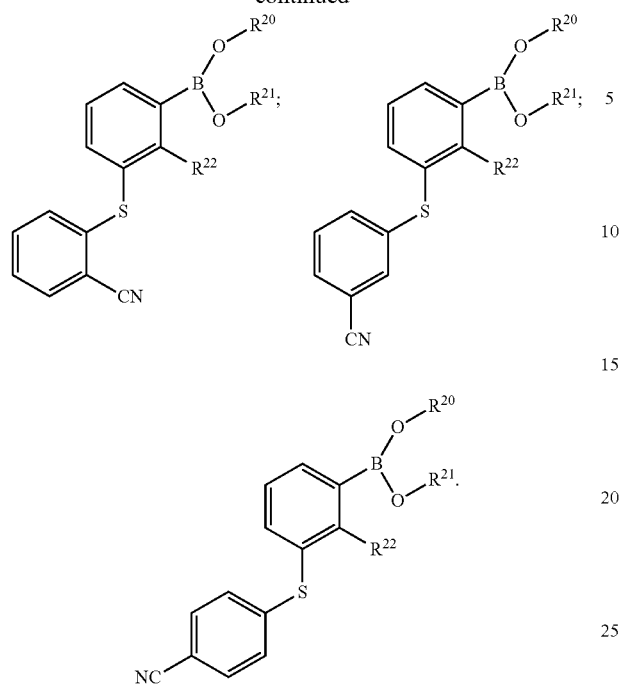

In an exemplary embodiment, $R^{22}$ is H. In an exemplary embodiment, $R^{22}$ is substituted or unsubstituted methyl. In an exemplary embodiment, $R^{22}$ is methyl. In an exemplary embodiment, $R^{20}$ and $R^{21}$ are members independently selected from a negative charge, a salt counterion and H.

In another exemplary embodiment, the compound has a structure which is a member selected from:

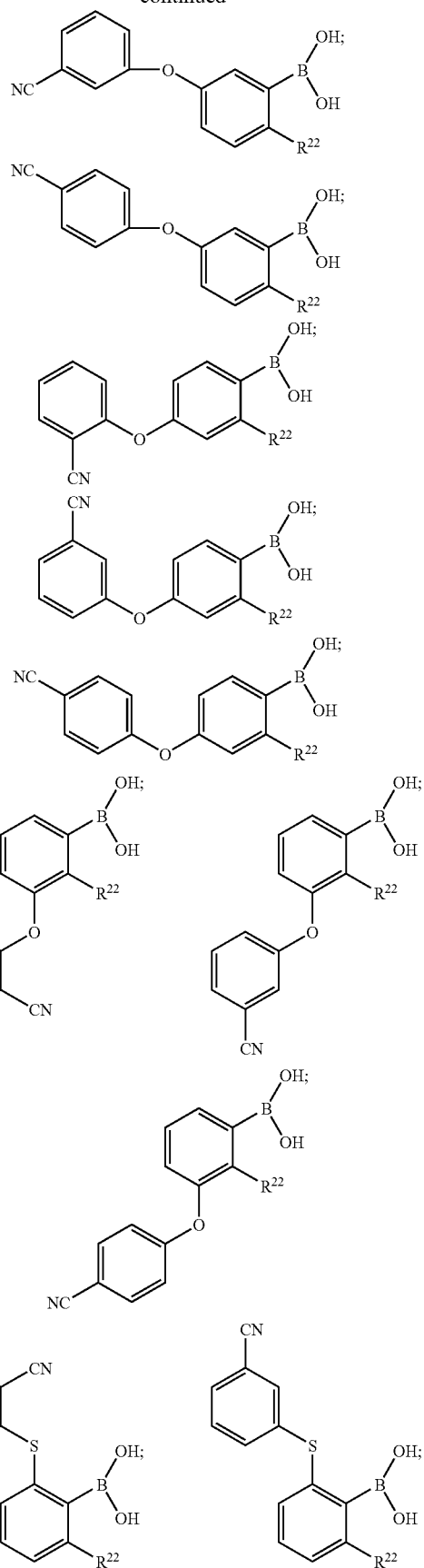

-continued

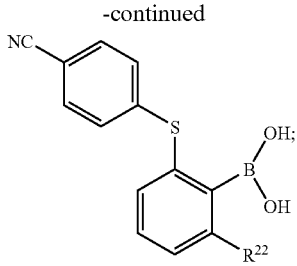
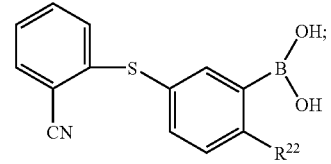
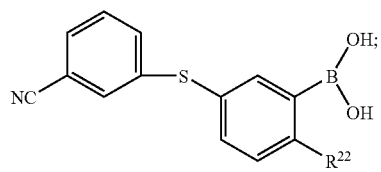
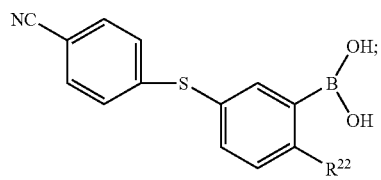
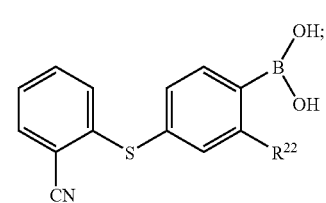
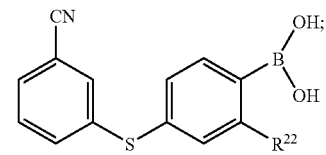
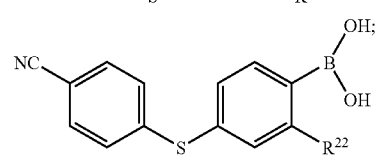
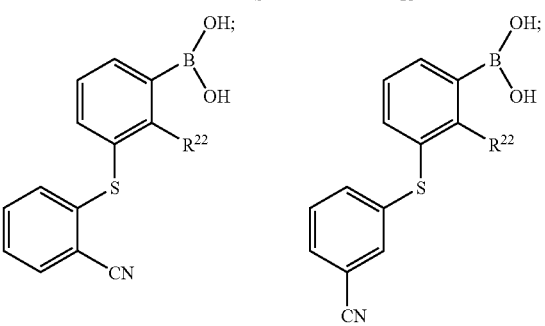

-continued

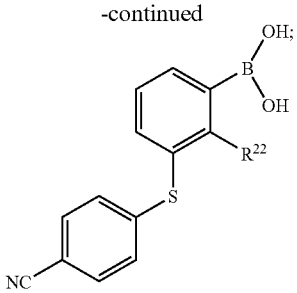

In an exemplary embodiment, $R^{22}$ is H. In an exemplary embodiment, $R^{22}$ is substituted or unsubstituted methyl. In an exemplary embodiment, $R^{22}$ is methyl.

In another exemplary embodiment, the compound is a member selected from:

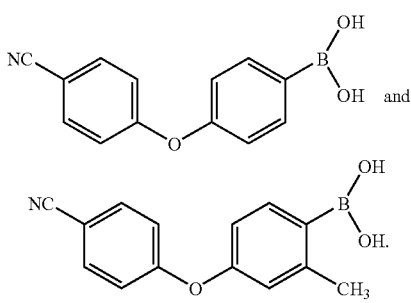

The compounds described herein can be synthesized by a similar route to that used in the synthesis of the oxaboroles (2) described herein. However, the synthesis of the phenylboronic acid and phenylbromide precursors is simplified by the absence of a protected ortho-hydroxymethyl group present on (1). Therefore, in many cases, a similar range of ortho-, meta- and para-substituted boronic acids (4) can be synthesized.

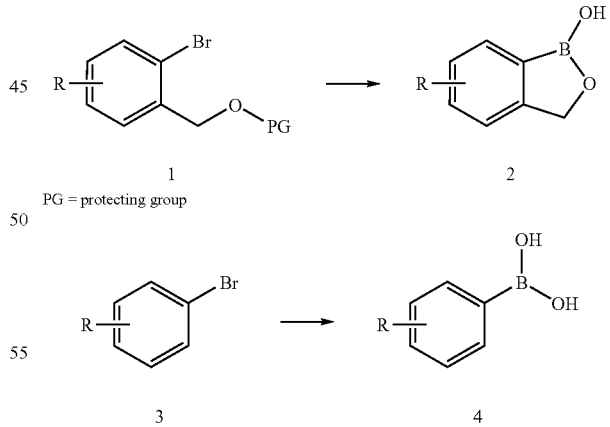

Examples of the production of these boronic acids are provided in the Examples section. Additionally, phenylthio derivatives can be synthesized by using the phenyloxy derivative protocols and substituting the phenolic reactant with its thiophenolic analog. For example, 4-(4-cyanophenylthio) phenylboronic acid can be synthesized using the protocol for 4-(4-cyanophenoxy)phenylboronic acid described herein and substituting 4-bromothiophenol for 4-bromophenol.

In another exemplary embodiment, the composition of matter described herein can be used in a method of the invention described herein. In another exemplary embodiment, the invention provides a method of treating or preventing an inflammatory-related disease in a human or an animal, said method comprising administering to the human or the animal a therapeutically effective amount of a compound described herein in section IIIa. In another exemplary embodiment, the compound has a structure according to Formula II or Formula IIa. In another exemplary embodiment, the compound has a structure which is a member selected from:

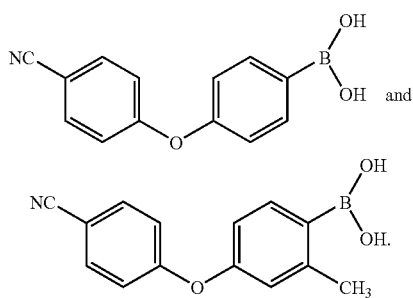

In another exemplary embodiment, the method further comprises administering said compound as part of a pharmaceutical formulation, said formulation further comprising a pharmaceutically acceptable excipient. In another exemplary embodiment, the compound described in section IIIa is in an amount sufficient to treat the inflammatory-related disease by inhibiting pro-inflammatory cytokine expression or by stimulating anti-inflammatory cytokine expression, but the amount is less than sufficient to substantially inhibit cyclin dependent kinases. In another exemplary embodiment, the disease is a member selected from arthritis, rheumatoid arthritis, an inflammatory bowel disease, psoriasis, multiple sclerosis, a neurodegenerative disorder, congestive heart failure, stroke, aortic valve stenosis, kidney failure, lupus, pancreatitis, allergy, fibrosis, anemia, atherosclerosis, a metabolic disease, a bone disease, a cardiovascular disease, a chemotherapy/radiation related complication, diabetes type I, diabetes type II, a liver disease, a gastrointestinal disorder, an ophthamological disease, allergic conjunctivitis, diabetic retinopathy, Sjogren's syndrome, uvetitis, a pulmonary disorder, a renal disease, dermatitis, HIV-related cachexia, cerebral malaria, ankylosing spondolytis, leprosy, anemia and fibromyalgia. In another exemplary embodiment, the disease is actinic keratosis. In another exemplary embodiment, the disease is atopic dermatitis. In another exemplary embodiment, the compound has a structure which is a member selected from:

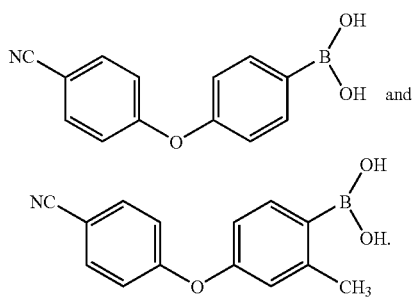

In another exemplary embodiment, the neurodegenerative disorder is a member selected from Alzheimer's disease and Parkinson disease, the inflammatory bowel disease is a member selected from Crohn's disease or uncerative colitis; the gastrointestinal complication is diarrhea; the liver disease is a member selected from an autoimmune hepatitis, hepatitis C, primary biliary cirrhosis, primary sclerosing cholangitis and fulminant liver failure; the gastrointestinal disorder is a member selected from celiac disease and non-specific colitis; the pulmonary disorder is a member selected from allergic rhinitis, asthma, chronic obstructive pulmonary disease, chronic granulomatous inflammation, cystic fibrosis, and sarcoidosis; the cardiovascular disease is a member selected from atheroscleotic cardiac disease, congestive heart failure and restenosis; and the renal disease is a member selected from glomerulpnephritis and vasculitis. In another exemplary embodiment, the compound is administered at a concentration sufficient to inhibit a cytokine which is a member selected from IL-1α, β, IL-2, IL-3, IL-6, IL-7, IL-9, IL-12, IL-17, IL-18, IL-23, TNF-α, LT, LIF, Oncostatin, and IFNc1α, β, γ. In another exemplary embodiment, the compound is administered at a concentration sufficient to stimulate expression of a cytokine which is a member selected from IL-4, IL-10, IL-11, W-13 and TGF-β. In another exemplary embodiment, the invention provides a method of treating an inflammatory-related disease associated with cytokine expression levels, which comprises administering to a human or an animal in need of such treatment a compound described in section IIIa. In an exemplary embodiment, the compound is in an amount sufficient to treat the inflammatory-related disease by inhibiting pro-inflammatory cytokine expression or by stimulating anti-inflammatory cytokine expression, but the amount is less than sufficient to substantially inhibit cyclin dependent kinases. In an exemplary embodiment, the animal is a human being. In another exemplary embodiment, the compound has a structure which is a member selected from:

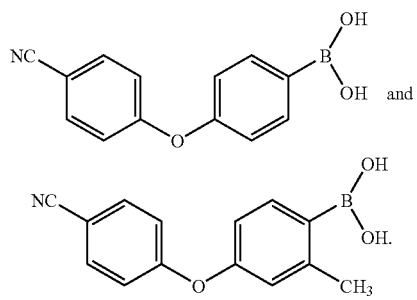

In another exemplary embodiment, the invention provides a method for inhibiting the production of an inflammatory cytokine protein by cells capable of producing said inflammatory cytokine protein, said method comprising: combining said cells with a therapeutic amount of a compound of section IIIa, wherein production of said inflammatory cytokine by said cells is inhibited. In another exemplary embodiment, the therapeutic amount is sufficient to inhibit the production of said inflammatory cytokine protein between about 50% and about 99%. In another exemplary embodiment, the invention provides a method for inhibiting an inflammatory response in a human or an animal, said method comprising: contacting said human or animal with a therapeutic amount of a compound in section IIIa, wherein said inflammatory response is inhibited. In another exemplary embodiment, the compound has a structure which is a member selected from:

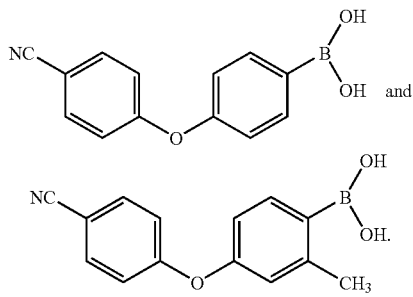

IV. Therapeutic Indications of the Compounds of the Invention

It should be understood that the present methods include, but are not limited to, treating an inflammatory-related disease with a compound of the invention.

In another aspect, the invention provides methods of preventing or treating diseases mediated by cytokines which comprise administering to a subject in need of such treatment a therapeutically effective amount of a compound of the invention. In an exemplary embodiment, the compound is a member selected from C1-C100. In an exemplary embodiment, the compound is 5-(4-cyanophenoxy)-1,3-dihydro-1-hydroxy-2,1-benzoxaborole. Such cytokine-mediated diseases include periodontitis, dry eye disease, rheumatoid arthritis, osteoarthritis, Crohn's disease, ulcerative colitis, psoriatic arthritis, traumatic arthritis, rubella arthritis, inflammatory bowel disease, multiple sclerosis, psoriasis, graft versus host disease, systemic lupus erythematosus, toxic shock syndrome, irritable bowel syndrome, muscle degeneration, allograft rejections, pancreatitis, insulitis, glomerulonephritis, diabetic nephropathy, renal fibrosis, chronic renal failure, gout, leprosy, acute synovitis, Reiter's syndrome, gouty arthritis, Behcet's disease, spondylitis, endometriosis, non-articular inflammatory conditions, such as intervertebral disk syndrome conditions, bursitis, tendonitis, tenosynovitis or fibromyalgic syndrome; and acute or chronic pain, including but not limited to neurological pain, neuropathies, polyneuropathies, diabetes-related polyneuropathies, trauma, migraine, tension and cluster headache, Horton's disease, varicose ulcers, neuralgias, musculo-skeletal pain, osteo-traumatic pain, fractures, algodystrophy, spondyloarthritis, fibromyalgia, phantom limb pain, back pain, vertebral pain, post-surgery pain, herniated intervertebral disc-induced sciatica, cancer-related pain, vascular pain, visceral pain, childbirth, or HIV-related pain. Other cytokine mediated diseases are allergy, a metabolic disease, a chemotherapy/radiation related complication; diabetes type I; diabetes type II; a liver disease; a gastrointestinal disorder; an ophthamological disease; allergic conjunctivitis; diabetic retinopathy; Sjogren's syndrome; uvetitis; a pulmonary disorder, a renal disease; dermatitis; HIV-related cachexia; cerebral malaria; ankylosing spondolytis; leprosy; anemia; fibromyalgia, kidney failure, stroke, chronic heart failure, endotoxemia, reperfusion injury, ischemia reperfusion, myocardial ischemia, restenosis, thrombosis, angiogenesis, Coronary Heart Disease, Coronary Artery Disease, acute coronary syndrome, Takayasu arteritis, cardiac failure such as heart failure, aortic valve stenosis, cardiomyopathy, myocarditis, vasculitis, vascular restenosis, valvular disease or coronary artery bypass; hypercholesterolemia, diseases or conditions related to blood coagulation or fibrinolysis, such as for example, acute venous thrombosis, pulmonary embolism, thrombosis during pregnancy, hemorrhagic skin necrosis, acute or chronic disseminated intravascular coagulation (DIC), clot formation from surgery, long bed rest or long periods of immobilization, venous thrombosis, fulminant meningococcemia, acute thrombotic strokes, acute coronary occlusion, acute peripheral arterial occlusion, massive pulmonary embolism, axillary vein thrombosis, massive iliofemoral vein thrombosis, occluded arterial or venous cannulae, cardiomyopathy, venoocclusive disease of the liver, hypotension, decreased cardiac output, decreased vascular resistance, pulmonary hypertension, diminished lung compliance, leukopenia or thrombocytopenia; or atherosclerosis. Yet others are allergic conjunctivitis, uveitis, glaucoma, optic neuritis, retinal ischemia, diabetic retinopathy, laser induced optic damage, or surgery or trauma-induced proliferative vitreoretinopathy. Cytokine mediated diseases further include allergic rhinitis, asthma, adult respiratory distress syndrome, chronic pulmonary inflammation, chronic obstructive pulmonary disease, emphysema, bronchitis, mucus hypersecretion, silicosis, SARS infection and respiratory tract inflammation. Also included are psoriasis, eczema, atopic dermatitis, contact dermatitis, or acne. Yet other cytokine mediated diseases are Guillain-Barre syndrome, Parkinson's disease, Huntington's disease, Alzheimer's disease, amyotrophic lateral sclerosis, multiple sclerosis and other demyelinating diseases, viral and bacterial meningitis, CNS trauma, spinal cord injury, seizures, convulsions, olivopontocerebellar atrophy, AIDS dementia complex, MERRF and MELAS syndromes, Leber's disease, Wernicke's encephalopathy, Rett syndrome, homocystinuria, hyperprolinemia, hyperhomocysteinemia, nonketotic hyperglycinemia, hydroxybutyric aminoaciduria, sulfite oxidase deficiency, combined systems disease, lead encephalopathy, Tourette's syndrome, hepatic encephalopathy, drug addiction, drug tolerance, drug dependency, depression, anxiety and schizophrenia, aneurism, or epilepsy. In another aspect of the invention, the cytokine mediated diseases include bone resorption diseases, osteopetrosis, osteoporosis, or osteoarthritis. Also included are diabetes, systemic cachexia, cachexia secondary to infection or malignancy, cachexia secondary to acquired immune deficiency syndrome (AIDS), obesity, anorexia or bulimia nervosa. Additionally, the cytokine mediated disease can be sepsis, HIV, HCV, malaria, infectious arthritis, leishmaniasis, Lyme disease, cancer, including but not limited to breast cancer, colon cancer, lung cancer, prostate cancer, multiple myeloma, acute myelogenous leukemia, myelodysplastic syndrome, non-Hodgkins lymphoma, or follicular lymphoma, Castleman's disease, or drug resistance.

In another aspect, the invention provides methods of treating neutrophil-mediated diseases which comprise administering to a subject in need of such treatment a therapeutically effective amount of a compound of the invention, wherein the neutrophil-mediated disease is bronchial asthma, rhinitis, influenza, stroke, myocardial infarction, thermal injury, adult respiratory distress syndrome (ARDS), multiple organ injury secondary to trauma, acute glomerulonephritis, dermatoses with acute inflammatory components, acute purulent meningitis, hemodialysis, leukopheresis, granulocyte transfusion associated syndromes, or necrotizing enterocolitis.

Preferably the neurodegenerative disorder is selected from the group consisting of: Alzheimer's disease and Parkinson disease; the inflammatory bowel disease is selected from the group consisting of: Crohn's disease or ulcerative colitis; the gastrointestinal complication is diarrhea; the liver disease is selected from the group consisting of: an autoimmune hepatitis, hepatitis C, primary biliary cirrhosis, primary sclerosing cholangitis, or fulminant liver failure; the gastrointestinal disorder is selected from the group consisting of: celiac disease and non-specific colitis; the bone disease is osteoporosis; the pulmonary disorder is selected from the group consisting of: allergic rhinitis, asthma, chronic obstructive pulmonary disease, chronic granulomatous inflammation, cystic fibrosis, and sarcoidosis; the cardiovascular disease is selected from the group consisting of: atheroscleotic cardiac disease, congestive heart failure and restenosis; and the renal disease is selected from the group consisting of: glomerulonephritis and vasculitis.

In a preferred embodiment the disease is inflammatory bowel disease (IBD), specifically including Crohn's disease and ulcerative colitis. In another preferred embodiment the disease being treated is arthritis, rheumatoid arthritis, psoriasis, Alzheimer's disease, or Parkinson disease. In yet another preferred embodiment the disease is post-radiotherapy related disease or atherosclerosis.

Preferably the compound is in an amount to inhibit pro-inflammatory cytokine expression and/or to stimulate anti-inflammatory cytokine expression. In an exemplary embodiment, the compound is a member selected from C1-C100. In an exemplary embodiment, the compound is 5-(4-cyanophenoxy)-1,3-dihydro-1-hydroxy-2,1-benzoxaborole. In one embodiment, the compound is preferably in an amount to inhibit at least 30 to 100% expression of one or more of the pro-inflammatory cytokines selected from the group consisting of: IL-1α, β, IL-2, IL-3, IL-6, IL-7, IL-9, IL-12, IL-17, IL-18, IL-23, TNF-α, LT, LIF, Oncostatin, and IFNc1α, β, γ. In an exemplary embodiment, the compound is in an amount to inhibit at least 40 to 100% expression of one or more of the pro-inflammatory cytokines. In an exemplary embodiment, the compound is in an amount to inhibit at least 50 to 100% expression of one or more of the pro-inflammatory cytokines. In an exemplary embodiment, the compound is in an amount to inhibit at least 60 to 100%. In an exemplary embodiment, the compound is in an amount to inhibit at least 70 to 100%. In an exemplary embodiment, the compound is in an amount to inhibit at least 30 to 70% expression of one or more of the pro-inflammatory cytokines. In an exemplary embodiment, the compound is in an amount to inhibit at least 40 to 90% expression of one or more of the pro-inflammatory cytokines. In an exemplary embodiment, the compound is in an amount to inhibit at least 45 to 80% expression of one or more of the pro-inflammatory cytokines. In an exemplary embodiment, the compound is in an amount to inhibit at least 55 to 75% expression of one or more of the pro-inflammatory cytokines. In an exemplary embodiment, the compound is in an amount to inhibit at least 75 to 98% expression of one or more of the pro-inflammatory cytokines. In an exemplary embodiment, the compound is in an amount to inhibit between about 50% and about 99% expression of one or more of the pro-inflammatory cytokines. In another embodiment, the compound is preferably in an amount to stimulate anti-inflammatory cytokine expression. In this embodiment, the compound is preferably in an amount to increase the anti-inflammatory cytokine selected from the group consisting of: cytokine IL-4, IL-10, IL-11, W-13 or TGF-β by at least 25%, more preferably at least 50%, and most preferably at least 75%.

This invention provides a method of using a class of boron-containing small molecules for the treatment of various inflammatory-related diseases in humans or animals. In an exemplary embodiment, the small molecule is a compound described herein. In an exemplary embodiment, the compound is a member selected from C1-C100. In an exemplary embodiment, the compound is 5-(4-cyanophenoxy)-1,3-dihydro-1-hydroxy-2,1-benzoxaborole. These inflammatory-related diseases include, but are not limited to inflammatory bowel diseases (IBD), psoriasis, rheumatoid arthritis (RA), multiple sclerosis (MS), neurodegenerative disorders, cardiovascular disease (CVD) and atherosclerosis, and metabolic disease (the metabolic syndrome and diabetes) as well as infection-related inflammation.

The invention also provides a method of treating an inflammatory-related disease associated with cytokine expression levels, which comprises administering to a human or an animal in need of such treatment the compound of the invention.

The invention also provides a method wherein the animal being treated is a member selected from a human, a horse, a cow and a pig. In an exemplary embodiment, the animal is a human.

In an exemplary embodiment, the invention provides a method of inhibiting a cytokine that is a member selected from IL-1β, IL-4, TNF-α and IFNγ. In this method, the cytokine is contacted with a compound of the invention. In an exemplary embodiment, the compound is a member selected from C1-C100. In an exemplary embodiment, the compound is 5-(4-cyanophenoxy)-1,3-dihydro-1-hydroxy-2,1-benzoxaborole. Tumor necrosis factor-α (TNF-α) and interleukin-1 (IL-1) are proinflammatory cytokines that mediate inflammatory responses associated with infectious agents and other cellular stresses. Overproduction of cytokines such as IL-1 and TNF-α is believed to underlie the progression of many inflammatory diseases including rheumatoid arthritis (RA), Crohn's disease, inflammatory bowel disease, multiple sclerosis, endotoxin shock, osteoporosis, Alzheimer's disease, congestive heart failure, and psoriasis among others (Dinarello, C. A. et al., *Rev. Infect. Diseases* 1984, 6:51; Salituro et al., *Curr. Med. Chem.* 1999, 6:807-823; Henry et al., *Drugs Fut.* 1999, 24:1345-1354). An accepted therapeutic approach for potential drug intervention in these conditions is the reduction of proinflammatory cytokines such as TNF-α (also referred to as TNFa) and interleukin-1β (IL-1b).

Inflammatory Bowel Disease (IBD): IBD comprises Crohn's disease (CD) and ulcerative colitis (UC), which are two overlapping chronic inflammatory-related diseases of the gastrointestinal tract caused by dysregulation of the immune system (Rutgeerts, P., *Aliment Pharmacol Ther,* 17: 185-192 (2003)). Patients with IBD have defective intestinal epithelial barrier function, which allows bacterial colonization of the epithelia. As a result, bacterial products and pro-inflammatory cytokines (TNF-α, IL-1 and IL-6) cause persistent inflammatory stimulation. Bacterial antigens are introduced into the immune system by mucosal dendritic cells and macrophases. In response, intestinal phagocytes (mainly monocytes and neutrophils) proliferate and increase expression and secretion of pro-inflammatory cytokines.

Psoriasis: Cytokines are intercellular messengers that have an important role in the development and maintenance of cutaneous inflammation. A number of cytokines have been reported to play crucial roles in the pathogenesis of inflammatory skin disorders. IL-1, TNF-α, and IFN-γ induce expression of ICAM-1 and major histocompatibility complex (MHC) class II (Dustin, M. L., *J Immunol,* 137: 245-254, (1986); Strange, P., *J Invest Dermatol,* 102: 150-154, (1994)). IL-1, TNF-α, and granulocyte-macrophage colony-stimulation factor are able to induce activation, maturation, and migration of dendritic cells, and IL-1 activates mast cells (50). IL-6 and TGF-α enhance keratinocyte proliferation. IL-1, TNF-α, TGF-α, and VEGF induce angiogenesis and attract inflammatory cells (Grossman, R. M., Proc Natl Acad Sci USA, 86: 6367-6371, (1989); Schreiber, A. B., *Science,* 232: 1250-1253, (1986); Detmar, M., *J Exp Med,* 180: 1141-

1146, (1994)). The primacy of cytokines in eliciting cutaneous immune responses makes them a highly attractive target for new biological response modifiers (Williams, J. D., *Clin Exp Dermatol,* 27: 585-590, (2002)).

Rheumatoid arthritis (RA): The role of the cytokine network in mediating inflammation and joint destruction in RA has been extensively investigated in recent years. In addition to TNF-α, IL-1 plays a pivotal role in the pathogenesis and the clinical manifestations of RA (54). The ability of IL-1 to drive inflammation and joint erosion and to inhibit tissue repair processes has been clearly established in vitro systems and in animal models, and alleviation of inflammatory symptoms in RA patients has been achieved by blockage of IL-1 (Bresnihan, B., *Arthritis Rheum,* 41: 2196-2204, (1998)). IL-6 is a multifunctional cytokine that regulates the immune response, hematopoiesis, the acute phase response, and inflammation. Deregulation of IL-6 production is implicated in the pathology of several diseases including RA. A therapeutic approach to block the IL-6 signal has been carried out by using humanized anti-IL-6R antibody for RA among other diseases (Ito, H., *Curr Drug Targets Inflamm Allergy,* 2: 125-130, (2003); Ishihara, K *Cytokine Growth Factor Rev,* 13: 357-368, (2002)). IL-10 is an anti-inflammatory cytokine. Expressing IL-10 has been shown to prevent arthritis or ameliorate the disease in animal models (57, 58). While it is obvious that cytokines such as TNF-α, IL-1, IL-6 and IL-10 have independent roles, they act in concert in mediating certain pathophysiological processes in RA. The finding of a class of molecules described in this invention, which are able to modulate these different cytokines, will result in dramatic therapeutic progress in the treatment of RA.

Multiple Sclerosis (MS): MS is an autoimmune inflammatory disorder. Although the cause of the body attacking its own myelin in MS patients remains unclear, deregulated cytokines are clearly involved in the process of the disease. Using experimental autoimmune encephalomyelitis (EAE), a widely used model for studies of MS based on autoimmune, histopathological, genetic and clinical similarities, it has been shown that in the early active stage, both EAE and MS are characterized by the presence of perivascular inflammatory cuffs disseminated in the CNS, a process in which chemoattractant cytokines (chemokines) play an important role. There is evidence that the expression of chemokines (IL-8 family members) during CNS autoimmune inflammation is regulated by some pro-inflammatory cytokines, such as TNF (Glabinski, A. R., *Scand J Immunol,* 58: 81-88, (2003)). The roles of other pro-/anti-inflammatory cytokines such as IL-1.beta., IL-6 and IL-10 were also confirmed in EAE animal models (Diab, A., *J Neuropathol Exp Neurol,* 56: 641-650, (1997); Samoilova, E. B., *J Immunol,* 161: 6480-6486, (1998); Robertson, J., *J Cell Biol,* 155: 217-226, (2001)) as well as in humans (de Jong, B. A., *J Neuroimmunol,* 126: 172-179, (2002)). IL-1β is present in MS lesions. IL-1 receptor antagonist (IL-1Ra) moderates the induction of experimental autoimmune encephalomyelitis (EAE). Increased risk of MS has been seen in individuals with High IL-1 (3 over IL-1Ra production ratio and high TNF over IL-10 production ratio (de Jong, B. A., *J Neuroimmunol,* 126: 172-179, (2002)).

Neurodegenerative disorders: Alzheimer's disease (AD) and Parkinson's disease (PK) are the 2 most common neurodegenerative disorders related to neuroinflammation. Neuroinflammation is a characteristic of pathologically affected tissue in several neurodegenerative disorders. These changes are particularly observed in affected brain areas of AD cases (McGeer, E. G., *Prog Neuropsychopharmacol Biol Psychiatry,* 27: 741-749, (2003)). The role of cytokines has been implicated in the pathogenesis of AD, although the mechanism by which cytokines contribute to the pathogenesis is not fully understood. In AD, microglia, especially those associated with amyloid deposits, have a phenotype that is consistent with a state of activation, including immunoreactivity with antibodies to class II major histocompatibility antigens and to inflammatory cytokines, IL-1β and TNF-α(Dickson, D. W., *Glia,* 7: 75-83, (1993)). One of the major neuropathological characteristics of AD is the brain deposition of senile plaques that are mainly composed of toxic amyloid beta-peptide (Abeta), which is generated from a family of Abeta containing precursor proteins (AbetaPP). Cytokines have been shown to stimulate gene expression of transcription of AbetaPP. Analysis of genetic linkage of loci controlling age-at-onset in AD and PK revealed a significant association of AD with glutathione S-transferase, omega-1 and 2 (GSTO1, GSTO2) genes. The function of GSTO1 appears related to the post-translational processing of pro-inflammatory cytokine IL-1β (Laliberte, R. E., *J Biol Chem,* 278: 16567-16578, (2003)).

Post-radiotherapy related Inflammation: Radiation damage related inflammatory diseases to the rectum and sigmoid colon are most common complications with radiation therapy for cancers in the pelvic region, which include cancers of the cervix, uterus, prostate, bladder, and testes. Radiation proctosigmoiditis is the most common clinically apparent form of colonic damage after pelvic irradiation with an incidence of 5% to 20%. Patients typically exhibit symptoms of tenesmus, bleeding, low-volume diarrhea, and rectal pain. Rarely, low-grade obstruction or fistulous tracts into adjacent organs may develop.

The mechanism of radiation therapy is through its damage to DNA in actively proliferating cells. The pathological damages after localized radiation therapy to the intestine/colon can be divided into acute and chronic phases. The initial pathological changes include a loss of lymphocytes in the lamina propria and microscopic damage to mucosal epithelial cells and vascular endothelial cells. These changes manifest as villous blunting and a decrease in crypt regenerative cells and are followed by marked submucosal edema with increase of vascular permeability.

Progressive endarteritis appears to be the major mechanism by which the chronic effects occur, which later manifest as progressive fibrosis leading to mucosal atrophy, stricture formation, and thrombosis, causing secondary ischemic damage. Radiation colitis in the chronic phase demonstrates a very significant crypt distortion, vascular telangiectasia, and fibrosis of the lamina propria. Interestingly, some of these pathological changes are also present in long-standing IBD (Haboubi, N.Y., *J Clin Pathol,* 45: 272, (1992).

Thus, cytokines may play a key role among various gastrointestinal diseases in which inflammation exhibits a significant part. Recent studies have focused on the crucial role of cytokines in chronic IBD (Brynskov, J., *Gut,* 33: 55-58, (1992); Matsuura, T., *Gastroenterology,* 104: 448-458, (1993); Beagley, K. W., *Gastroenterol Clin North Am,* 21: 347-366, (1992); MacDermott, R. P., *Med Clin North Am,* 78: 1207-1231, (1994); Isaacs, K. L., Gastroenterology, 103: 1587-1595, (1992); Indaram, A. V., *World J Gastroenterol,* 6: 49-52, (2000)). To elucidate the role of cytokines in radiation proctitis, Indaram et al. (Indaram, A. V., *Am J Gastroenterol,* 95: 1221-1225, (2000)) examined the colonic mucosal cytokine levels in patients with radiation proctitis and compared these values with those obtained from normal controls and patients with IBD. They found that the mucosal levels of IL-2, IL-6, and IL-8 were significantly higher and statistically significant ($p<0.05$) in both diseased (5.62.+−.0.13, 1.60.+−.0.31, 21.45.+−.4.03 pg/mg) and normal-appearing mucosa (3.83.+−.0.78, 1.36.+−.0.34, 13.45.+−.3.18 pg/mg) in the radiation proctitis group, compared with those of normal controls (1.74.+−.0.23, 0.67.+−.0.05, 4.99.+−. 1.39 pg/mg).

Thus, these findings demonstrate a similar activation of cytokines in patients with radiation proctitis and IBD. In the radiation proctitis patients it was demonstrated that IL-2, IL-6, and IL-8 levels in the mucosa were significantly greater compared to normal controls. In comparison, the IBD (UC and CD) patients demonstrated significantly higher levels of the cytokines including IL-1, IL-2, IL-6, and IL-8 compared to the normal controls.

The similarity in mucosal cytokine expression in these two diseases plausibly relates directly to the intense inflammatory nature of the diseases. It has been postulated that this similarity in cytokine activation in these two diseases may translate into the similar pathological changes seen in chronic IBD and radiation proctitis. This hypothesis is supported by that fact that the medical management of radiation proctitis, albeit rather unsatisfactorily, includes treatment with various aminosalicylic acid derivatives and corticosteroids given orally or topically. These treatment options are identical to the management of IBD.

Other Cytokine Deregulation Related Diseases: Cardiovascular disease (CVD), atherosclerosis, and metabolic disease (the metabolic syndrome) also have been linked to the improper secretion/expression of pro/anti-inflammatory cytokines (DeGraba, T. J., *Adv Neurol,* 92: 29-42, (2003); von der Thusen, J. H., *Pharmacol Rev,* 55:133-166, (2003); Schmidt, M. I., *Clin Chem Lab Med,* 41:1120-1130, (2003); Virdis, A., *Curr Opin Nephrol Hypertens,* 12: 181-187, (2003); Ito, T., *Curr Drug Targets Inflamm Allergy,* 2: 257-265, (2003)).

Diabetes: A fundamental defect in type II diabetes is insulin resistance, by which insulin fails to suppress glucose production from the liver and to promote consumption by peripheral tissues, resulting in hyperglycemia. Pancreatic β cells respond to excess plasma glucose by secreting more insulin to overcome the effects of insulin resistance. As insulin resistance progresses and the P cells are no longer able to meet the requirement for increasing amount of insulin secretion, plasma glucose levels increase and type II diabetes develops.

Many factors may contribute to the onset of type II diabetes. Since 80% of the patients with type II diabetes are obese and obesity is always associated with insulin resistance, molecular mediators that link obesity to insulin resistance have been under extensive research. A variety of factors have been identified as contributing causes of insulin resistance in obesity and obesity-linked type II diabetes, notable those produced by adipose tissue, FFAs (free fatty acids), TNF-α, IL-6, leptin, adiponectin, and resistin. Both mRNA and protein levels of TNF-α are highly increased in the adipose tissues of obese animals (Hotamisligil, G. S., *Science,* 259: 87-91, (1993)) and human subjects (Hotamisligil, G. S., *J Clin Invest,* 95: 2409-2415, (1995)). All different types of cell in the adipose tissue are capable of producing cytokines. Adipocytes express TNF-α receptors and are also the major source of TNF-α, which is thought to function predominantly in an autocrine/paracrine manner in adipose tissue.

Long-term exposure of cultured cells (Hotamisligil, G. S., *Proc Natl Acad Sci USA,* 91. 4854-4858, (1994)) or animals (Lang, C. H., *Endocrinology,* 130: 43-52, (1992)) to TNF-α induces insulin resistance, whereas neutralization of TNF-αincreases insulin sensitivity and reduces hyperglycemia in a type II diabetes animal model (Hotamisligil, G. S., *Diabetes,* 43: 1271-1278, (1994)). Absence of TNF-α or TNF-α receptors by gene knock-out significantly improves insulin sensitivity in obesity animal models (Uysal, K. T., *Nature,* 389: 610-614, (1997)).

Mechanisms have been proposed for TNF-α induced insulin resistance in adipocytes as well as systemically (Ruan, H., *Cytokine Growth Factor Rev,* 14: 447-455, (2003)). TNF-α inhibits phosphorylation of insulin receptor and insulin receptor substrate-1 (IRS-1) through the inhibitor kB kinase-β (IKK-β). NF-kB activation by TNF-α is obligatory for repression of adipocyte-abundant genes essential for adipocyte function, and is also sufficient to inhibit PPAR-gamma-mediated gene transcription. TNF-α also stimulate lipolysis and other cytokine expression in adipose tissue, and triggers FFA release. In fact, plasma FFVs levels increase before overt hyperglycemia in some animal models of insulin resistance (Ruan, H., *Cytokine Growth Factor Rev,* 14: 447-455, (2003)). There are extensive evidence implicating excess plasma FFA in induction and progression of systemic insulin resistance. In hepatocytes, FFAs contribute to excessive glucose and VLDL production. In muscle cells, high level of FFA impair insulin signaling and promote FFA oxidation leading to greatly decreased glucose ox.

Currently available insulin sensitizing drugs, which belong to PPAR-gamma agonist, inhibit TNF-α-induced adipocytes gene expression profile through NF-kB pathway (Ruan, H., *J Biol Chem,* 278: 28181-28192, (2003). As adipocyte-derived TNF-α functions as autocrine or paracrine factor, systemic delivery of TNF-αantibody may not be effective in blocking the biological activity of locally expressed TNF-α in adipose tissue (Ofei, F., *Diabetes,* 45: 881-885, (1996)). NATURA, which represents a new type of small molecule TNF-α inhibitor distributing through simple diffusion, could therefore be effective agent to block the function of locally expressed TNF-α and potentially useful in the treatment of type 2 diabetes.

Type I diabetes mellitus is an autoimmune disease characterized by mononuclear cell infiltration in the islets of Langerhans and selective destruction of the insulin producing beta cells. While CD8+ T cells may be important initiators, CD4+ T cells (Suri, A., *Immunol Rev,* 169: 55-65, (1999)) and macrophages (Jun, H. S., *Diabetes,* 48: 34-42, (1999); Yoon, J. W., *Autoimmunity,* 27: 109-122, (1998)), are the major cellular effectors of the immune process leading to beta cell death. Activated macrophages directly secrete IL-1β, IL-6, IL-12, TNF-α, indirectly trigger INF-gamma production from activated T cells. The involvement of cytokines like TNF-α, INF-γ, IL-β, IL-6 and IL-10, in the pathogenesis of type 1 diabetes has been well clarified through correlation studies of cytokine expression and development of type I diabetes, cytokine augmentation studies and cytokine deficiency studies. (Rabinovitch, A., *Rev Endocr Metab Disord,* 4: 291-299, (2003)). In addition to cytokine neutralizing antibodies and soluble cytokine receptors, anti-inflammatory compounds also show the effects of delaying or preventing the onset of type 1 diabetes in animal models.

In summary, dysregulation of cytokines is involved in a variety of diseases, including inflammatory-related diseases and those normally not considered inflammatory-related diseases. A molecule that is capable of modulating both pro- and anti-inflammatory cytokines should provide therapeutic benefits with minimal side effects for all types of diseases related to dysfunction of these inflammation components.

V. Pharmaceutical Formulations

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The compositions of the invention may be administered orally, topically, parenterally, by inhalation or spray or rectally in dosage unit formulations containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a single dosage form will vary depending upon the condition being treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocycles may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the patient and will ultimately be at the discretion of the attendant physician or clinician.

V. a) Topical Formulations

In a preferred embodiment, the methods of the invention can be used employed through the topical application of the compounds described herein.

The compositions of the present invention comprises fluid or semi-solid vehicles that may include but are not limited to polymers, thickeners, buffers, neutralizers, chelating agents, preservatives, surfactants or emulsifiers, antioxidants, waxes or oils, emollients, sunscreens, and a solvent or mixed solvent system. The solvent or mixed solvent system is important to the formation because it is primarily responsible for dissolving the drug. The best solvent or mixed solvent systems are also capable of maintaining clinically relevant levels of the drug in solution despite the addition of a poor solvent to the formulation. The topical compositions useful in the subject invention can be made into a wide variety of product types. These include, but are not limited to, lotions, creams, gels, sticks, sprays, ointments, pastes, foams, mousses, and cleansers. These product types can comprise several types of carrier systems including, but not limited to particles, nanoparticles, and liposomes. If desired, disintegrating agents can be added, such as the cross-linked polyvinyl pyrrolidone, agar or alginic acid or a salt thereof such as sodium alginate. Techniques for formulation and administration can be found in *Remington: The Science and Practice of Pharmacy*, supra. The formulation can be selected to maximize delivery to a desired target site in the body.

Lotions, which are preparations that are to be applied to the skin, nail, hair, claw or hoof surface without friction, are typically liquid or semi-liquid preparations in which finely divided solid, waxy, or liquid are dispersed. Lotions will typically contain suspending agents to produce better dispersions as well as compounds useful for localizing and holding the active agent in contact with the skin, nail, hair, claw or hoof, e.g., methylcellulose, sodium carboxymethyl-cellulose, or the like.

Creams containing the active agent for delivery according to the present invention are viscous liquid or semisolid emulsions, either oil-in-water or water-in-oil. Cream bases are water-washable, and contain an oil phase, an emulsifier and an aqueous phase. The oil phase is generally comprised of petrolatum or a fatty alcohol, such as cetyl- or stearyl alcohol; the aqueous phase usually, although not necessarily, exceeds the oil phase in volume, and generally contains a humectant. The emulsifier in a cream formulation, as explained in *Remington: The Science and Practice of Pharmacy*, supra, is generally a nonionic, anionic, cationic or amphoteric surfactant.

Gel formulations can also be used in connection with the present invention. As will be appreciated by those working in the field of topical drug formulation, gels are semisolid. Single-phase gels contain organic macromolecules distributed substantially uniformly throughout the carrier liquid, which is typically aqueous, but also may be a solvent or solvent blend.

Ointments, which are semisolid preparations, are typically based on petrolatum or other petroleum derivatives. As will be appreciated by the ordinarily skilled artisan, the specific ointment base to be used is one that provides for optimum delivery for the active agent chosen for a given formulation, and, preferably, provides for other desired characteristics as well, e.g., emolliency or the like. As with other carriers or vehicles, an ointment base should be inert, stable, nonirritating and non-sensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, reference may be had to Remington: The Science and Practice of Pharmacy, supra, for further information.

Useful formulations of the invention also encompass sprays. Sprays generally provide the active agent in an aqueous and/or alcoholic solution which can be misted onto the skin, nail, hair, claw or hoof for delivery. Such sprays include those formulated to provide for concentration of the active agent solution at the site of administration following delivery, e.g., the spray solution can be primarily composed of alcohol or other like volatile liquid in which the drug or active agent can be dissolved. Upon delivery to the skin, nail, hair, claw or hoof, the carrier evaporates, leaving concentrated active agent at the site of administration.

The topical pharmaceutical compositions may also comprise suitable solid or gel phase carriers. Examples of such carriers include but are not limited to calcium carbonate, calcium phosphate, various sugars, starches, cellulose derivatives, gelatin, and polymers such as polyethylene glycols.

The topical pharmaceutical compositions may also comprise a suitable emulsifier which refers to an agent that enhances or facilitates mixing and suspending oil-in-water or water-in-oil. The emulsifying agent used herein may consist of a single emulsifying agent or may be a nonionic, anionic, cationic or amphoteric surfactant or blend of two or more such surfactants; preferred for use herein are nonionic or anionic emulsifiers. Such surface-active agents are described in "McCutcheon's Detergent and Emulsifiers," North American Edition, 1980 Annual published by the McCutcheon Division, MC Publishing Company, 175 Rock Road, Glen Rock, N.J. 07452, USA.

Preferred for use herein are high molecular weight alcohols such as cetearyl alcohol, cetyl alcohol, stearyl alcohol, emulsifying wax, glyceryl monostearate. Other examples are ethylene glycol distearate, sorbitan tristearate, propylene glycol monostearate, sorbitan monooleate, sorbitan monostearate (SPAN 60), diethylene glycol monolaurate, sorbitan monopalmitate, sucrose dioleate, sucrose stearate (CRODESTA F-160), polyoxyethylene lauryl ether (BRIJ 30), polyoxyethylene (2) stearyl ether (BRIJ 72), polyoxyethylene (21) stearyl ether (BRIJ 721), polyoxyethylene monostearate (Myrj 45), polyoxyethylene sorbitan monostearate (TWEEN 60), polyoxyethylene sorbitan monooleate (TWEEN 80), polyoxyethylene sorbitan monolaurate (TWEEN 20) and sodium oleate. Cholesterol and cholesterol derivatives may also be employed in externally used emulsions and promote w/o emulsions.

Especially suitable nonionic emulsifying agents are those with hydrophile-lipophile balances (HLB) of about 3 to 6 for w/o system and 8 to 18 for o/w system as determined by the method described by Paul L. Lindner in "Emulsions and Emulsion", edited by Kenneth Lissant, published by Dekker, New York, N.Y., 1974, pages 188-190. More preferred for use herein are one or more nonionic surfactants that produce a system having HLB of about 8 to about 18.

Examples of such nonionic emulsifiers include but are not limited to "BRIJ 72", the trade name for a polyoxyethylene (2) stearyl ether having an HLB of 4.9; "BRIJ 721", the trade name for a polyoxyethylene (21) stearyl ether having an HLB of 15.5, "Brij 30", the trade name for polyoxyethylene lauryl ether having an HLB of 9.7; "Polawax", the trade name for emulsifying wax having an HLB of 8.0; "Span 60", the trade name for sorbitan monostearate having an HLB of 4.7; "Crodesta F-160", the trade name for sucrose stearate" having an HLB of 14.5. All of these materials are available from Ruger Chemicals Inc.; Croda; ICI Americas, Inc.; Spectrum Chemicals; and BASF. When the topical formulations of the present invention contain at least one emulsifying agent, each emulsifying agent is present in amount from about 0.5 to about 2.5 wt %, preferably 0.5 to 2.0%, more preferably 1.0% or 1.8%. Preferably the emulsifying agent comprises a mixture of steareth 21 (at about 1.8%) and steareth 2 (at about 1.0%).

The topical pharmaceutical compositions may also comprise suitable emollients. Emollients are materials used for the prevention or relief of dryness, as well as for the protection of the skin, nail, hair, claw or hoof. Useful emollients include, but are not limited to, cetyl alcohol, isopropyl myristate, stearyl alcohol, and the like. A wide variety of suitable emollients are known and can be used herein. See e.g., Sagarin, Cosmetics, Science and Technology, 2nd Edition, Vol. 1, pp. 32-43 (1972), and U.S. Pat. No. 4,919,934, to Deckner et al., issued Apr. 24, 1990, both of which are incorporated herein by reference in their entirety. These materials are available from Ruger Chemical Co, (Irvington, N.J.).

When the topical formulations of the present invention contain at least one emollient, each emollient is present in an amount from about 0.1 to 15%, preferably 0.1 to about 3.0, more preferably 0.5, 1.0, or 2.5 wt %. Preferably the emollient is a mixture of cetyl alcohol, isopropyl myristate and stearyl alcohol in a 1/5/2 ratio. The emollient may also be a mixture of cetyl alcohol and stearyl alcohol in a 1/2 ratio.

The topical pharmaceutical compositions may also comprise suitable antioxidants, substances known to inhibit oxidation. Antioxidants suitable for use in accordance with the present invention include, but are not limited to, butylated hydroxytoluene, ascorbic acid, sodium ascorbate, calcium ascorbate, ascorbic palmitate, butylated hydroxyanisole, 2,4,5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone and tocopherols such as vitamin E, and the like, including pharmaceutically acceptable salts and esters of these compounds. Preferably, the antioxidant is butylated hydroxytoluene, butylated hydroxyanisole, propyl gallate, ascorbic acid, pharmaceutically acceptable salts or esters thereof, or mixtures thereof. Most preferably, the antioxidant is butylated hydroxytoluene. These materials are available from Ruger Chemical Co, (Irvington, N.J.).

When the topical formulations of the present invention contain at least one antioxidant, the total amount of antioxidant present is from about 0.001 to 0.5 wt %, preferably 0.05 to about 0.5 wt %, more preferably 0.1%.

The topical pharmaceutical compositions may also comprise suitable preservatives. Preservatives are compounds added to a pharmaceutical formulation to act as an anti-microbial agent. Among preservatives known in the art as being effective and acceptable in parenteral formulations are benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. See, e.g., Wallhausser, K.-H., Develop. Biol. Standard, 24:9-28 (1974) (S. Krager, Basel). Preferably, the preservative is selected from methylparaben, propylparaben and mixtures thereof. These materials are available from Inolex Chemical Co (Philadelphia, Pa.) or Spectrum Chemicals.

When the topical formulations of the present invention contain at least one preservative, the total amount of preservative present is from about 0.01 to about 0.5 wt %, preferably from about 0.1 to 0.5%, more preferably from about 0.03 to about 0.15. Preferably the preservative is a mixture of methylparaben and proplybarben in a 5/1 ratio. When alcohol is used as a preservative, the amount is usually 15 to 20%.

The topical pharmaceutical compositions may also comprise suitable chelating agents to form complexes with metal cations that do not cross a lipid bilayer. Examples of suitable chelating agents include ethylene diamine tetraacetic acid (EDTA), ethylene glycol-bis(beta-aminoethyl ether)-N,N,N', N'-tetraacetic acid (EGTA) and 8-Amino-2-[(2-amino-5-methylphenoxy)methyl]-6-methoxyquinoline-N,N,N',N'-tetraacetic acid, tetrapotassium salt (QUIN-2). Preferably the chelating agents are EDTA and citric acid. These materials are available from Spectrum Chemicals.

When the topical formulations of the present invention contain at least one chelating agent, the total amount of chelating agent present is from about 0.005% to 2.0% by weight, preferably from about 0.05% to about 0.5 wt %, more preferably about 0.11% by weight.

The topical pharmaceutical compositions may also comprise suitable neutralizing agents used to adjust the pH of the formulation to within a pharmaceutically acceptable range. Examples of neutralizing agents include but are not limited to trolamine, tromethamine, sodium hydroxide, hydrochloric acid, citric acid, and acetic acid. Such materials are available from are available from Spectrum Chemicals (Gardena, Calif.).

When the topical formulations of the present invention contain at least one neutralizing agent, the total amount of neutralizing agent present is from about 0.1 wt to about 10 wt %, preferably 0.1 wt % to about 5.0 wt %, and more preferably about 1.0 wt %. The neutralizing agent is generally added in whatever amount is required to bring the formulation to the desired pH.

The topical pharmaceutical compositions may also comprise suitable viscosity increasing agents. These components are diffusible compounds capable of increasing the viscosity of a polymer-containing solution through the interaction of the agent with the polymer. CARBOPOL ULTREZ 10 may be used as a viscosity-increasing agent. These materials are available from Noveon Chemicals, Cleveland, Ohio.

When the topical formulations of the present invention contain at least one viscosity increasing agent, the total amount of viscosity increasing agent present is from about 0.25% to about 5.0% by weight, preferably from about 0.25% to about 1.0 wt %, and more preferably from about 0.4% to about 0.6% by weight.

The topical pharmaceutical compositions may also comprise suitable nail penetration enhancers. Examples of nail penetration enhancers include mercaptan compounds, sulfites and bisulfites, keratolytic agents and surfactants. Nail penetration enhancers suitable for use in the invention are described in greater detail in Malhotra et al., *J. Pharm. Sci.*, 91:2, 312-323 (2002), which is incorporated herein by reference in its entirety.

The topical pharmaceutical compositions may also comprise one or more suitable solvents. The ability of any solid substance (solute) to dissolve in any liquid substance (solvent) is dependent upon the physical properties of the solute and the solvent. When solutes and solvents have similar physical properties the solubility of the solute in the solvent will be the greatest. This gives rise to the traditional understanding that "like dissolves like." Solvents can be characterized in one extreme as non-polar, lipophilic oils, while in the other extreme as polar hydrophilic solvents. Oily solvents dissolve other non-polar substances by Van der Wals interactions while water and other hydrophilic solvents dissolve polar substances by ionic, dipole, or hydrogen bonding interactions. All solvents can be listed along a continuum from the least polar, i.e. hydrocarbons such as decane, to the most polar solvent being water. A solute will have its greatest solubility in solvents having equivalent polarity. Thus, for drugs having minimal solubility in water, less polar solvents will provide improved solubility with the solvent having polarity nearly equivalent to the solute providing maximum solubility. Most drugs have intermediate polarity, and thus experience maximum solubility in solvents such as propylene glycol or ethanol, which are significantly less polar than water. If the drug has greater solubility in propylene glycol (for example 8% (w/w)) than in water (for example 0.1% (w/w)), then addition of water to propylene glycol should decrease the maximum amount of drug solubility for the solvent mixture compared with pure propylene glycol. Addition of a poor solvent to an excellent solvent will decrease the maximum solubility for the blend compared with the maximum solubility in the excellent solvent.

When compounds are incorporated into topical formulations the concentration of active ingredient in the formulation may be limited by the solubility of the active ingredient in the chosen solvent and/or carrier. Non-lipophilic drugs typically display very low solubility in pharmaceutically acceptable solvents and/or carriers. For example, the solubility of some compounds in the invention in water is less than 0.00025% wt/wt. The solubility of the same compounds in the invention can be less than about 2% wt/wt in either propylene glycol or isopropyl myristate. In one embodiment of the present invention, diethylene glycol monoethyl ether (DGME) is the solvent used to dissolve the compounds described herein. In one embodiment of the present invention, diethylene glycol monoethyl ether (DGME) is the solvent used to dissolve a compound described herein, such as for example the compounds of Formula (I) or Formula (II). The compounds in the invention useful in the present formulation are believed to have a solubility of from about 10% wt/wt to about 25% wt/wt in DGME. In another embodiment a DGME water cosolvent system is used to dissolve the compounds described herein. In another embodiment a DGME water cosolvent system is used to dissolve a compound described herein, such as for example the compounds of Formula (I) or Formula (II). The solvent capacity of DGME drops when water is added; however, the DGME/water cosolvent system can be designed to maintain the desired concentration of from about 0.1% to about 5% wt/wt active ingredient. Preferably the active ingredient is present from about 0.5% to about 3% wt/wt, and more preferably at about 1% wt/wt, in the as-applied topical formulations. Because DGME is less volatile than water, as the topical formulation evaporates upon application, the active agent becomes more soluble in the cream formulation. This increased solubility reduces the likelihood of reduced bioavailability caused by the drug precipitating on the surface of the skin, nail, hair, claw or hoof.

Liquid forms, such as lotions suitable for topical administration or suitable for cosmetic application, may include a suitable aqueous or nonaqueous vehicle with buffers, suspending and dispensing agents, thickeners, penetration enhancers, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges and the like.

Additionally, the compounds can be delivered using a sustained-release system, such as semipermeable matrices of solid hydrophobic polymers containing the therapeutic agent. Various sustained-release materials have been established and are well known by those skilled in the art.

Topical treatment regimens according to the practice of this invention comprise applying the composition directly to the skin, nail, hair, claw or hoof at the application site, from one to several times daily.

Formulations of the present invention can be used to treat, ameliorate or prevent conditions or symptoms associated with bacterial infections, acne, inflammation and the like.

In an exemplary embodiment, the pharmaceutical formulation includes a simple solution. In an exemplary embodiment, the simple solution includes a polyether. In an exemplary embodiment, the polyether is polyethylene glycol or polypropylene glycol. In an exemplary embodiment, the simple solution includes an alcohol. In an exemplary embodiment, the alcohol is methanol, ethanol, propanol, isopropanol or butanol. In an exemplary embodiment, the simple solution includes a polyether and an alcohol. In another exemplary embodiment, the simple solution includes a polypropylene glycol and ethanol. In another exemplary embodiment, the simple solution is a member selected from about 10% polypropylene glycol and about 90% ethanol; about 20% polypropylene glycol and about 80% ethanol; about 30% polypropylene glycol and about 70% ethanol; about 40% polypropylene glycol and about 60% ethanol; about 50% polypropylene glycol and about 50% ethanol; about 60% polypropylene glycol and about 40% ethanol; about 70% polypropylene glycol and about 30% ethanol; about 80% polypropylene glycol and about 20% ethanol; about 90% polypropylene glycol and about 10% ethanol.

In an exemplary embodiment, the pharmaceutical formulation is a lacquer.

V. b) Additional Active Agents

The following are examples of the cosmetic and pharmaceutical agents that can be added to the topical pharmaceutical formulations of the present invention.

The following agents are known compounds and are readily available commercially.

Anti-inflammatory agents include, but are not limited to, bisabolol, mentholatum, dapsone, aloe, hydrocortisone, and the like.

Vitamins include, but are not limited to, Vitamin B, Vitamin E, Vitamin A, Vitamin D, and the like and vitamin derivatives such as tazarotene, calcipotriene, tretinoin, adapalene and the like.

Anti-aging agents include, but are not limited to, niacinamide, retinol and retinoid derivatives, AHA, Ascorbic acid, lipoic acid, coenzyme Q 10, beta hydroxy acids, salicylic acid, copper binding peptides, dimethylaminoethyl (DAEA), and the like.

Sunscreens and or sunburn relief agents include, but are not limited to, PABA, jojoba, aloe, padimate-O, methoxycinnamates, proxamine HCl, lidocaine and the like. Sunless tanning agents include, but are not limited to, dihydroxyacetone (DHA).

Psoriasis-treating agents and/or acne-treating agents include, but are not limited to, salicylic acid, benzoyl peroxide, coal tar, selenium sulfide, zinc oxide, pyrithione (zinc and/or sodium), tazarotene, calcipotriene, tretinoin, adapalene and the like.

Agents that are effective to control or modify keratinization, including without limitation: tretinoin, tazarotene, and adapalene.

The compositions comprising an compound/active agent described herein, such as for example in Formula (I) or Formula (II), and optionally at least one of these additional agents, are to be administered topically. In a primary application, this leads to the compounds of the invention and any other active agent working upon and treating the skin, nail, hair, claw or hoof. Alternatively, any one of the topically applied active agents may also be delivered systemically by transdermal routes.

In such compositions an additional cosmetically or pharmaceutically effective agent, such as an anti-inflammatory agent, vitamin, anti-aging agent, sunscreen, and/or acne-treating agent, for example, is usually a minor component (from about 0.001% to about 20% by weight or preferably from about 0.01% to about 10% by weight) with the remainder being various vehicles or carriers and processing aids helpful for forming the desired dosing form.

V. c) Testing

Preferred compounds for use in the present topical formulations will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat. B*677: 1-27). Compound half-life is inversely proportional to the frequency of dosage of a compound. In vitro half-lives of compounds may be predicted from assays of microsomal half-life as described by Kuhnz and Gleschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

V. d) Administration

For any compound used in the method of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, i.e., the concentration of the test compound which achieves a half-maximal inhibition of bacterial cell growth. Such information can be used to more accurately determine useful doses in humans.

In general, the compounds prepared by the methods, and from the intermediates, described herein will be administered in a therapeutically or cosmetically effective amount by any of the accepted modes of administration for agents that serve similar utilities. It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Dosage amount and interval can be adjusted individually to provide plasma levels of the active moiety that are sufficient to maintain bacterial cell growth inhibitory effects. Usual patient dosages for systemic administration range from 0.1 to 1000 mg/day, preferably, 1-500 mg/day, more preferably 10-200 mg/day, even more preferably 100-200 mg/day. Stated in terms of patient body surface areas, usual dosages range from 50-91 mg/m$^2$/day.

The amount of the compound in a formulation can vary within the full range employed by those skilled in the art. Typically, the formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

The invention is further illustrated by the Examples that follow. The Examples are not intended to define or limit the scope of the invention.

EXAMPLES

Proton NMR are recorded on Varian AS 300 spectrometer and chemical shifts are reported as δ (ppm) down field from tetramethylsilane. Mass spectra are determined on Micromass Quattro II.

Example 1

Preparation of 3 from 1

1.1 Reduction of Carboxylic Acid

To a solution of 1 (23.3 mmol) in anhydrous THF (70 mL) under nitrogen was added dropwise a BH$_3$ THF solution (1.0 M, 55 mL, 55 mmol) at 0° C. and the reaction mixture was stirred overnight at room temperature. Then the mixture was cooled again with ice bath and MeOH (20 mL) was added dropwise to decompose excess BH$_3$. The resulting mixture was stirred until no bubble was released and then 10% NaOH (10 mL) was added. The mixture was concentrated and the residue was mixed with water (200 mL) and extracted with EtOAc. The residue from rotary evaporation was purified by flash column chromatography over silica gel to give 20.7 mmol of 3.

1.2 Results

Exemplary compounds of structure 3 prepared by the method above are provided below.

1.2.a 2-Bromo-5-chlorobenzyl Alcohol $^1$H NMR (300 MHz, DMSO-d$_6$): δ 7.57 (d, J=8.7 Hz, 1H), 7.50-7.49 (m, 1H), 7.28-7.24 (m, 1H), 5.59 (t, J=6.0 Hz, 1H) and 4.46 (d, J=6.0 Hz, 2H) ppm.

1.2.b 2-Bromo-5-methoxybenzyl Alcohol $^1$H NMR (300 MHz, DMSO-d$_6$): δ 7.42 (d, J=8.7 Hz, 1H), 7.09 (d, J=2.4 Hz, 1H), 6.77 (dd, J$_1$=3 Hz, J$_2$=3 Hz, 1H), 5.43 (t, J=5.7 Hz, 1H), 4.44 (d, J=5.1 Hz, 2H), 3.76 (s, 3H).

Example 2

Preparation of 3 from 2

2.1. Reduction of Aldehyde

To a solution of 2 (Z=H, 10.7 mmol) in methanol (30 mL) was added sodium borohydride (5.40 mol), and the mixture was stirred at room temperature for 1 h. Water was added, and the mixture was extracted with ethyl acetate. The organic layer was washed with brine and dried on anhydrous sodium sulfate. The solvent was removed under reduced pressure to afford 9.9 mmol of 3.

2.2 Results

Exemplary compounds of structure 3 prepared by the method above are provided below.

2.2.a 2-Bromo-5-(4-cyanophenoxy)benzyl Alcohol $^1$H-NMR (300 MHz, CDCl$_3$) δ (ppm) 2.00 (br s, 1H), 4.75 (s, 2H), 6.88 (dd, J=8.5, 2.9 Hz, 1H), 7.02 (d, J=8.8 Hz, 1H), 7.26 (d, J=2.6 Hz, 1H), 7.56 (d, J=8.5 Hz, 1H), 7.62 (d, J=8.8 Hz, 2H).

2.2.b 2-Bromo-4-(4-cyanophenoxy)benzyl Alcohol $^1$H NMR (300 MHz, DMSO-d$_6$): δ 7.83 (d, 2H), 7.58 (d, 1H), 7.39 (d, 1H), 7.18 (dd, 1H), 7.11 (d, 2H), 5.48 (t, 1H) and 4.50 (d, 2H) ppm.

2.2.c 5-(4-Cyanophenoxy)-1-Indanol

M.p. 50-53° C. MS (ESI+): m/z=252 (M+1). HPLC: 99.7% purity at 254 nm and 99.0% at 220 nm. $^1$H NMR (300 MHz, DMSO-d$_6$): δ 7.80 (d, 2H), 7.37 (d, 1H), 7.04 (d, 2H), 6.98-6.93 (m, 2H), 5.27 (d, 1H), 5.03 (q, 1H), 2.95-2.85 (m, 1H), 2.75-2.64 (m, 1H), 2.39-2.29 (m, 1H) and 1.85-1.74 (m, 1H) ppm.

2.2. d 2-Bromo-5-(tert-butyldimethylsiloxy)benzyl Alcohol $^1$H-NMR (300 MHz, CDCl$_3$) δ (ppm) 0.20 (s, 6H), 0.98 (s, 9H), 4.67 (br s, 1H), 6.65 (dd, J=8.2, 2.6 Hz, 1H), 6.98 (d, J=2.9 Hz, 1H), 7.36 (d, J=8.8 Hz, 1H).

Additional examples of compounds which can be produced by this method include 2-bromo-4-(3-cyanophenoxy) benzyl alcohol; 2-bromo-4-(4-chlorophenoxy)benzyl alcohol; 2-bromo-4-phenoxybenzyl alcohol; 2-bromo-5-(3,4-dicyanophenoxy)benzyl alcohol; 2-(2-bromo-5-fluorophenyl)ethyl alcohol; 2-bromo-5-fluorobenzyl alcohol; and 1-bromo-2-naphthalenemethanol.

Example 3

Preparation of 4 from 3

3.1 Protective Alkylation

Compound 3 (20.7 mmol) was dissolved in CH$_2$Cl$_2$ (150 mL) and cooled to 0° C. with ice bath. To this solution under nitrogen were added in sequence N,N-di-isopropyl ethyl amine (5.4 mL, 31.02 mmol, 1.5 eq) and chloromethyl methyl ether (2 mL, 25.85 mmol, 1.25 eq). The reaction mixture was stirred overnight at room temperature and washed with NaHCO$_3$-saturated water and then NaCl-saturated water. The residue after rotary evaporation was purified by flash column chromatography over silica gel to give 17.6 mmol of 4.

3.2 Results

Exemplary compounds of structure 4 prepared by the method above are provided below.

3.2.a 2-Bromo-5-chloro-1-(methoxymethoxymethyl)benzene $^1$H NMR (300 MHz, DMSO-d$_6$): δ 7.63 (d, J=8.7 Hz, 1H), 7.50 (dd, J=2.4 & 0.6 Hz, 1H), 7.32 (dd, J=8.4 & 2.4 Hz, 1H), 4.71 (s, 2H), 4.53 (s, 2H) and 3.30 (s, 3H) ppm.

3.2.b 2-Bromo-5-fluoro-1-[1-(methoxymethoxy)ethyl]benzene $^1$H-NMR (300.058 MHz, CDCl$_3$) δ ppm 1.43 (d, J=6.5 Hz, 3H), 3.38 (s, 3H), 4.55 (d, J=6.5 Hz, 1H), 4.63 (d, J=6.5 Hz, 1H), 5.07 (q, J=6.5 Hz, 1H), 6.85 (m, 1H), 7.25 (dd, J=9.7, 2.6 Hz, 1H), 7.46 (dd, J=8.8, 5.3 Hz, 1H).

3.2.c 2-Bromo-5-fluoro-1-[2-(methoxymethoxy)ethyl]benzene

¹H-NMR (300.058 MHz, CDCl₃) δ ppm 3.04 (t, J=6.7 Hz, 2H), 3.31 (s, 3H), 3.77 (t, J=6.7 Hz, 2H), 4.62 (s, 2H), 6.82 (td, J=8.2, 3.2 Hz, 1H), 7.04 (dd, J=9.4, 2.9 Hz, 1H), 7.48 (dd, J=8.8, 5.3 Hz, 1H).

3.2.d 2-Bromo-4,5-difluoro-1-(methoxymethoxymethyl)benzene

¹H-NMR (300.058 MHz, CDCl₃) δ ppm 3.42 (s, 3H), 4.57 (d, J=1.2 Hz, 2H), 4.76 (s, 2H), 7.3-7.5 (m, 2H).

3.2.e 2-Bromo-5-cyano-1-(methoxymethoxymethyl)benzene

¹H-NMR (300.058 MHz, CDCl₃) δ ppm 3.43 (s, 3H), 4.65 (s, 2H), 4.80 (s, 2H), 7.43 (dd, J=8.2, 4.1 Hz, 1H), 7.66 (d, J=8.2 Hz, 1H), 7.82 (d, J=4.1 Hz, 1H).

3.2.f 2-Bromo-5-methoxy-1-(methoxymethoxymethyl)benzene

¹H NMR (300 MHz, DMSO-d₆): δ 7.48 (dd, J₁=1.2 Hz, J₂=1.2 Hz, 1H), 7.05 (d, J=2.7 Hz, 1H), 6.83 (dd, J₁=3 Hz, J₂=3 Hz, 1H), 4.69 (d, J=1.2 Hz, 2H), 4.5 (s, 2H), 3.74 (d, J=1.5 Hz, 3H), 3.32 (d, J=2.1 Hz, 3H) ppm.

3.2.g 1-Benzyl-1-(2-bromophenyl)-1-(methoxymethoxy)ethane

¹H NMR (300 MHz, DMSO-d₆): δ 7.70-7.67 (m, 1H), 7.25-7.09 (m, 6H), 6.96-6.93 (m, 2H), 4.61 (d, 1H), 4.48 (d, 1H), 3.36-3.26 (m, 2H), 3.22 (s, 3H) and 1.63 (s, 3H) ppm.

3.2.h 2-Bromo-6-fluoro-1-(methoxymethoxymethyl)benzene

¹H-NMR (300 MHz, CDCl₃) δ (ppm) 3.43 (s, 3H), 4.74 (s, 2H), 4.76 (d, J=2.1 Hz, 2H), 7.05 (t, J=9.1 Hz, 1H), 7.18 (td, J=8.2, 5.9 Hz, 1H), 7.40 (d, J=8.2 Hz, 1H).

3.2.i 2-Bromo-4-(4-cyanophenoxy)-1-(methoxymethoxymethyl)benzene

¹H NMR (300 MHz, DMSO-d₆): δ 7.84 (d, 2H), 7.56 (d, 1H), 7.44 (d, 1H), 7.19-7.12 (m, 3H), 4.69 (s, 2H), 4.56 (s, 2H) and 3.31 (s, 3H) ppm.

3.2.j 2-Bromo-5-(tert-butyldimethylsiloxy)-1-(methoxymethoxymethyl)benzene

¹H-NMR (300 MHz, CDCl₃) δ (ppm) 0.19 (s, 6H), 0.98 (s, 9H), 3.43 (s, 3H), 4.59 (s, 2H), 4.75 (s, 2H), 6.64 (dd, J=8.5, 2.9 Hz, 1H), 6.98 (d, J=2.9 Hz, 1H), 7.36 (d, J=8.5 Hz, 1H).

3.2.k 2-Bromo-5-(2-cyanophenoxy)-1-(methoxymethoxymethyl)benzene

¹H-NMR (300 MHz, CDCl₃) δ (ppm) 3.41 (s, 3H), 4.64 (s, 2H), 4.76 (s, 2H), 6.8-6.9 (m, 2H), 7.16 (td, J=7.6, 0.9 Hz, 1H), 7.28 (d, J=2.9 Hz, 1H), 7.49 (ddd, J=8.8, 7.6, 1.8 Hz, 1H), 7.56 (d, J=8.5 Hz, 1H), 7.67 (dd, J=7.9, 1.8 Hz, 1H).

3.2.l 2-Bromo-5-phenoxy-1-(methoxymethoxymethyl)benzene

¹H-NMR (300 MHz, CDCl₃) δ (ppm) 3.40 (s, 3H), 4.62 (s, 2H), 4.74 (s, 2H), 6.80 (dd, J=8.8, 2.9 Hz, 1H), 7.01 (d, J=8.5 Hz, 2H), 7.12 (t, J=7.9 Hz, 1H), 7.19 (d, J=2.9 Hz, 1H), 7.35 (t, J=7.6 Hz, 2H), 7.48 (d, J=8.5 Hz, 1H).

Additional examples of compounds which can be produced by this method include 2-bromo-1-(methoxymethoxymethyl)benzene; 2-bromo-5-methyl-1-(methoxymethoxymethyl)benzene; 2-bromo-5-(methoxymethoxymethyl)-1-(methoxymethoxymethyl)benzene; 2-bromo-5-fluoro-1-(methoxymethoxymethyl)benzene; 1-bromo-2-(methoxymethoxymethyl)naphthalene; 2-bromo-4-fluoro-1-(methoxymethoxymethyl)benzene; 2-phenyl-(2-bromophenyl)-1-(methoxymethoxy)ethane; 2-bromo-5-(4-cyanophenoxy)-1-(methoxymethoxy methyl)benzene; 2-bromo-4-(3-cyanophenoxy)-1-(methoxymethoxymethyl)benzene; 2-bromo-4-(4-chlorophenoxy)-1-(methoxymethoxymethyl)benzene; 2-bromo-4-phenoxy-1-(methoxymethoxymethyl)benzene; 2-bromo-5-(3,4-dicyanophenoxy)-1-(methoxymethoxymethyl)benzene.

Example 4

Preparation of I from 4 Via 5

4.1 Metallation and Boronylation

To a solution of 4 (17.3 mmol) in anhydrous THF (80 mL) at −78° C. under nitrogen was added dropwise tert-BuLi or n-BuLi (11.7 mL) and the solution became brown colored. Then, B(OMe)₃ (1.93 mL, 17.3 mmol) was injected in one portion and the cooling bath was removed. The mixture was warmed gradually with stirring for 30 min and then stirred with a water bath for 2 h. After addition of 6N HCl (6 mL), the mixture was stirred overnight at room temperature and about 50% hydrolysis has happened as shown by TLC analysis. The solution was rotary evaporated and the residue was dissolved in MeOH (50 mL) and 6N HCl (4 mL). The solution was refluxed for 1 h and the hydrolysis was completed as indicated by TLC analysis. Rotary evaporation gave a residue which was dissolved in EtOAc, washed with water, dried and then evaporated. The crude product was purified by flash column chromatography over silica gel to provide a solid with 80% purity. The solid was further purified by washing with hexane to afford 7.2 mmol of I.

4.2 Results

Analytical data for exemplary compounds of structure I are provided below.

4.2.a 5-Chloro-1,3-dihydro-1-hydroxy-2,1-benzoxaborole (C1)

M.p. 142-150° C. MS (ESI): m/z=169 (M+1, positive) and 167 (M−1, negative). HPLC (220 nm): 99% purity. ¹H NMR (300 MHz, DMSO-d₆): δ 9.30 (s, 1H), 7.71 (d, J=7.8 Hz, 1H), 7.49 (s, 1H), 7.38 (d, J=7.8 Hz, 1H) and 4.96 (s, 2H) ppm.

4.2.b 1,3-Dihydro-1-hydroxy-2,1-benzoxaborole (C2)

M.p. 83-86° C. MS (ESI): m/z=135 (M+1, positive) and 133 (M−1, negative). HPLC (220 nm): 95.4% purity. ¹H NMR (300 MHz, DMSO-d₆): δ 9.14 (s, 1H), 7.71 (d, J=7.2 Hz, 1H), 7.45 (t, J=7.5 Hz, 1H), 7.38 (d, J=7.5 Hz, 1H), 7.32 (t, J=7.1 Hz, 1H) and 4.97 (s, 2H) ppm.

4.2.c 5-Fluoro-1,3-dihydro-1-hydroxy-3-methyl-2,1-benzoxaborole (C3)

¹H-NMR (300 MHz, DMSO-d₆) δ ppm 1.37 (d, J=6.4 Hz, 3H), 5.17 (q, J=6.4 Hz, 1H), 7.14 (m, 1H), 7.25 (dd, J=9.7, 2.3 Hz, 1H), 7.70 (dd, J=8.2, 5.9 Hz, 1H), 9.14 (s, 1H).

4.2.d 6-Fluoro-1-hydroxy-1,2,3,4-tetrahydro-2,1-benzoxaborine (C4)

¹H-NMR (300 MHz, DMSO-d₆) δ ppm 2.86 (t, J=5.9 Hz, 2H), 4.04 (t, J=5.9 Hz, 2H), 7.0-7.1 (m, 2H), 7.69 (dd, J=8.2, 7.2 Hz, 1H), 8.47 (s, 1H).

4.2.e 5,6-Difluoro-1,3-dihydro-1-hydroxy-2,1-benzoxaborole (C5)

¹H-NMR (300 MHz, DMSO-d₆) δ ppm 4.94 (s, 2H), 7.50 (dd, J=10.7, 6.8 Hz, 1H), 7.62 (dd, J=9.7, 8.2 Hz, 1H), 9.34 (s, 1H).

4.2.f 5-Cyano-1,3-dihydro-1-hydroxy-2,1-benzoxaborole (C6)

¹H-NMR (300 MHz, DMSO-d₆) δ ppm 5.03 (s, 2H), 7.76 (d, J=8.2 Hz, 1H), 7.89 (d, J=8.2 Hz, 1H), 7.90 (s, 1H), 9.53 (s, 1H).

4.2.g 1,3-Dihydro-1-hydroxy-5-methoxy-2,1-benzoxaborole (C7)

M.p. 102-104° C. MS ESI: m/z=165.3 (M+1) and 162.9 (M−1). ¹H NMR (300 MHz, DMSO-d₆): δ 8.95 (s, 1H), 7.60 (d, J=8.1 Hz, 1H), 6.94 (s, 1H), 6.88 (d, J=8.1 Hz, 1H), 4.91 (s, 2H), 3.77 (s, 3H) ppm.

4.2.h 1,3-Dihydro-1-hydroxy-5-methyl-2,1-benzoxaborole (C8)

M.p. 124-128° C. MS ESI: m/z=148.9 (M+1) and 146.9 (M−1). $^1$H NMR (300 MHz, DMSO-d$_6$): δ 9.05 (s, 1H), 7.58 (d, J=7.2 Hz, 1H), 7.18 (s, 1H), 7.13 (d, J=7.2 Hz, 1H), 4.91 (s, 2H), 2.33 (s, 3H) ppm.

4.2.i 1,3-Dihydro-1-hydroxy-5-hydroxymethyl-2,1-benzoxaborole (C9)

MS: m/z=163 (M−1, ESI−). $^1$H NMR (300 MHz, DMSO-d$_6$): δ 9.08 (s, 1H), 7.64 (d, 1H), 7.33 (s, 1H), 7.27 (d, 1H), 5.23 (t, 1H), 4.96 (s, 2H), 4.53 (d, 2H) ppm.

4.2.j 1,3-Dihydro-5-fluoro-1-hydroxy-2,1-benzoxaborole (C10)

M.p. 110-114° C. MS ESI: m/z=150.9 (M−1). $^1$H NMR (300 MHz, DMSO-d$_6$): δ 9.20 (s, 1H), 7.73 (dd, J$_1$=6 Hz, J$_2$=6 Hz, 1H), 7.21 (m, 1H), 7.14 (m, 1H), 4.95 (s, 2H) ppm.

4.2.k 1,3-Dihydro-2-oxa-1-cyclopenta[α]naphthalene (C11)

M.P. 139-143° C. MS ESI: m/z=184.9 (M+1). $^1$H NMR (300 MHz, DMSO-d$_6$): δ 9.21 (s, 1H), 8.28 (dd, J$_1$=6.9 Hz, J$_2$=0.6 Hz, 1H), 7.99 (d, J=8.1 Hz, 1H), 7.95 (d, J=7.5 Hz, 1H), 7.59-7.47 (m, 3H), 5.09 (s, 2H) ppm.

4.2.l 7-Hydroxy-2,1-oxaborolano[5,4-c]pyridine (C12)

$^1$H-NMR (300 MHz, DMSO-d$_6$): δ ppm 5.00 (s, 2H), 7.45 (d, J=5.0 Hz, 1H), 8.57 (d, J=5.3 Hz, 1H), 8.91 (s, 1H), 9.57 (s, 1H). ESI-MS m/z 134 (M−H)$^−$, C$_6$H$_6$BNO$_2$=135.

4.2.m 1,3-Dihydro-6-fluoro-1-hydroxy-2,1-benzoxaborole (C13)

M.p. 110-117.5° C. MS (ESI): m/z=151 (M−1, negative). HPLC (220 nm): 100% purity. $^1$H NMR (300 MHz, DMSO-d$_6$): δ 9.29 (s, 1H), 7.46-7.41 (m, 2H), 7.29 (td, 1H) and 4.95 (s, 2H) ppm.

4.2.n 3-Benzyl-1,3-dihydro-1-hydroxy-3-methyl-2,1-benzoxaborole (C14)

MS (ESI): m/z=239 (M+1, positive). HPLC: 99.5% purity at 220 nm and 95.9% at 254 nm. $^1$H NMR (300 MHz, DMSO-d$_6$): δ 8.89 (s, 1H), 7.49-7.40 (m, 3H), 7.25-7.19 (m, 1H), 7.09-7.05 (m, 3H), 6.96-6.94 (m, 2H), 3.10 (d, 1H), 3.00 (d, 1H) and 1.44 (s, 3H) ppm.

4.2.o 3-Benzyl-1,3-dihydro-1-hydroxy-2,1-benzoxaborole (C15)

MS (ESI+): m/z=225 (M+1). HPLC: 93.4% purity at 220 nm. $^1$H NMR (300 MHz, DMSO-d$_6$): δ 9.08 (s, 1H), 7.63 (dd, 1H), 7.43 (t, 1H), 7.35-7.14 (m, 7H), 5.38 (dd, 1H), 3.21 (dd, 1H) and 2.77 (dd, 1H) ppm.

4.2.p 1,3-Dihydro-4-fluoro-1-hydroxy-2,1-benzoxaborole (C16)

$^1$H-NMR (300 MHz, DMSO-d$_6$) δ (ppm) 5.06 (s, 2H), 7.26 (ddd, J=9.7, 7.9, 0.6 Hz, 1H), 7.40 (td, J=8.2, 4.7 Hz, 1H), 7.55 (d, J=7.0 Hz, 1H), 9.41 (s, 1H).

4.2.q 5-(4-Cyanophenoxy)-1,3-dihydro-1-hydroxy-2,1-benzoxaborole (C17)

$^1$H-NMR (300 MHz, DMSO-d$_6$) δ ppm 4.95 (s, 2H), 7.08 (dd, J=7.9, 2.1 Hz, 1H), 7.14 (d, J=8.8 Hz, 1H), 7.15 (d, J=2.1 Hz, 1H), 7.78 (d, J=7.9 Hz, 1H), 7.85 (d, J=9.1 Hz, 2H), 9.22 (s, 1H).

4.2.r 6-(4-Cyanophenoxy)-1,3-dihydro-1-hydroxy-2,1-benzoxaborole (C18)

M.p. 148-151° C. MS: m/z=252 (M+1) (ESI+) and m/z=250 (M−1) (ESI−). HPLC: 100% purity at 254 nm and 98.7% at 220 nm. $^1$H NMR (300 MHz, DMSO-d$_6$): δ 9.26 (s, 1H), 7.82 (d, 2H), 7.50 (d, 1H), 7.39 (d, 1H), 7.26 (dd, 1H), 7.08 (d, 2H) and 4.99 (s, 2H) ppm 4.2.s 6-(3-Cyanophenoxy)-1,3-dihydro-1-hydroxy-2,1-benzoxaborole (C19)

M.p. 146-149° C. MS: m/z=252 (M+1) (ESI+) and m/z=250 (M−1) (ESI−). HPLC: 100% purity at 254 nm and 97.9% at 220 nm. $^1$H NMR (300 MHz, DMSO-d$_6$): δ 9.21 (s, 1H), 7.60-7.54 (m, 2H), 7.50-7.45 (m, 2H), 7.34-7.30 (m, 2H), 7.23 (dd, 1H) and 4.98 (s, 2H) ppm.

4.2.t 6-(4-Chlorophenoxy)-1,3-dihydro-1-hydroxy-2,1-benzoxaborole (C20)

M.p. 119-130° C. MS: m/z=261 (M+1) (ESI+) and m/z=259 (M−1) (ESI−). HPLC: 100% purity at 254 nm and 98.9% at 220 nm. $^1$H NMR (300 MHz, DMSO-d$_6$): δ 9.18 (s, 1H), 7.45-7.41 (m, 3H), 7.29 (d, 1H), 7.19 (dd, 1H), 7.01 (d, 2H) and 4.96 (s, 2H) ppm.

4.2.u 6-Phenoxy-1,3-dihydro-1-hydroxy-2,1-benzoxaborole (C21)

M.p. 95-99° C. MS: m/z=227 (M+1) (ESI+) and m/z=225 (M−1) (ESI−). HPLC: 100% purity at 254 nm and 98.4% at 220 nm. $^1$H NMR (300 MHz, DMSO-d$_6$): δ 9.17 (s, 1H), 7.43-7.35 (m, 3H), 7.28 (s, 1H), 7.19-7.09 (m, 2H), 6.99 (d, 2H) and 4.96 (s, 2H) ppm.

4.2.v 5-(4-Cyanobenzyloxy)-1,3-dihydro-1-hydroxy-2,1-benzoxaborole (C22)

$^1$H-NMR (300 MHz, DMSO-d$_6$) δ (ppm) 4.90 (s, 2H), 5.25 (s, 2H), 6.98 (dd, J=7.9, 2.1 Hz, 1H), 7.03 (d, J=1.8 Hz, 1H), 7.62 (d, J=7.9 Hz, 1H), 7.64 (d, J=8.5 Hz, 2H), 7.86 (d, J=8.5 Hz, 1H), 9.01 (s, 1H).

4.2.w 5-(2-Cyanophenoxy)-1,3-dihydro-1-hydroxy-2,1-benzoxaborole (C23)

$^1$H-NMR (300 MHz, DMSO-d$_6$) δ (ppm) 4.95 (s, 2H), 7.0-7.2 (m, 3H), 7.32 (td, J=7.6, 1.2 Hz, 1H), 7.68 (ddd, J=9.1, 7.6, 1.8 Hz, 1H), 7.77 (d, J=7.9 Hz, 1H), 7.91 (dd, J=7.9, 1.8 Hz, 1H).

4.2.x 5-Phenoxy-1,3-dihydro-1-hydroxy-2,1-benzoxaborole (C24)

$^1$H-NMR (300 MHz, DMSO-d$_6$) δ (ppm) 4.91 (s, 2H), 6.94 (s, 1H), 6.96 (d, J=8.8 Hz, 1H), 7.05 (d, J=7.6 Hz, 2H), 7.17 (t, J=7.3 Hz, 1H), 7.41 (t, J=7.3 Hz, 2H), 7.70 (d, J=8.5 Hz, 1H), 9.11 (s, 1H).

4.2.y 5-[4-(N,N-Diethylcarbamoyl)phenoxy]-1,3-dihydro-1-hydroxy-2,1-benzoxaborole (C25)

$^1$H-NMR (300 MHz, DMSO-d$_6$) δ (ppm) 1.08 (br s, 6H), 3.1-3.5 (m, 4H), 4.93 (s, 2H), 7.0-7.1 (m, 4H), 7.37 (d, J=8.5 Hz, 2H), 7.73 (d, J=7.9 Hz, 1H), 9.15 (s, 1H).

4.2.z 1,3-Dihydro-1-hydroxy-5-[4-(morpholinocarbonyl)phenoxy]-2,1-benzoxaborole (C26)

$^1$H-NMR (300 MHz, DMSO-d$_6$) δ (ppm) 3.3-3.7 (m, 8H), 4.93 (s, 2H), 7.0-7.1 (m, 4H), 7.44 (d, J=8.8 Hz, 2H), 7.73 (d, J=7.9 Hz, 1H), 9.16 (s, 1H).

4.2.aa 5-(3,4-Dicyanophenoxy)-1,3-dihydro-1-hydroxy-2,1-benzoxaborole (C27)

$^1$H-NMR (300 MHz, DMSO-d$_6$) δ (ppm) 4.97 (s, 2H), 7.13 (dd, J=7.9, 2.1 Hz, 1H), 7.21 (d, J=1.5 Hz, 1H), 7.43 (dd, J=8.8, 2.6 Hz, 1H), 7.81 (d, J=7.9 Hz, 1H), 7.82 (d, J=2.6 Hz, 1H), 8.11 (d, J=8.5 Hz, 1H), 9.26 (s, 1H).

4.2.ab 6-Phenylthio-1,3-dihydro-1-hydroxy-2,1-benzoxaborole (C28)

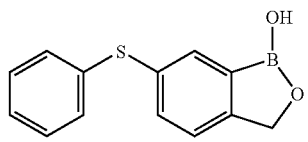

M.p. 121-124° C. MS: m/z=243 (M+1) (ESI+) and m/z=241 (M−1) (ESI−). HPLC: 99.6% purity at 254 nm and 99.6% at 220 nm. $^1$H NMR (300 MHz, DMSO-d$_6$): δ 9.25 (s, 1H), 7.72 (dd, 1H), 7.48 (dd, 1H), 7.43 (dd, 1H), 7.37-7.31 (m, 2H), 7.29-7.23 (m, 3H), and 4.98 (s, 2H) ppm.

4.2.ac 6-(4-trifluoromethoxyphenoxy)-1,3-dihydro-1-hydroxy-2,1-benzoxaborole (C29)

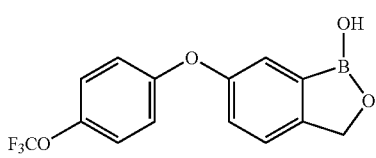

M.p. 97-101° C. MS: m/z=311 (M+1) (ESI+) and m/z=309 (M−1) (ESI−). HPLC: 100% purity at 254 nm and 100% at 220 nm. $^1$H NMR (300 MHz, DMSO-$d_6$): δ 9.20 (s, 1H), 7.45 (d, 1H), 7.37 (d, 2H), 7.33 (d, 1H), 7.21 (dd, 1H), 7.08 (d, 2H), and 4.97 (s, 2H) ppm.

4.2.ad 5-(N-Methyl-N-phenylsulfonylamino)-1,3-dihydro-1-hydroxy-2,1-benzoxaborole (C30)

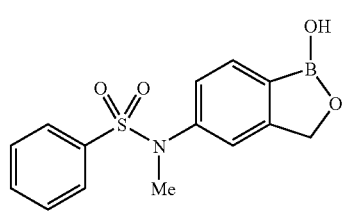

M.p. 85-95° C. MS: m/z=304 (M+1) (ESI+) and m/z=302 (M−1) (ESI−). HPLC: 96.6% purity at 254 nm and 89.8% at 220 nm. $^1$H NMR (300 MHz, DMSO-$d_6$): δ 9.23 (s, 1H), 7.72-7.63 (m, 2H), 7.56 (t, 2H), 7.50 (d, 2H), 7.16 (s, 1H), 7.03 (d, 1H), 4.91 (s, 2H) and 3.14 (s, 3H) ppm.

4.2.ae 6-(4-Methoxyphenoxy)-1,3-dihydro-1-hydroxy-2,1-benzoxaborole (C31)

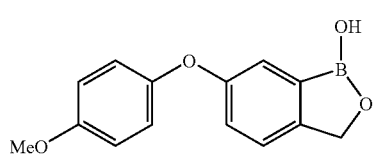

M.p. 126-129° C. MS: m/z=257 (M+1) (ESI+) and m/z=255 (M−1) (ESI−). HPLC: 98.4% purity at 254 nm and 98.4% at 220 nm. $^1$H NMR (300 MHz, DMSO-$d_6$): δ 9.14 (s, 1H), 7.36 (d, 1H), 7.19 (s, 1H), 7.12 (d, 1H), 6.98 (d, 2H), 6.95 (d, 2H), 4.93 (s, 2H) and 3.73 (s, 3H) ppm.

4.2.af 6-(4-Methoxyphenylthio)-1,3-dihydro-1-hydroxy-2,1-benzoxaborole (C32)

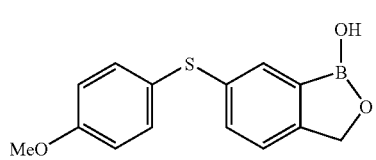

M.p. 95-100° C. MS: m/z=272 (M+), 273 (M+1) (ESI+) and m/z=271 (M−1) (ESI−). HPLC: 100% purity at 254 nm and 99.2% at 220 nm. $^1$H NMR (300 MHz, DMSO-$d_6$): δ 9.20 (s, 1H), 7.51 (d, 1H), 7.39-7.28 (m, 4H), 6.98 (d, 2H), 4.93 (s, 2H) and 3.76 (s, 3H) ppm.

4.2.ag 6-(4-Methoxyphenylsulfonyl)-1,3-dihydro-1-hydroxy-2,1-benzoxaborole (C33)

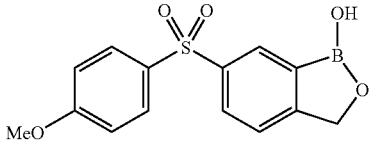

M.p. 180-192° C. MS: m/z=305 (M+1) (ESI+) and m/z=303 (M−1) (ESI−). HPLC: 96.8% purity at 254 nm and 95.5% at 220 nm. $^1$H NMR (300 MHz, DMSO-$d_6$): δ 9.46 (s, 1H), 8.28 (s, 1H), 7.99 (d, 1H), 7.85 (d, 2H), 7.61 (d, 1H), 7.11 (d, 2H), 5.02 (s, 2H) and 3.80 (s, 3H) ppm.

4.2.ah 6-(4-Methoxyphenylsulfinyl)-1,3-dihydro-1-hydroxy-2,1-benzoxaborole (C34)

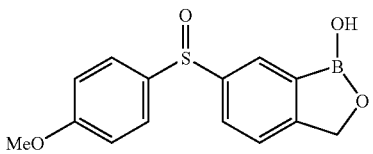

$^1$H NMR (300 MHz, DMSO-$d_6$): δ 9.37 (s, 1H), 8.02 (d, 1H), 7.71 (dd, 1H), 7.59 (d, 2H), 7.53 (d, 1H), 7.07 (d, 2H), 5.00 (s, 2H) and 3.76 (s, 3H) ppm.

4.2.ai 5-Trifluoromethyl-1,3-dihydro-1-hydroxy-2,1-benzoxaborole (C35)

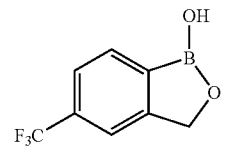

M.p. 113-118° C. MS: m/z=203 (M+1) (ESI+) and m/z=201 (M−1) (ESI−). HPLC: 100% purity at 254 nm and 100% at 220 nm. $^1$H NMR (300 MHz, DMSO-$d_6$): δ 9.48 (s, 1H), 7.92 (d, 1H), 7.78 (s, 1H), 7.67 (d, 1H) and 5.06 (s, 2H) ppm.

4.2.aj 4-(4-Cyanophenoxy)-1,3-dihydro-1-hydroxy-2,1-benzoxaborole (C36)

For coupling reaction between 4-fluorobenzonitrile and substituted phenol to give starting material 2, see Igarashi, S.; et al. *Chemical & Pharmaceutical Bulletin* (2000), 48(11), 1689-1697.

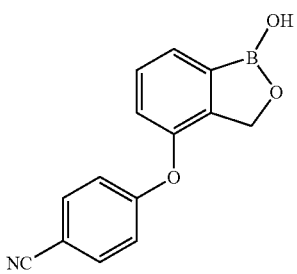

$^1$H-NMR (300 MHz, DMSO-$d_6$) (ppm) 4.84 (s, 2H), 7.08 (d, J=8.2 Hz, 2H), 7.18 (d, J=7.9 Hz, 1H), 7.45 (t, J=7.3 Hz, 1H), 7.63 (d, J=7.3 Hz, 1H), 7.82 (d, J=8.5 Hz, 2H).

7-(4-Cyanophenoxy)-1,3-dihydro-1-hydroxy-2,1-benzoxaborole (C100)

For coupling reaction between 4-fluorobenzonitrile and substituted phenol to give starting material 2, see Igarashi, S.; et al. *Chemical & Pharmaceutical Bulletin* (2000), 48(11), 1689-1697.

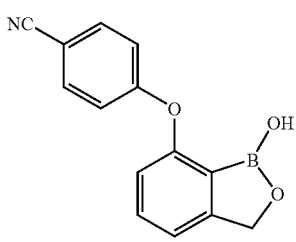

$^1$H NMR (300 MHz, DMSO-d$_6$) δ (ppm) 5.02 (s, 2H), 6.97 (d, J=7.9 Hz, 1H), 7.01 (d, J=8.5 Hz, 2H), 7.30 (d, J=7.3 Hz, 1H), 7.56 (t, J=7.6 Hz, 1H), 7.77 (d, J=8.5 Hz, 2H).

4.2.ak 5-(3-Cyanophenoxy)-1,3-dihydro-1-hydroxy-2,1-benzoxaborole (C37)

For coupling between 3-fluorobenzonitrile and substituted phenol to give starting material 2: Li, F. et al., *Organic Letters* (2003), 5(12), 2169-2171.

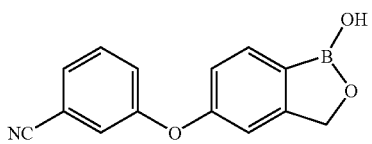

$^1$H-NMR (300 MHz, DMSO-d$_6$) (ppm) 4.93 (s, 2H), 7.0-7.1 (m, 2H), 7.3-7.4 (m, 1H), 7.5-7.7 (m, 3H), 7.75 (d, J=8.2 Hz, 1H).

4.2.al 5-(4-Carboxyphenoxy)-1-hydroxy-2,1-benzoxaborole (C38)

To a solution of 5-(4-cyanophenoxy)-1-hydroxy-2,1-benzoxaborole obtained in C17 (430 mg, 1.71 mmol) in ethanol (10 mL) was added 6 mol/L sodium hydroxide (2 mL), and the mixture was refluxed for 3 hours. Hydrochloric acid (6 mol/L, 3 mL) was added, and the mixture was extracted with ethyl acetate. The organic layer was washed with brine and dried on anhydrous sodium sulfate. The solvent was removed under reduced pressure, and the residue was purified by silica gel column chromatography (ethyl acetate) followed by trituration with diisopropyl ether to give the target compound (37 mg, 8%).

$^1$H-NMR (300 MHz, DMSO-d$_6$) δ (ppm) 4.94 (s, 2H), 7.0-7.1 (m, 4H), 7.76 (d, J=7.9 Hz, 1H), 7.94 (d, J=8.8 Hz, 2H), 9.19 (s, 1H), 12.8 (br s, 1H).

4.2.am 1-Hydroxy-5-[4-(tetrazole-1-yl)phenoxy]-2,1-benzoxaborole (C39)

A mixture of 5-(4-cyanophenoxy)-1-hydroxy-2,1-benzoxaborole (200 mg, 0.797 mmol), sodium azide (103 mg, 1.59 mmol), and ammonium chloride (85 mg, 1.6 mmol) in N,N-dimethylformamide (5 mL) was stirred at 80° C. for two days. Water was added, and the mixture was extracted with ethyl acetate. The organic layer was washed with water and brine, and dried on anhydrous sodium sulfate. The solvent was removed under reduced pressure, and the residue was purified by silica gel column chromatography (ethyl acetate) followed by trituration with ethyl acetate to give the target compound (55 mg, 23%).

$^1$H-NMR (300 MHz, DMSO-d$_6$) δ (ppm) 4.95 (s, 2H), 7.0-7.1 (m, 2H), 7.23 (d, J=8.8 Hz, 2H), 7.76 (d, J=7.9 Hz, 1H), 8.05 (d, J=8.5 Hz, 2H), 9.18 (br s, 1H).

Example 5

Preparation of I from 2 Via 6

5.1 Catalytic Boronylation, Reduction and Cyclization

A mixture of 2 (10.0 mmol), bis(pinacolato)diboron (2.79 g, 11.0 mmol), PdCl$_2$(dppf) (250 mg, 3 mol %), and potassium acetate (2.94 g, 30.0 mmol) in 1,4-dioxane (40 mL) was stirred at 80° C. for overnight. Water was added, and the mixture was extracted with ethyl acetate. The organic layer was washed with brine and dried on anhydrous sodium sulfate. The solvent was removed under reduced pressure. The crude product was dissolved in tetrahydrofuran (80 mL), then sodium periodate (5.56 g, 26.0 mmol) was added. After stirring at room temperature for 30 min, 2N HCl (10 mL) was added, and the mixture was stirred at room temperature for overnight. Water was added, and the mixture was extracted with ethyl acetate. The organic layer was washed with brine and dried on anhydrous sodium sulfate. The solvent was removed under reduced pressure, and the residue was treated with ether to afford 6.3 mmol of the corresponding boronic acid. To the solution of the obtained boronic acid (0.595 mmol) in methanol (5 mL) was added sodium borohydride (11 mg, 0.30 mmol), and the mixture was stirred at room temperature for 1 h. Water was added, and the mixture was extracted with ethyl acetate. The organic layer was washed with brine and dried on anhydrous sodium sulfate. The solvent was removed under reduced pressure, and the residue was purified by silica gel column chromatography to give 0.217 mmol of I.

5.2 Results

Analytical data for exemplary compounds of structure I are provided below.

5.2.a 1,3-Dihydro-5-fluoro-1-hydroxy-2,1-benzoxaborole (C10)

Analytical data for this compound is listed in 4.2.j.

Example 6

Preparation of I from 3

6.1 One-Pot Boronylation and Cyclization

To a solution of 3 (4.88 mmol) and triisopropyl borate (1.35 mL, 5.86 mmol) in tetrahydrofuran (10 mL) was added n-butyllithium (1.6 mol/L in hexanes; 6.7 mL, 10.7 mmol) dropwise over 15 min at −78° C. under nitrogen atmosphere, and the mixture was stirred for 2 h while allowing to warm to room temperature. The reaction was quenched with 2N HCl, and extracted with ethyl acetate. The organic layer was washed with brine and dried on anhydrous sodium sulfate. The solvent was removed under reduced pressure, and the residue was purified by silica gel column chromatography and treated with pentane to give 0.41 mmol of I.

6.2 Results

Analytical data for exemplary compounds of structure I are provided below.

6.2.a 1,3-Dihydro-5-fluoro-1-hydroxy-2,1-benzoxaborole (C10)

Analytical data for this compound is listed in 4.2.j.

Example 7

Preparation of I from 3

7.1 One-Pot Boronylation and Cyclization with Distillation

To a solution of 3 (4.88 mmol) in toluene (20 mL) was added triisopropyl borate (2.2 mL, 9.8 mmol), and the mixture was heated at reflux for 1 h. The solvent, the generated isopropyl alcohol and excess triisopropyl borate were removed under reduced pressure. The residue was dissolved in tetrahydrofuran (10 mL) and cooled to −78° C. n-Butyllithium (3.2 mL, 5.1 mmol) was added dropwise over 10 min, and the mixture was stirred for 1 h while allowing to warm to room temperature. The reaction was quenched with 2N HCl, and extracted with ethyl acetate. The organic layer was washed with brine and dried on anhydrous sodium sulfate. The solvent was removed under reduced pressure, and the residue was purified by silica gel column chromatography to give 1.54 mmol of I.

7.2 Results

Analytical data for exemplary compounds of structure I are provided below.

7.2.a 1,3-Dihydro-5-fluoro-1-hydroxy-2,1-benzoxaborole (C10)

Analytical data for this compound is listed in 4.2.j.

Example 8

Preparation of 8 from 7

8.1 Bromination

To a solution of 7 (49.5 mmol) in carbon tetrachloride (200 mL) were added N-bromosuccinimide (8.81 g, 49.5 mmol) and N,N-azoisobutylonitrile (414 mg, 5 mol %), and the mixture was heated at reflux for 3 h. Water was added, and the mixture was extracted with chloroform. The organic layer was washed with brine and dried on anhydrous sodium sulfate. The solvent was removed under reduced pressure to give the crude methyl-brominated intermediate 8.

Example 9

Preparation of 3 from 8

9.1 Hydroxylation

To crude 8 (49.5 mmol) were added dimethylformamide (150 mL) and sodium acetate (20.5 g, 250 mmol), and the mixture was stirred at 80° C. for overnight. Water was added, and the mixture was extracted with ether. The organic layer was washed with water and brine, and dried on anhydrous sodium sulfate. The solvent was removed under reduced pressure. To the residue was added methanol (150 mL) and 1N sodium hydroxide (50 mL), and the mixture was stirred at room temperature for 1 h. The reaction mixture was concentrated to about a third of volume under reduced pressure. Water and hydrochloric acid were added, and the mixture was extracted with ethyl acetate. The organic layer was washed with water and brine, and dried on anhydrous sodium sulfate. The solvent was removed under reduced pressure, and the residue was purified by silica gel column chromatography followed by trituration with dichloromethane to give 21.8 mmol of 3.

9.2 Results

Exemplary compounds of structure 3 prepared by the method above are provided below.

9.2.a 2-Bromo-5-cyanobenzyl Alcohol $^1$H-NMR (300 MHz, DMSO-$d_6$) δ ppm 4.51 (d, J=5.9 Hz, 2H), 5.67 (t, J=5.6 Hz, 1H), 7.67 (dd, J=8.2, 2.0 Hz, 1H), 7.80 (s, J=8.2 Hz, 1H), 7.83 (d, J=2.0 Hz, 1H).

Additional examples of compounds which can be produced by this method include 2-bromo-5-(4-cyanophenoxy) benzyl alcohol.

Example 10

Preparation of 9 from 2

10.1 Reaction

A mixture of 2 (20.0 mmol), (methoxymethyl)triphenylphosphonium chloride (8.49 g, 24.0 mmol), and potassium tert-butoxide (2.83 g, 24.0 mol) in N,N-dimethylformamide (50 mL) was stirred at room temperature for overnight. The reaction was quenched with 6 N HCl, and the mixture was extracted with ethyl acetate. The organic layer was washed with water (×2) and brine, and dried on anhydrous sodium sulfate. The solvent was removed under reduced. To the residue were added tetrahydrofuran (60 mL) and 6 N HCl, and the mixture was heated at reflux for 8 h. Water was added, and the mixture was extracted with ether. The organic layer was washed with brine and dried on anhydrous sodium sulfate. The solvent was removed under reduced pressure to afford 16.6 mmol of 9.

Example 11

Preparation Method of Step 13

11.1 Reaction

A solution of I in an appropriate alcohol solvent ($R^1$—OH) was refluxed under nitrogen atmosphere and then distilled to remove the alcohol to give the corresponding ester.

Example 12

Preparation of Ib from Ia 12.1 Reaction

To a solution of Ia in toluene was added amino alcohol and the participated solid was collected to give Ib.

12.2 Results (500 mg, 3.3 mmol) was dissolved in toluene (37 mL) at 80° C. and ethanolamine (0.20 mL, 3.3 mmol) was added. The mixture was cooled to room temperature, then ice bath, and filtered to give C38 as a white powder (600.5 mg, 94%).

12.2a (C38)

$^1$H-NMR (300 MHz, DMSO-$d_6$) δ (ppm) 2.88 (t, J=6.2 Hz, 2H), 3.75 (t, J=6.3 Hz, 2H), 4.66 (s, 2H), 5.77 (br, 2H), 6.85-6.91 (m, 2H), 7.31 (td, J=7.2, 1.2 Hz, 1H).

Example 13

5-(4-Carboxyphenoxy)-1-hydroxy-2,1-benzoxaborole

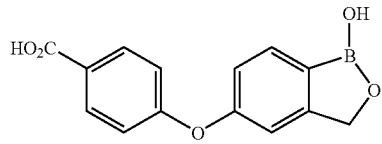

To a solution of 5-(4-cyanophenoxy)-1-hydroxy-2,1-benzoxaborole obtained in C17 (430 mg, 1.71 mmol) in ethanol (10 mL) was added 6 mol/L sodium hydroxide (2 mL), and the mixture was refluxed for 3 hours. Hydrochloric acid (6 mol/L, 3 mL) was added, and the mixture was extracted with ethyl acetate. The organic layer was washed with brine and dried on anhydrous sodium sulfate. The solvent was removed under reduced pressure, and the residue was purified by silica gel column chromatography (ethyl acetate) followed by trituration with diisopropyl ether to give the target compound (37 mg, 8%).

$^1$H-NMR (300 MHz, DMSO-$d_6$) δ (ppm) 4.94 (s, 2H), 7.0-7.1 (m, 4H), 7.76 (d, J=7.9 Hz, 1H), 7.94 (d, J=8.8 Hz, 2H), 9.19 (s, 1H), 12.8 (br s, 1H).

Example 14

1-Hydroxy-5-[4-(tetrazole-1-yl)phenoxy]-2,1-benzoxaborole

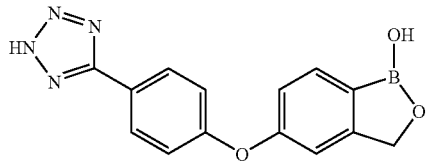

A mixture of 5-(4-cyanophenoxy)-1-hydroxy-2,1-benzoxaborole (200 mg, 0.797 mmol), sodium azide (103 mg, 1.59 mmol), and ammonium chloride (85 mg, 1.6 mmol) in N,N-dimethylformamide (5 mL) was stirred at 80° C. for two days. Water was added, and the mixture was extracted with ethyl acetate. The organic layer was washed with water and brine, and dried on anhydrous sodium sulfate. The solvent was removed under reduced pressure, and the residue was purified by silica gel column chromatography (ethyl acetate) followed by trituration with ethyl acetate to give the target compound (55 mg, 23%).

$^1$H-NMR (300 MHz, DMSO-$d_6$) δ (ppm) 4.95 (s, 2H), 7.0-7.1 (m, 2H), 7.23 (d, J=8.8 Hz, 2H), 7.76 (d, J=7.9 Hz, 1H), 8.05 (d, J=8.5 Hz, 2H), 9.18 (br s, 1H).

Example 15

4-(4-Cyanophenoxy)phenylboronic acid (C97)

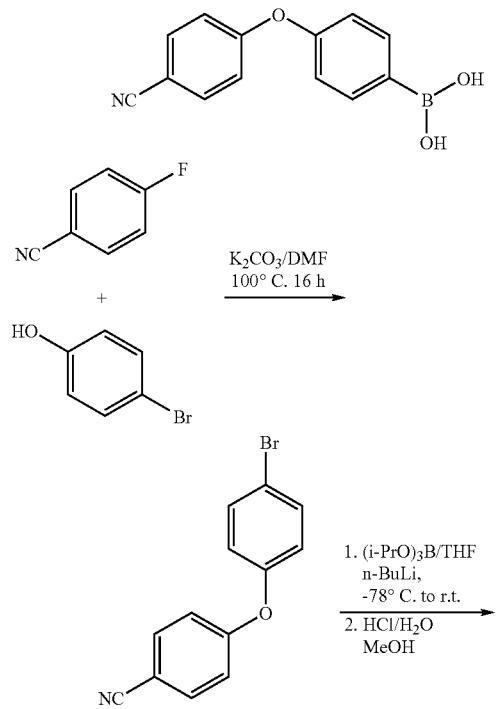

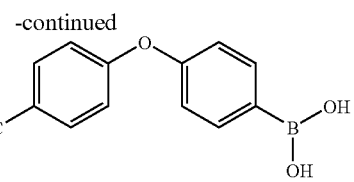

(a) (4-cyanophenyl)(4-bromophenyl)ether. Under nitrogen, the mixture of 4-fluorobenzonitrile (7.35 g, 60.68 mmol), 4-bromophenol (10 g, 57.8 mmol) and potassium carbonate (12 g, 1.5 eq) in DMF (100 mL) was stirred at 100° C. for 16 h and then filtered. After rotary evaporation, the residue was dissolved in ethyl acetate and washed with 1N NaOH solution to remove unreacted phenol. The organic solution was dried and passed through a short silica gel column to remove the color and minor phenol impurity. Evaporation of the solution gave (4-cyanophenyl)(4-bromophenyl) ether (13.82 g, yield 87.2%) as a white solid. $^1$H NMR (300 MHz, DMSO-$d_6$): δ 7.83 (d, 2H), 7.63 (d, 2H), 7.13 (d, 2H) and 7.10 (d, 2H) ppm.

(b) 4-(4-cyanophenoxy)phenylboronic acid. The procedure described in Example 2d was used for the synthesis of 4-(4-cyanophenoxy)phenylboronic acid using (4-cyanophenyl)(4-bromophenyl)ether as starting material. The title compound was obtained as a white solid. M.p. 194-198° C. MS: m/z=239 (M+), 240 (M+1) (ESI+) and m/z=238 (M−1) (ESI−). HPLC: 95.3% purity at 254 nm and 92.1% at 220 nm. $^1$H NMR (300 MHz, DMSO-$d_6$+$D_2O$): δ 7.83-7.76 (m, 4H), 7.07 (d, 2H) and 7.04 (d, 2H) ppm.

Example 16

3-(4-Cyanophenoxy)phenylboronic acid (C98)

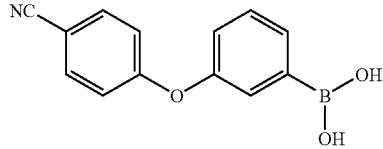

By following the procedures described for the synthesis of C21, the title compound was acquired from (4-cyanophenyl)(3-bromophenyl)ether that was prepared using 3-bromophenol and 4-fluorobenzonitrile as starting materials. The product was obtained as a white solid. M.p. 153-162° C. MS: m/z=239 (M+), 240 (M+1) (ESI+) and m/z=238 (M−1) (ESI−). HPLC: 98.5% purity at 254 nm and 97.5% at 220 nm. $^1$H NMR (300 MHz, DMSO-$d_6$+$D_2O$): δ 7.78 (d, 2H), 7.64 (d, 1H), 7.45-7.40 (m, 2H), 7.18-7.14 (dd, 1H) and 7.03 (d, 2H) ppm.

Example 17

4-(4-Cyanophenoxy)-2-Methylphenylboronic acid (C99)

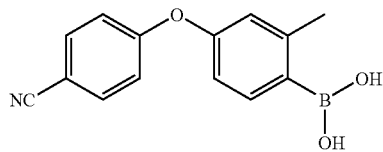

By following the procedures described for the synthesis of C21, the title compound was acquired from (4-cyanophenyl) (4-bromo-3-methylphenyl)ether that was prepared using 4-bromo-3-methylphenol and 4-fluorobenzonitrile as starting materials. The product was obtained as a cream solid. M.p. 161-165° C. MS: m/z=253 (M+), 254 (M+1) (ESI+) and m/z=252 (M−1) (ESI−). HPLC: 97.1% purity at 254 nm and 95.1% at 220 nm. $^1$H NMR (300 MHz, DMSO-$d_6$+$D_2O$): δ 7.95 (d, 2H), 7.81 (d, 1H), 7.09 (d, 2H), 6.92-6.88 (m, 2H) and 2.65 (s, 3H) ppm.

Example 18

Anti-Inflammatory Testing

The ability of the compounds of the invention to inhibit pro-inflammatory cytokines were tested. The effects of the compounds on IL-1β, IL-4, TNFα, and IFNγ cytokine release profiles in frozen human peripheral blood mononucleocytes (PBMC) was examined. PBMC cells were exposed to 10 μM concentration of each sample prior to stimulation with 20 μg/mL Phytohemagglutinins (PHA). Cytokine release profiles are assayed using the Luminex 4-plex assay. (IL-1β, IFNγ, IL-4, TNF-α). Results of the testing are provided in FIG. 1.
Methods:
Test Substances and Dosing Pattern
Frozen Human PBMC will be thawed and centrifuged. Cryopreservation media was aspirated off of the cell pellet, and the cells were resuspended in fresh culture media. The culture media (CM) for PBMC was RPMI 1640, 10% FBS, 1% P/S, 2 mM L-glutamine. Cells were incubated at 37° C., 5% $CO_2$. Dissolve dry solid compound described herein, such as according to Formula (I) or Formula (II) in DMSO to form a 20 mM sample (DMSO, 100%). The 20 mM samples were diluted to 200 μM (10×) in CM (DMSO, 1%). 10 μL of diluted sample was added to 190 uL CM+cells (n=3) for a final sample concentration of 10 μM (Final DMSO 0.05%). The sample was incubated with the cells at 37° C. for 15-30 mins prior to adding inducer (PHA, 20 ug/mL). Inducer plus a vehicle (PHA+0.05% DMSO) was used as a control for this experiment. Vehicle without inducer was used as a negative control. Dexamethasone (50 nM, n=3) was used in the positive control. Supernatant were extracted at 24 hours as well as 48 hours, and stored at −80° C. The supernatant was thawed, and assayed with Alamar Blue for sample cytotoxicity. The supernatant were then assayed for IL-1β, IL-4, TNF-α and IFNγ using the Luminex 4-plex assay.
Results:
Dexamethazone inhibition of cytokine secretion was within the expected range confirming that the assay was valid. % inhibition of IL-1β, IL-4, TNF-α and IFNγ for the various compounds of the invention are provided in FIG. 1.

Example 19

Topical, Phorbol Ester Mouse Ear Assay

Methods:
Test Substances and Dosing Pattern
5-(4-Cyanophenoxy)-1-hydroxy-2,1-dihydrobenzoxaborole and betamethasone were provided by Anacor Pharmaceuticals, Inc. Betamethasone is used to treat the itching, redness, dryness, crusting, scaling, inflammation, and discomfort of various skin conditions.
Test substances were each applied topically to the right ear of the test animal 30 minutes before and 15 minutes after Phorbol 12-Myristate 13-Acetate (PMA) was applied. The dosing volume was 20 μl/ear for solvent vehicle or 20 mg/ear for cream formulations.
Animals
Male CD-1 (Crl.) derived mice weighing 24±2 g were provided by BioLasco Taiwan (under Charles River Laboratories Technology Licensee). Space allocation for 10 animals was 29×18×13 cm. Mice were housed in APEC$^R$ cages. All animals were maintained in a controlled temperature (22° C.-23° C.) and humidity (70%-80%) environment with 12 hours light dark cycles for at least one week in MDS Pharma Services-Taiwan Laboratory prior to use. Free access to standard lab chow for mice (Lab Diet, Rodent Diet, PMI Nutrition International, USA) and tap water was granted. All aspects of this work including housing, experimentation and disposal of animals were performed in general accordance with the Guide for the Care and Use of Laboratory Animals (National Academy Press, Washington, D.C., 1996).
Chemicals
Acetone (Wako, Japan), Ethanol Absolute (Merck, Germany), Dexamethasone (Sigma, USA) and Phorbol 12-Myristate 13-Acetate (Sigma, USA).
Equipment
Animal Cage (Allentown, USA), Dyer model micrometer gauge (Peacock, Japan) and Pipetman (Gilson, France).
Inflammation Assay: Topical, Phorbol Ester
Groups of 5 CD-1 (Crl.) derived male mice weighing 24±2 g were used. PMA (4 pg in 20 μl of Acetone) was applied topically to the anterior and posterior surfaces of the right ear to each animal. Vehicle (Ethanol:Acetone/1:1, 20 μL/ear or cream, 20 mg/ear) and test substances including 5-(4-cyanophenoxy)-1-hydroxy-2,1-dihydrobenzoxaborole and betamethasone were each applied 30 minutes before and 15 minutes after PMA application. Dexamethasone (3 mg in 20 μL/ear of acetone:ethanol/1:1 3 mg/ear) as the positive control was similarly applied at the same timing. Ear swelling was then measured by a Dyer model micrometer gauge at 6 hours after PMA application as an index of inflammation. Percent inhibition was calculated according to the formula: ([Ic−It]/Ic)×100%, where Ic and It refer to increase of ear thickness (mm) in control and treated mice, respectively. Inhibition of 30 percent or more (>_30%) is considered significant anti-inflammatory activity.
Conclusion
In comparison with the respective vehicle (Ethanol:Acetone/1:1) or cream placebo control groups, 5-(4-cyanophenoxy)-1-hydroxy-2,1-benzoxaborole, (1 mg/ear×2), Betamethasone (0.2 mg/ear×2) and caused significant inhibition of the PMA-induced ear swelling.
Concurrently, dexamethasone (3 mg/ear) caused also a significant decrease (72%) in the ear swelling relative to the vehicle (Ethanol:Acetone/1:1)-treated group.
In conclusion, 5-(4-cyanophenoxy)-1-hydroxy-2,1-dihydrobenzoxaborole, at 1 mg/ear×2 and Betamethasone at 0.2 mg/ear×2 displayed significant (≧30% inhibition) anti-inflammatory activity, whereas 5-(4-cyanophenoxy)-1-hydroxy-2,1-dihydrobenzoxaborole, at 0.2 mg/ear×2 caused a moderate (22%) but non-significant inhibition of the ear swelling induced by topical phorbol ester in mice.

Example 20

Cyclic Boronic Esters
Additional compounds can be produced by the methods described herein. By choosing the appropriate starting material such as 1 or 3, the methods described herein can be used to formulate the following compounds. Where available, melting point characterization is provided for these compounds.

20. Results

Analytical data for exemplary compounds of structure I are provided below.

20a Ethyl 2-(1-hydroxy-1,3-dihydrobenzo[c][1,2]oxaborol-5-yloxy)acetate (C41)

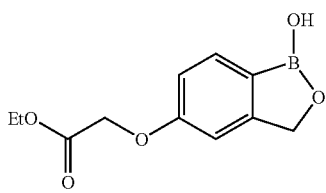

M.P. 134-137° C. Exemplary starting material: ethyl 2-(4-bromo-3-(hydroxymethyl)phenoxy)acetate.

20b 2-(1-hydroxy-1,3-dihydrobenzo[c][1,2]oxaborol-5-yloxy)acetic acid (C42)

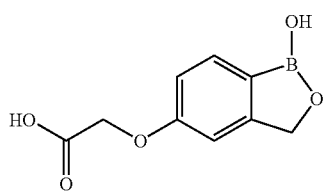

M.P. 163-166° C. Exemplary starting material: ethyl 2-(4-bromo-3-(hydroxymethyl)phenoxy)acetate. The title compound is obtained after saponification of the corresponding ester.

20c 6-(thiophen-2-ylthio)benzo[c][1,2]oxaborol-1(3H)-ol (C43)

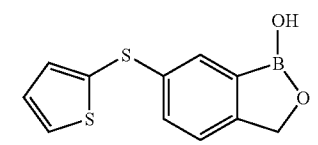

M.P. 99-104° C. Exemplary starting material: (2-bromo-4-(thiophen-2-ylthio)phenyl)methanol.

20d 6-(4-fluorophenylthio)benzo[c][1,2]oxaborol-1(3H)-ol (C44)

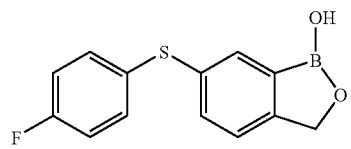

M.P. 135-138° C. Exemplary starting material: (2-bromo-4-(4-fluorophenylthio)phenyl)methanol.

20e 1-(3-((1-hydroxy-1,3-dihydrobenzo[c][1,2]oxaborol-5-yloxy)methyl)phenyl)pentan-1-one (C45)

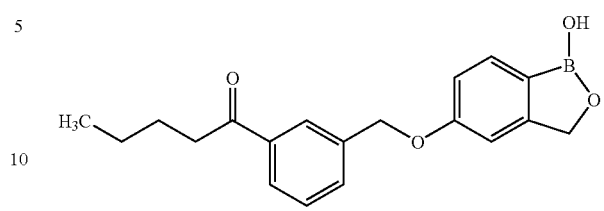

M.P. 96-98° C. Exemplary starting material: 1-(3-((4-bromo-3-(hydroxymethyl)phenoxy)methyl)phenyl)pentan-1-one.

20f 2-(1-hydroxy-1,3-dihydrobenzo[c][1,2]oxaborol-5-yloxy)-1-(piperidin-1-yl)ethanone (C46)

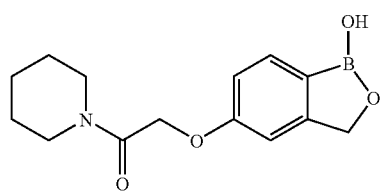

M.P. 158-163° C. Exemplary starting material: 2-(4-bromo-3-(hydroxymethyl)phenoxy)-1-(piperidin-1-yl)ethanone.

20g 2-(1-hydroxy-1,3-dihydrobenzo[c][1,2]oxaborol-5-yloxy)-1-(4-(pyrimidin-2-yl)piperazin-1-yl)ethanone (C47)

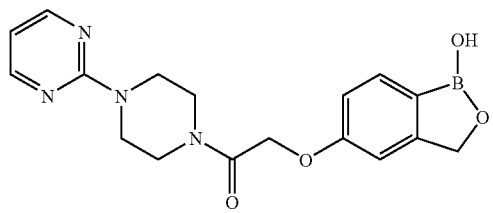

M.P. 190-195° C. Exemplary starting material: 2-(4-bromo-3-(hydroxymethyl)phenoxy)-1-(4-(pyrimidin-2-yl)piperazin-1-yl)ethanone.

20h 6-(4-(pyridin-2-yl)piperazin-1-yl)benzo[c][1,2]oxaborol-1(3H)-ol (C48)

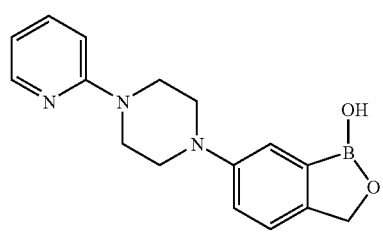

M.P. 135-138° C. Exemplary starting material: (2-bromo-4-(4-(pyridin-2-yl)piperazin-1-yl)phenyl)methanol.

20i 6-nitrobenzo[c][1,2]oxaborol-1(3H)-ol (C49)

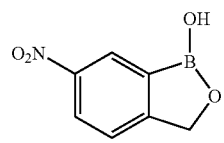

M.P. 163-171° C. Exemplary starting material: benzo[c][1,2]oxaborol-1(3H)-ol. See JACS 82, 2172, 1960 for preparation.

20j 6-aminobenzo[c][1,2]oxaborol-1(3H)-ol (C50)

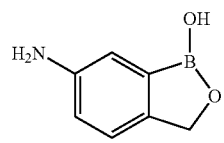

M.P. 145-148° C. Exemplary starting material: 6-nitrobenzo[c][1,2]oxaborol-1(3H)-ol.

20k 6-(dimethylamino)benzo[c][1,2]oxaborol-1(3H)-ol (C51)

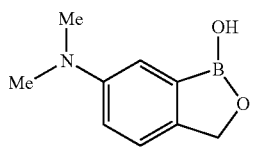

M.P. 120-123° C. Exemplary starting material: 6-aminobenzo[c][1,2]oxaborol-1(3H)-ol.

20l N-(1-hydroxy-1,3-dihydrobenzo[c][1,2]oxaborol-6-yl)benzamide (C52)

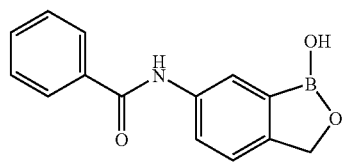

M.P. 186-193° C. Exemplary starting material: 6-aminobenzo[c][1,2]oxaborol-1(3H)-ol.

20m 6-(4-phenylpiperazin-1-yl)benzo[c][1,2]oxaborol-1(3H)-ol (C53)

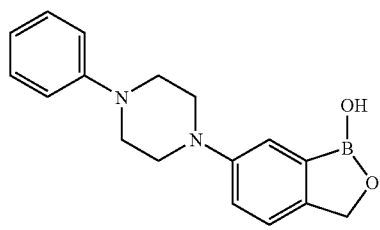

M.P. 159-161° C. Exemplary starting material: (2-bromo-4-(4-phenylpiperazin-1-yl)phenyl)methanol.

20n 6-(1H-indol-1-yl)benzo[c][1,2]oxaborol-1(3H)-ol (C55)

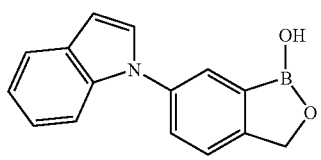

M.P. 135-140° C. Exemplary starting material: (2-bromo-4-(1H-indol-1-yl)phenyl)methanol.

20o 6-morpholinobenzo[c][1,2]oxaborol-1(3H)-ol (C56)

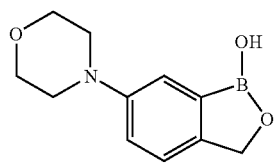

M.P. 128-132° C. Exemplary starting material: (2-bromo-4-morpholinophenyl)methanol.

20p 6-(1-hydroxy-1,3-dihydrobenzo[c][1,2]oxaborol-5-yloxy)nicotinonitrile (C57)

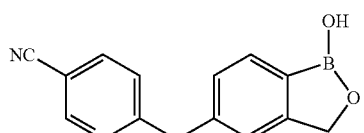

M.P. 193-198° C. Exemplary starting material: 6-(4-bromo-3-(hydroxymethyl)phenoxy)nicotinonitrile.

20q 5-fluoro-6-nitrobenzo[c][1,2]oxaborol-1(3H)-ol (C58)

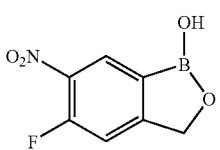

M.P. 162-167° C. Exemplary starting material: 5-fluorobenzo[c][1,2]oxaborol-1(3H)-ol.

20r 5-bromo-6-(hydroxymethyl)benzo[c][1,2]oxaborol-1(3H)-ol (C59)

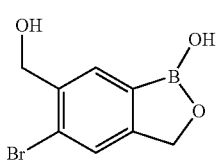

M.P.>257° C. Exemplary starting material: (2,5-dibromo-4-(methoxymethyl)phenyl)methanol.

20s 3,7-dihydro-1,5-dihydroxy-1H,3H-Benzo[1,2-c:4,5-c']bis[1,2]oxaborole (C60)

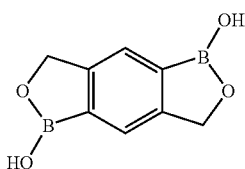

M.P.>250° C. Exemplary starting material: (2,5-dibromo-1,4-phenylene)dimethanol.

20t 1-(1-hydroxy-1,3-dihydrobenzo[c][1,2]oxaborol-6-yl)-3-phenylurea (C61)

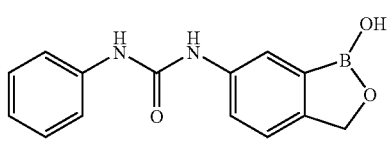

M.P. 213-215° C. Exemplary starting material: 6-aminobenzo[c][1,2]oxaborol-1(3H)-ol.

20u N-(1-hydroxy-1,3-dihydrobenzo[c][1,2]oxaborol-6-yl)benzenesulfonamide (C62)

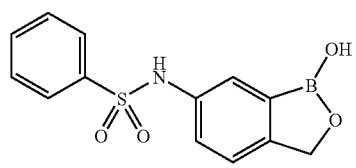

M.P. 175-184° C. Exemplary starting material: 6-aminobenzo[c][1,2]oxaborol-1(3H)-ol.

20v N-(1-hydroxy-1,3-dihydrobenzo[c][1,2]oxaborol-6-yl)acetamide (C63)

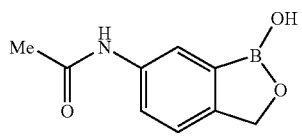

M.P. 176-185° C. Exemplary starting material: 6-aminobenzo[c][1,2]oxaborol-1(3H)-ol.

20w 7-(hydroxymethyl)benzo[c][1,2]oxaborol-1(3H)-ol (C64)

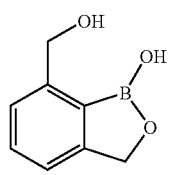

M.P. 241-250° C. Exemplary starting material: (2-bromo-1,3-phenylene)dimethanol.

20x 7-methylbenzo[c][1,2]oxaborol-1(3H)-ol (C65)

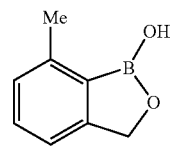

M.P. 107-111° C. Exemplary starting material: (2-bromo-3-methylphenyl)methanol.

20y 6-(3-(phenylthio)-1H-indol-1-yl)benzo[c][1,2]oxaborol-1(3H)-ol (C66)

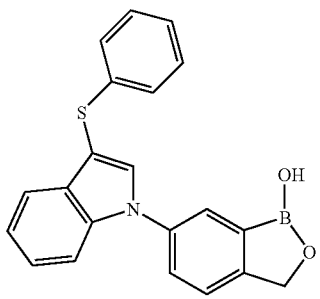

M.P. 159-163° C. Exemplary starting material: (2-bromo-4-(3-(phenylthio)-1H-indol-1-yl)phenyl)methanol.

20z 3-(1-(1-hydroxy-1,3-dihydrobenzo[c][1,2]oxaborol-6-yl)-1H-indol-3-ylthio)propanenitrile (C67)

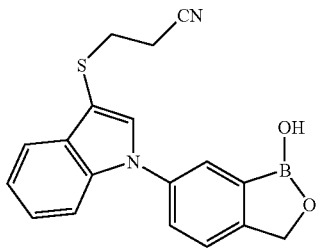

M.P. 135-141° C. Exemplary starting material: 3-(1-(3-bromo-4-(hydroxymethyl)phenyl)-1H-indol-3-ylthio)propanenitrile.

20aa 6-(5-methoxy-1H-indol-1-yl)benzo[c][1,2]oxaborol-1(3H)-ol (C68)

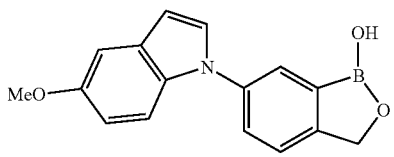

M.P. 120-124° C. Exemplary starting material: (2-bromo-4-(5-methoxy-1H-indol-1-yl)phenyl)methanol.

20bb 5,6-methylenedioxybenzo[c][1,2]oxaborol-1(3H)-ol. (C69)

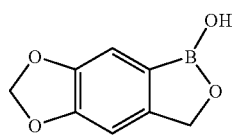

M.P. 185-189° C. Exemplary starting material: (6-bromobenzo[d][1,3]dioxol-5-yl)methanol.

20cc 6-amino-5-fluorobenzo[c][1,2]oxaborol-1(3H)-ol (C70)

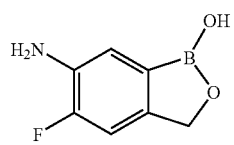

M.P. 142-145° C. Exemplary starting material: 6-nitro-5-fluorobenzo[c][1,2]oxaborol-1(3H)-ol.

20dd 6-(benzylamino)-5-fluorobenzo[c][1,2]oxaborol-1(3H)-ol (C71)

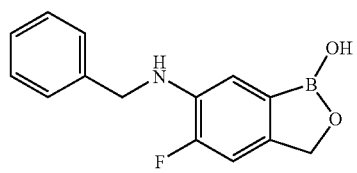

M.P. 159-164° C. Exemplary starting material: 6-amino-5-fluorobenzo[c][1,2]oxaborol-1(3H)-ol. pl 20ee 6-(5-methoxy-3-(phenylthio)-1H-indol-1-yl)benzo[c][1,2]oxaborol-1(3H)-ol (C72)

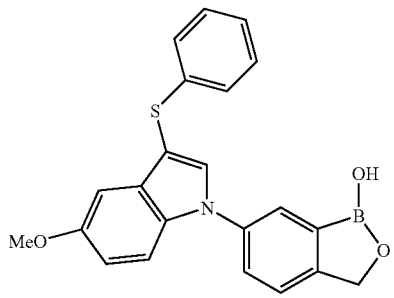

M.P. 135-141° C. Exemplary starting material: (2-bromo-4-(5-methoxy-3-(phenylthio)-1H-indol-1-yl)phenyl)methanol.

20ff 3-(1-(1-hydroxy-1,3-dihydrobenzo[c][1,2]oxaborol-6-yl)-5-methoxy-1H-indol-3-ylthio)propanenitrile (C73)

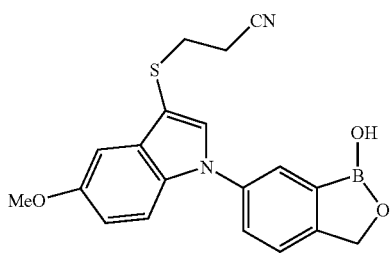

M.P. 149-154° C. Exemplary starting material: 3-(1-(3-bromo-4-(hydroxymethyl)phenyl)-5-methoxy-1H-indol-3-ylthio)propanenitrile.

20gg 4-(1-hydroxy-1,3-dihydrobenzo[c][1,2]oxaborol-7-yloxy)benzonitrile (C74)

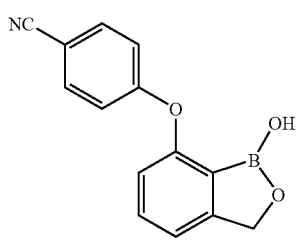

M.P. 148-153° C. Exemplary starting material: 4-(2-bromo-3-(hydroxymethyl)phenoxy)benzonitrile.

20hh 6-(5-chloro-1H-indol-1-yl)benzo[c][1,2]oxaborol-1(3H)-ol (C75)

M.P. 149-154° C. Exemplary starting material: (2-bromo-4-(5-chloro-1H-indol-1-yl)phenyl)methanol.

20ii 3-(5-chloro-1-(1-hydroxy-1,3-dihydrobenzo[c][1,2]oxaborol-6-yl)-1H-indol-3-ylthio)propanenitrile (C76)

M.P.>225° C. Exemplary starting material: 3-(1-(3-bromo-4-(hydroxymethyl)phenyl)-5-chloro-1H-indol-3-ylthio)propanenitrile.

20jj 6-(benzylamino)benzo[c][1,2]oxaborol-1(3H)-ol (C77)

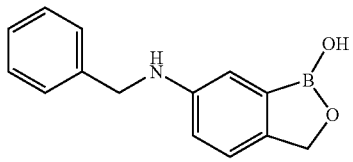

M.P. 126-133° C. Exemplary starting material: 6-aminobenzo[c][1,2]oxaborol-1(3H)-ol.

20kk 6-(dibenzylamino)benzo[c][1,2]oxaborol-1(3H)-ol (C78)

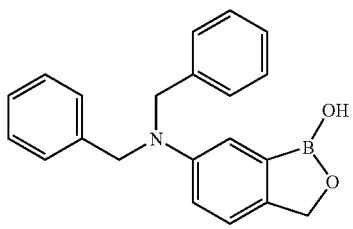

M.P. 115-123° C. Exemplary starting material: 6-aminobenzo[c][1,2]oxaborol-1(3H)-ol.

20ll 7-(4-(1H-tetrazol-5-yl)phenoxy)benzo[c][1,2]oxaborol-1(3H)-ol (C79)

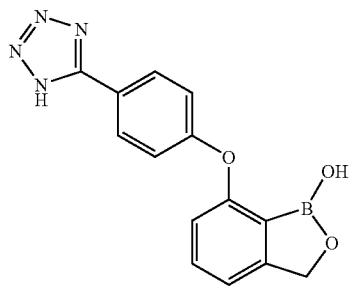

M.P. decomposition at 215° C. Exemplary starting material: 4-(1-hydroxy-1,3-dihydrobenzo[c][1,2]oxaborol-7-yloxy)benzonitrile.

20 mm 6-(5-chloro-3-(phenylthio)-1H-indol-1-yl)benzo[c][1,2]oxaborol-1(3H)-ol (C80)

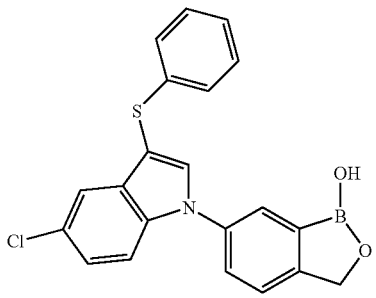

M.P. 145-151° C. Exemplary starting material: (2-bromo-4-(5-chloro-3-(phenylthio)-1H-indol-1-yl)phenyl)methanol.

20nn 6-(4-(pyrimidin-2-yl)piperazin-1-yl)benzo[c][1,2]oxaborol-1(3H)-ol (C82)

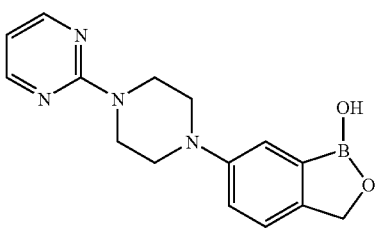

M.P. NA ° C. Exemplary starting material: (2-bromo-4-(4-(pyrimidin-2-yl)piperazin-1-yl)phenyl)methanol.

20oo 7-(benzyloxy)benzo[c][1,2]oxaborol-1(3H)-ol (C83)

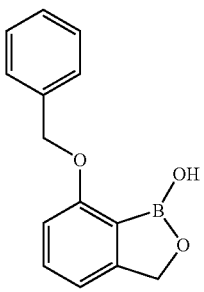

M.P. NA ° C. Exemplary starting material: (3-(benzyloxy)-2-bromophenyl)methanol.

20 pp 4-(1-hydroxy-1,3-dihydrobenzo[c][1,2]oxaborol-6-ylthio)pyridinium chloride (C84)

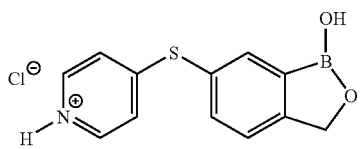

M.P. NA ° C. Exemplary starting material: (2-bromo-4-(pyridin-4-ylthio)phenyl)methanol.

20qq 6-(pyridin-2-ylthio)benzo[c][1,2]oxaborol-1(3H)-ol (C85)

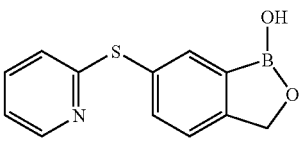

M.P. NA ° C. Exemplary starting material: (2-bromo-4-(pyridin-2-ylthio)phenyl)methanol.

20rr 7-fluorobenzo[c][1,2]oxaborol-1(3H)-ol (C86)

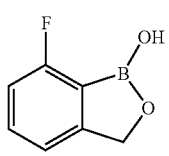

M.P. 120-124° C. Exemplary starting material: (2-bromo-3-fluorophenyl)methanol.

20ss 6-(4-(trifluoromethyl)phenoxy)benzo[c][1,2]oxaborol-1(3H)-ol (C87)

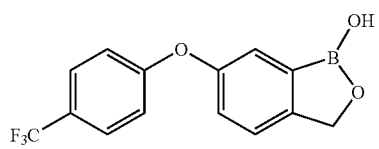

M.P. 98-105° C. Exemplary starting material: (2-bromo-4-(4-(trifluoromethyl)phenoxy)phenyl)methanol.

20tt 6-(4-chlorophenylthio)benzo[c][1,2]oxaborol-1(3H)-ol (C88)

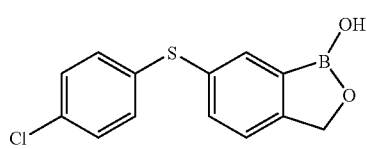

M.P. 157-161° C. Exemplary starting material: (2-bromo-4-(4-chlorophenylthio)phenyl)methanol.

20uu 6-(4-chlorophenylsulfinyl)benzo[c][1,2]oxaborol-1(3H)-ol (C89)

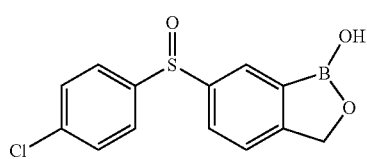

M.P. 154-161° C. Exemplary starting material: 6-(4-chlorophenylthio)benzo[c][1,2]oxaborol-1(3H)-ol.

20vv 6-(4-chlorophenylsulfonyl)benzo[c][1,2]oxaborol-1(3H)-ol (C90)

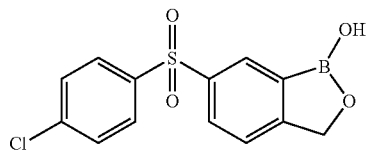

M.P. 157-163° C. Exemplary starting material: 6-(4-chlorophenylthio)benzo[c][1,2]oxaborol-1(3H)-ol.

20ww N-(1-hydroxy-1,3-dihydrobenzo[c][1,2]oxaborol-5-yl)-N-(phenylsulfonyl)benzenesulfonamide (C91)

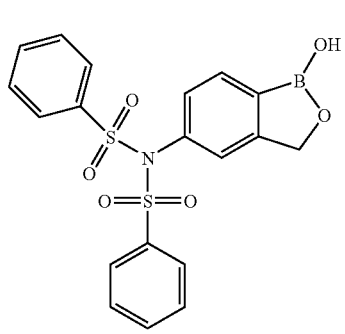

M.P. 142-152° C. Exemplary starting material: N-(4-bromo-3-(hydroxymethyl)phenyl)-N-(phenylsulfonyl)benzenesulfonamide.

20xx 6-(4-(trifluoromethyl)phenylthio)benzo[c][1,2]oxaborol-1(3H)-ol (C92)

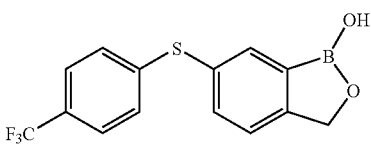

M.P. 111-113° C. Exemplary starting material: (2-bromo-4-(4-(trifluoromethyl)phenylthio)phenyl)methanol.

20yy 6-(4-(trifluoromethyl)phenylsulfinyl)benzo[c][1,2]oxaborol-1(3H)-ol (C93)

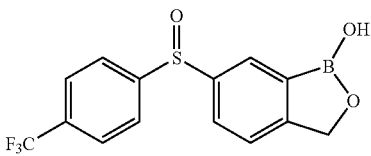

M.P. 79-88° C. Exemplary starting material: 6-(4-(trifluoromethyl)phenylthio)benzo[c][1,2]oxaborol-1(3H)-ol.

20zz 6-(4-(methylthio)phenylthio)benzo[c][1,2]oxaborol-1(3H)-ol (C94)

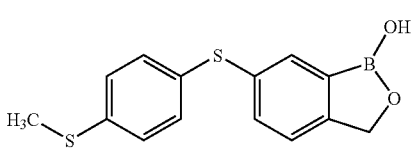

M.P. 117-120° C. Exemplary starting material: (2-bromo-4-(4-(methylthio)phenylthio)phenyl)methanol.

20aaa 6-(p-tolylthio)benzo[c][1,2]oxaborol-1(3H)-ol (C95)

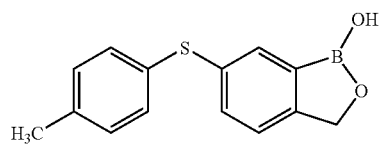

M.P. 139-144° C. Exemplary starting material: (2-bromo-4-(p-tolylthio)phenyl)methanol.

20bbb 3-((1-hydroxy-1,3-dihydrobenzo[c][1,2]oxaborol-5-yloxy)methyl)benzonitrile (C96)

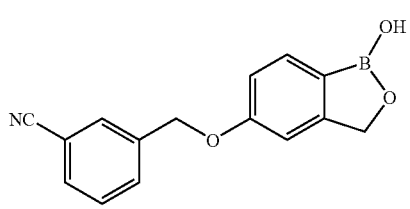

M.P. 147-150° C. Exemplary starting material: 3-((4-bromo-3-(hydroxymethyl)phenoxy)methyl)benzonitrile.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating an inflammatory-related disease in a human or an animal, said method comprising administering to the human or the animal a therapeutically effective amount of a compound which is selected from the group consisting of

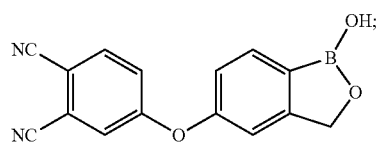

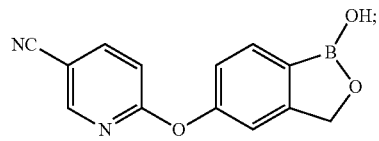

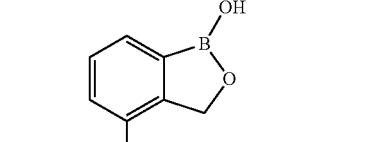

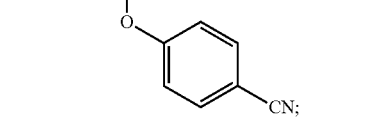

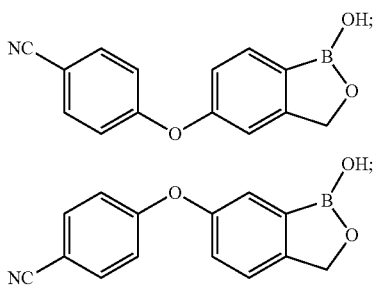

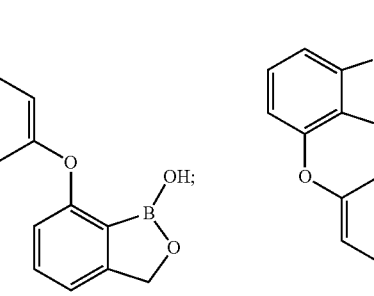

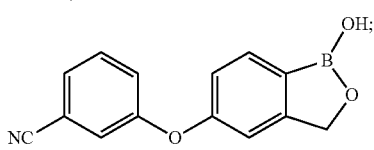

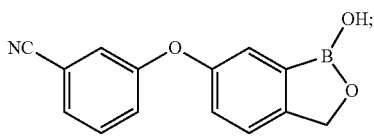

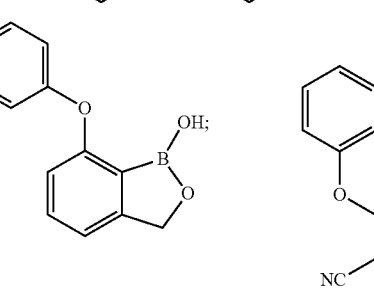

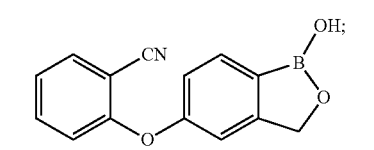

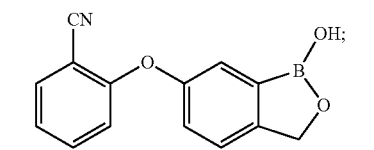

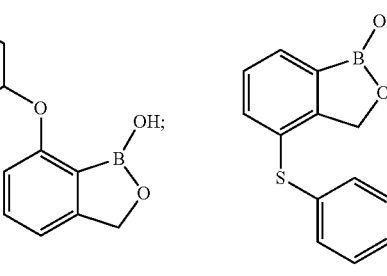

-continued

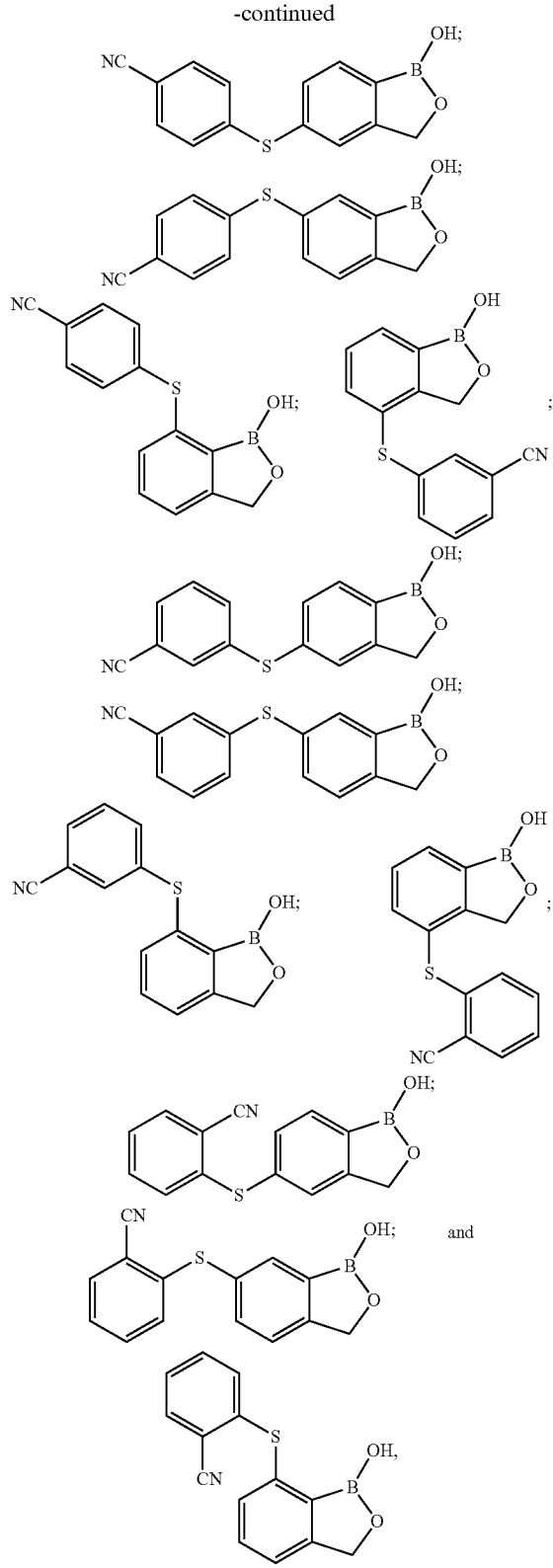

or a pharmaceutically acceptable salt thereof.

2. The method of claim 1, further comprising administering said compound as part of a pharmaceutical formulation, said formulation further comprising a pharmaceutically acceptable excipient.

3. The method of claim 1, wherein said compound is present in a form which is a member selected from a hydrate with water, a solvate with an alcohol, an adduct with an amino compound, and an adduct with an acid.

4. The method of claim 1, wherein said compound has a structure which is selected from the group consisting of

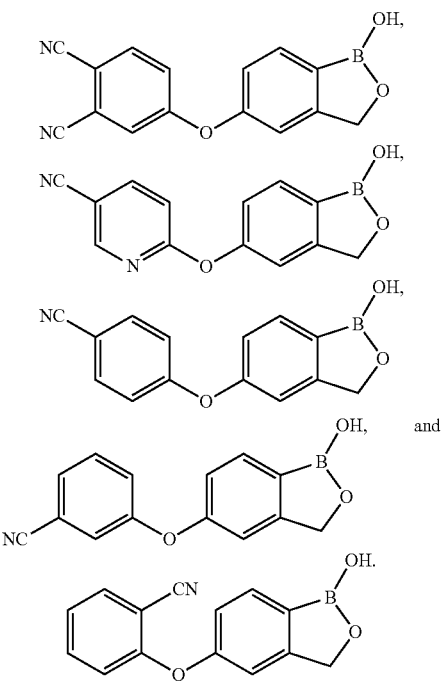

5. The method of claim 1, wherein the compound is in an amount sufficient to treat the inflammatory-related disease by inhibiting pro-inflammatory cytokine expression or by stimulating anti-inflammatory cytokine expression, but the amount is less than sufficient to substantially inhibit cyclin dependent kinases.

6. The method of claim 5, wherein the compound has a structure which is selected from the group consisting of

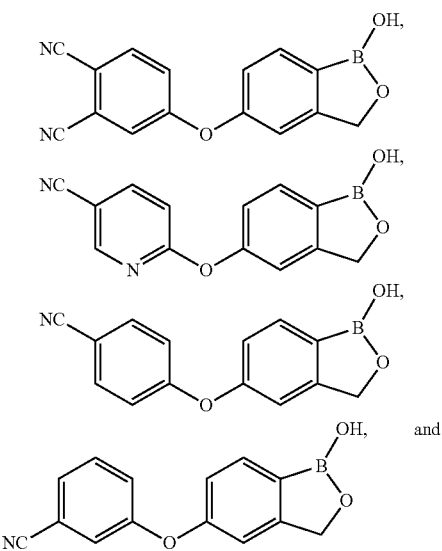

-continued

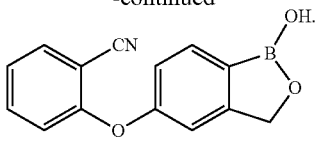

7. The method of claim 1, wherein the disease is a member selected from arthritis, rheumatoid arthritis, an inflammatory bowel disease, psoriasis, multiple sclerosis, a neurodegenerative disorder, congestive heart failure, stroke, aortic valve stenosis, kidney failure, lupus, pancreatitis, allergy, fibrosis, anemia, atherosclerosis, a metabolic disease, a bone disease, a cardiovascular disease, a chemotherapy/radiation related complication, diabetes type I, diabetes type II, a liver disease, a gastrointestinal disorder, an ophthalmological disease, allergic conjunctivitis, diabetic retinopathy, Sjogren's syndrome, uveitis, a pulmonary disorder, a renal disease, dermatitis, HIV-related cachexia, cerebral malaria, ankylosing spondylitis, leprosy, anemia and fibromyalgia.

8. The method of claim 7, wherein the compound has a structure which is selected from the group consisting of

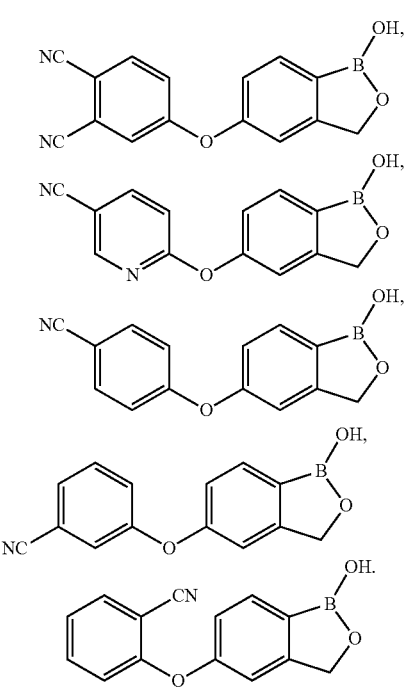

9. The method of claim 7, wherein the neurodegenerative disorder is a member selected from Alzheimer's disease and Parkinson disease, the inflammatory bowel disease is a member selected from Crohn's disease or ulcerative colitis; the gastrointestinal complication is diarrhea; the liver disease is a member selected from an autoimmune hepatitis, hepatitis C, primary biliary cirrhosis, primary sclerosing cholangitis and fulminant liver failure; the gastrointestinal disorder is a member selected from celiac disease and non-specific colitis; the pulmonary disorder is a member selected from allergic rhinitis, asthma, chronic obstructive pulmonary disease, chronic granulomatous inflammation, cystic fibrosis, and sarcoidosis; the cardiovascular disease is a member selected from atheroscleotic cardiac disease, congestive heart failure and restenosis; and the renal disease is a member selected from glomerulonephritis and vasculitis.

10. The method of claim 9, wherein the compound has a structure which is selected from the group consisting of

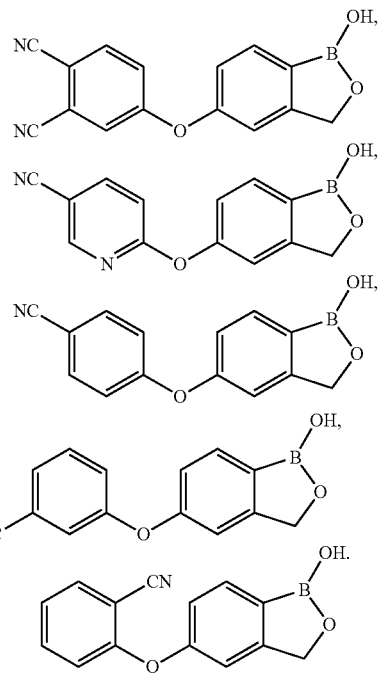

11. The method of claim 1, wherein the compound is administered at a concentration sufficient to inhibit a cytokine which is a member selected from IL-1α, β, IL-2, IL-3, IL-6, IL-7, IL-9, IL-12, IL-17, IL-18, IL-23, TNF-α, LT, LIF, Oncostatin, and IFNc1α, β, γ.

12. The method of claim 11, wherein the compound has a structure which is selected from the group consisting of

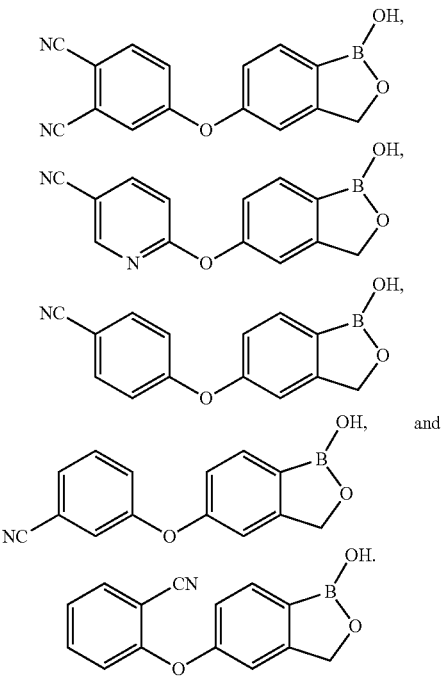

13. The method of claim 1, where the compound is administered at a concentration sufficient to stimulate expression of a cytokine which is a member selected from IL-4, IL-10, IL-11, W-13 and TGF-β.

14. The method of claim 13, wherein the compound has a structure which is selected from the group consisting of

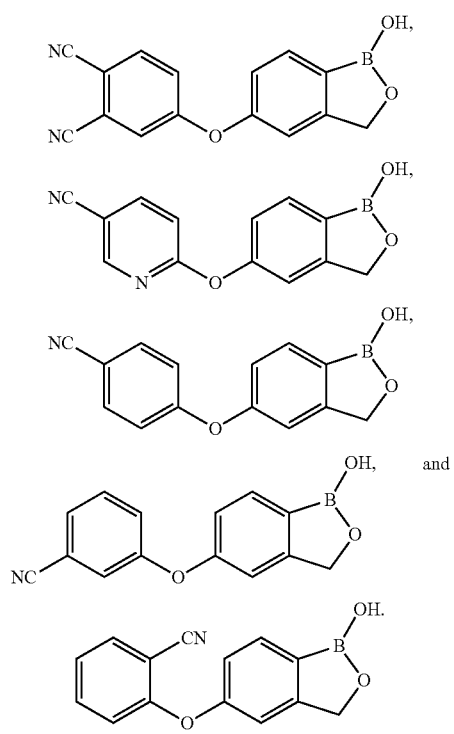

15. A method of treating an inflammatory-related disease associated with cytokine expression levels, which comprises administering to a human or an animal in need of such treatment a compound which is selected from the group consisting of

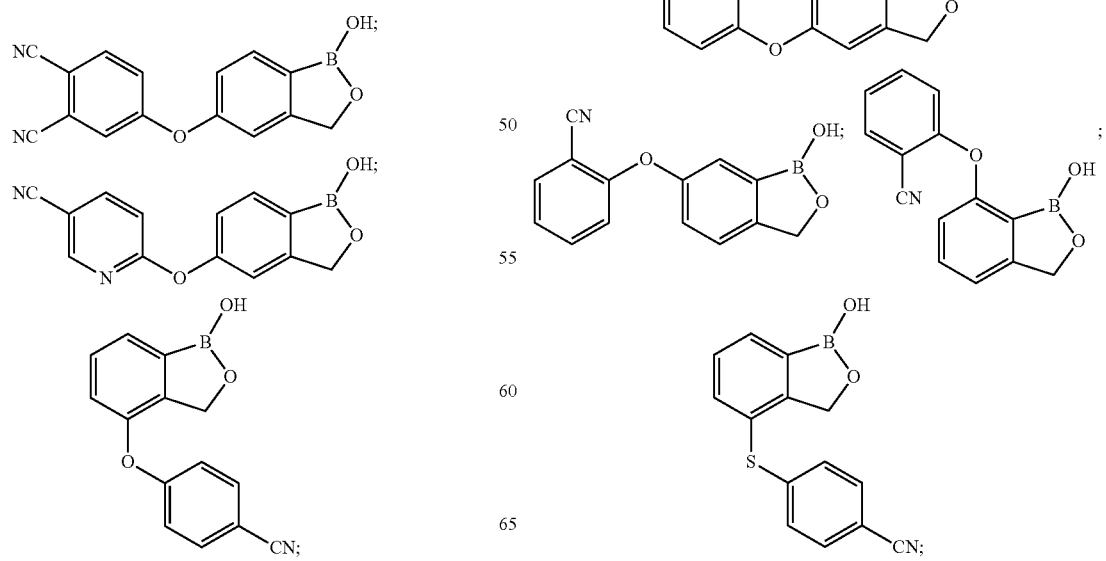

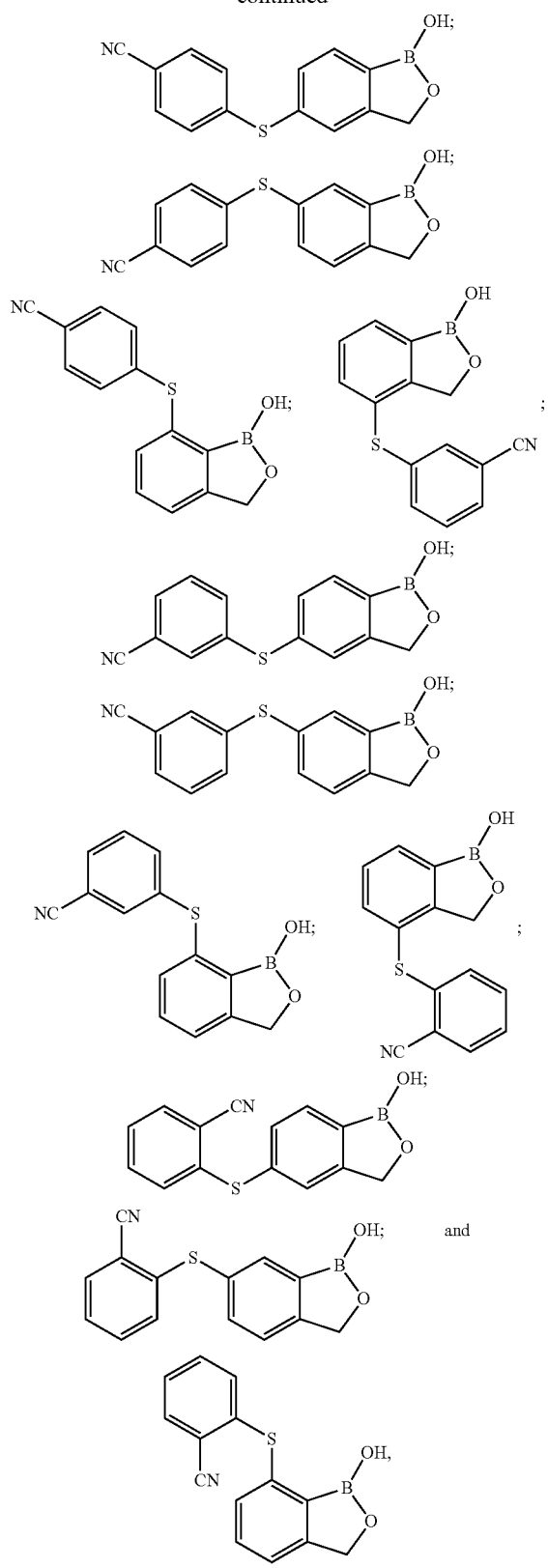

or a pharmaceutically acceptable salt thereof.

16. The method of claim 15, wherein the compound has a structure which is selected from the group consisting of

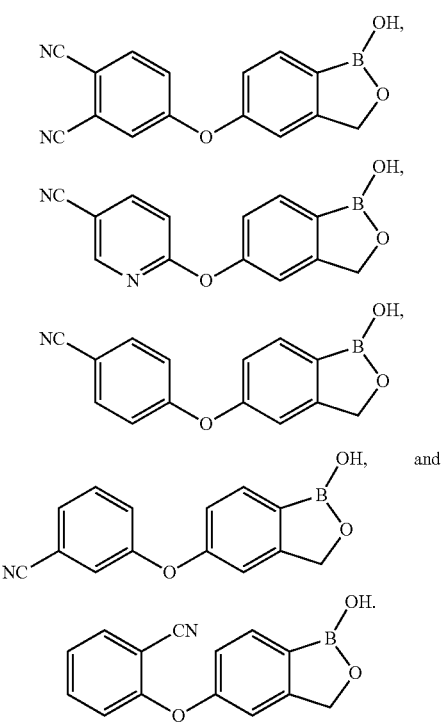

17. The method of claim 1, wherein the animal is a human being.

18. A method for inhibiting the production of an inflammatory cytokine protein by cells capable of producing said inflammatory cytokine protein, said method comprising: combining said cells with a therapeutic amount of, a compound which is selected from the group consisting of -continued
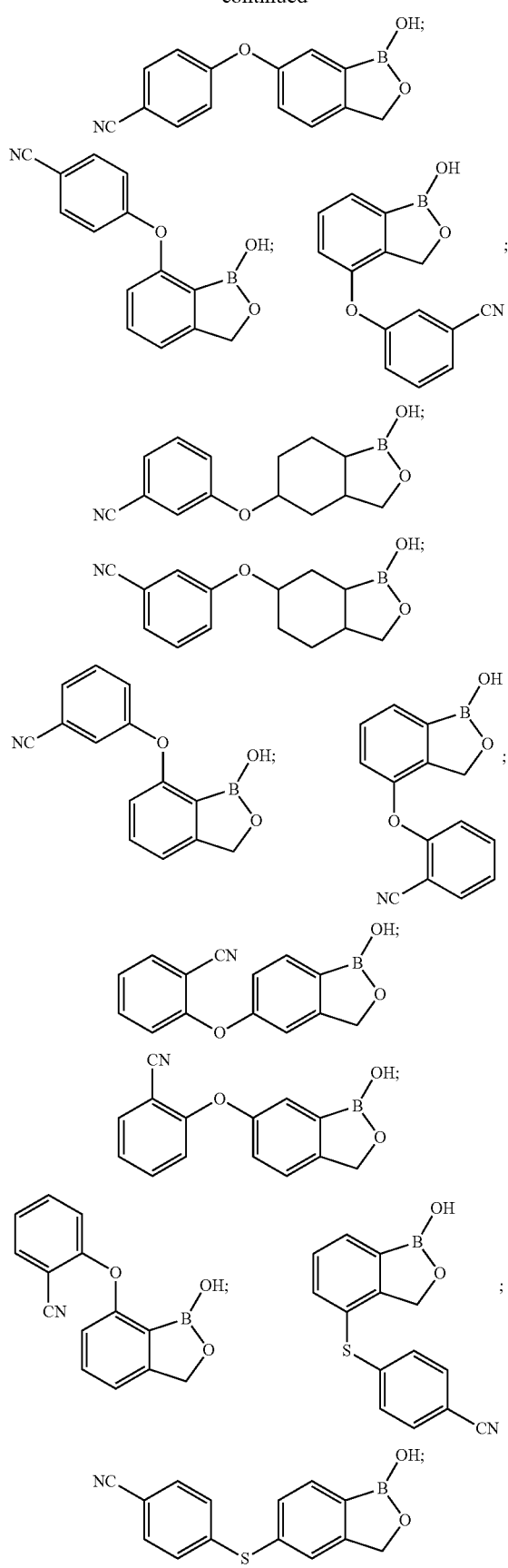
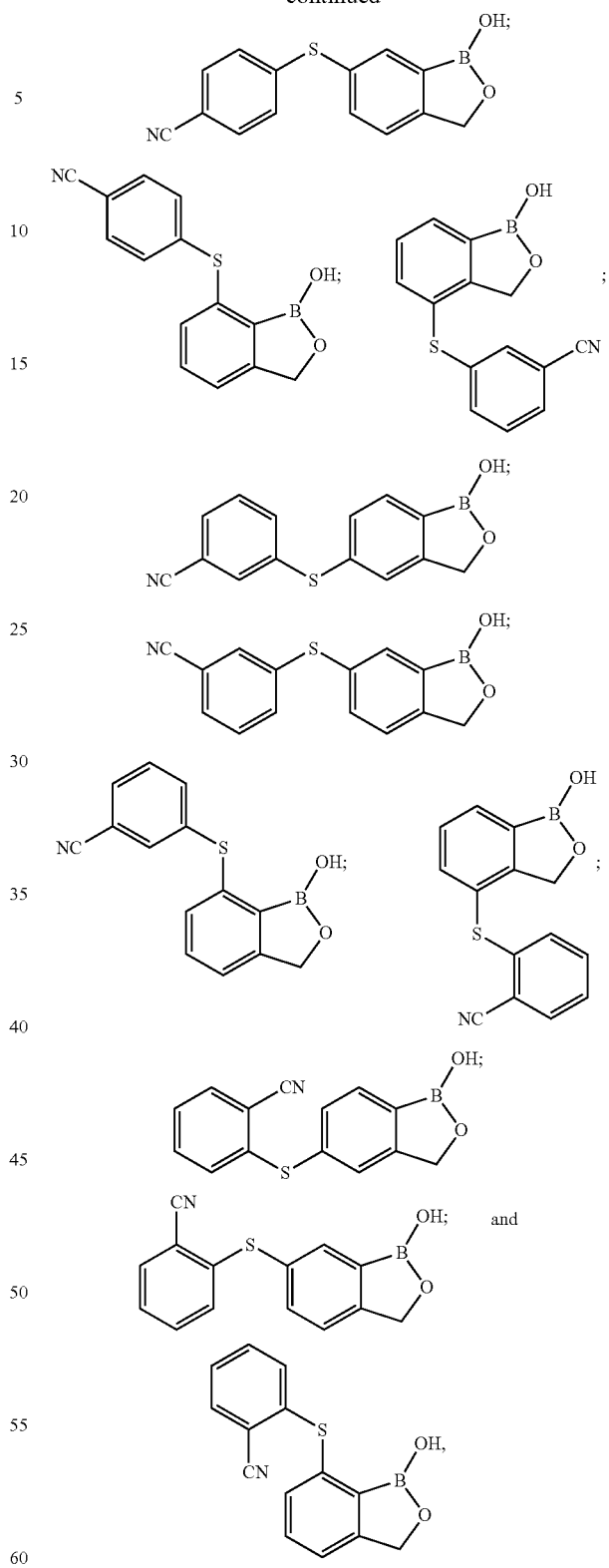
or a pharmaceutically acceptable salt thereof, wherein production of said inflammatory cytokine by said cells is inhibited.
19. The method of claim 18, wherein the compound has a structure which is selected from the group consisting of

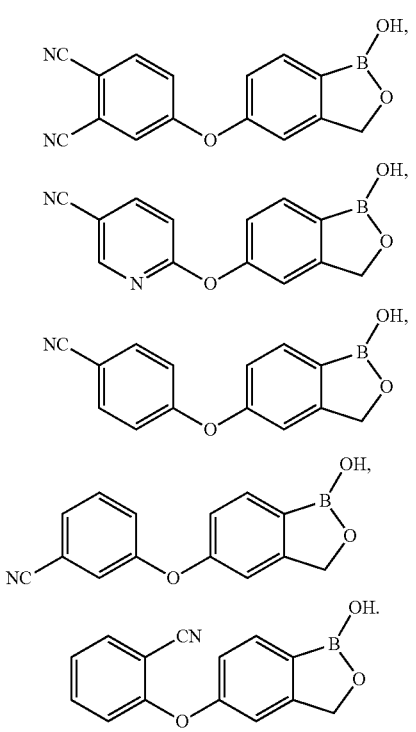

20. The method of claim 18, wherein said therapeutic amount is sufficient to inhibit the production of said inflammatory cytokine protein between about 50% and about 99%.

21. A method for inhibiting an inflammatory response in a human or an animal, said method comprising: contacting said human or animal with a therapeutic amount of a compound which is selected from the group consisting of

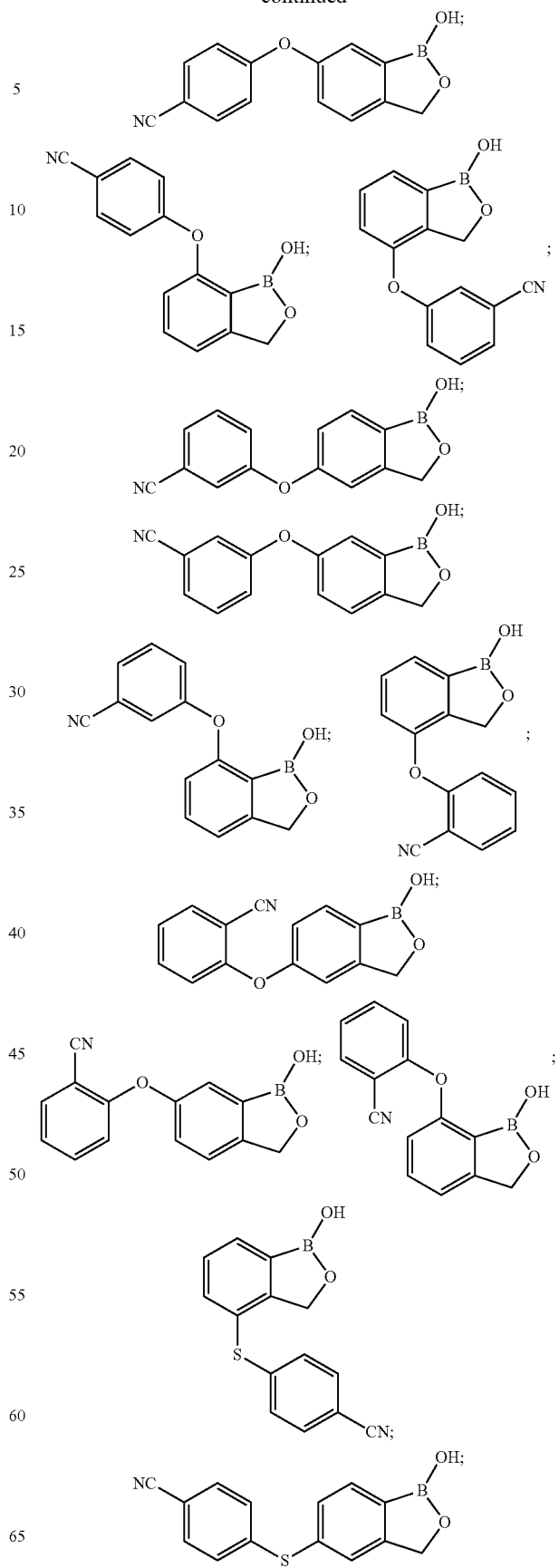

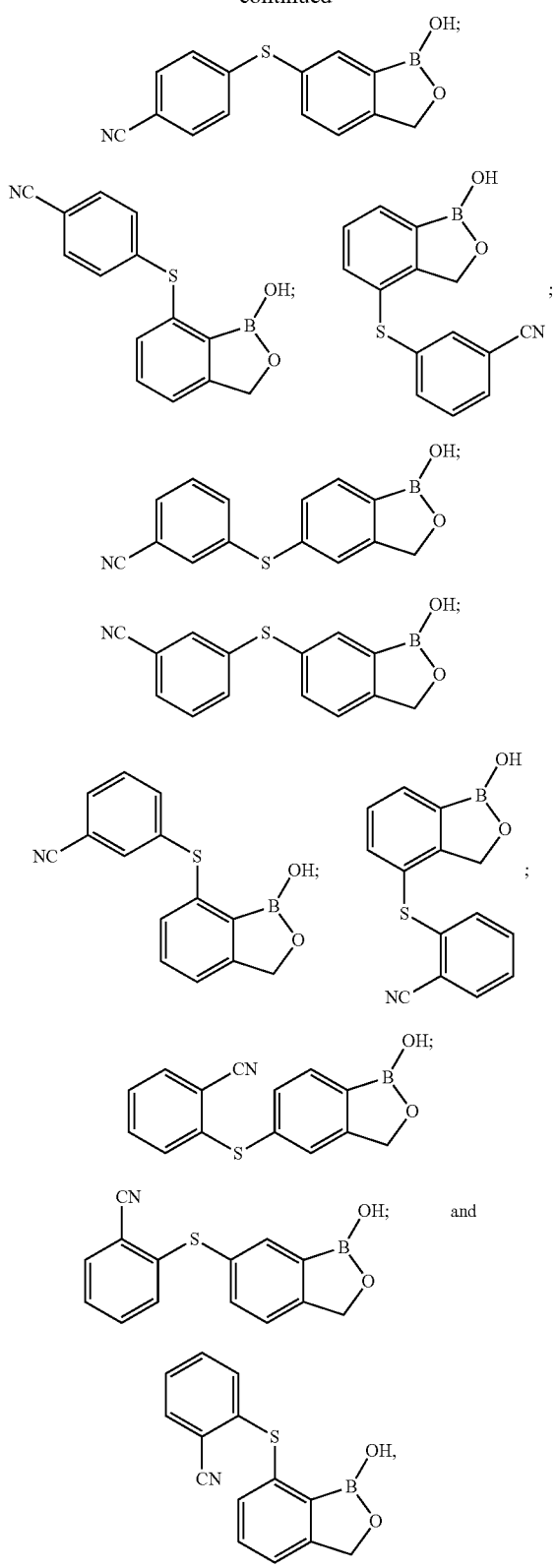
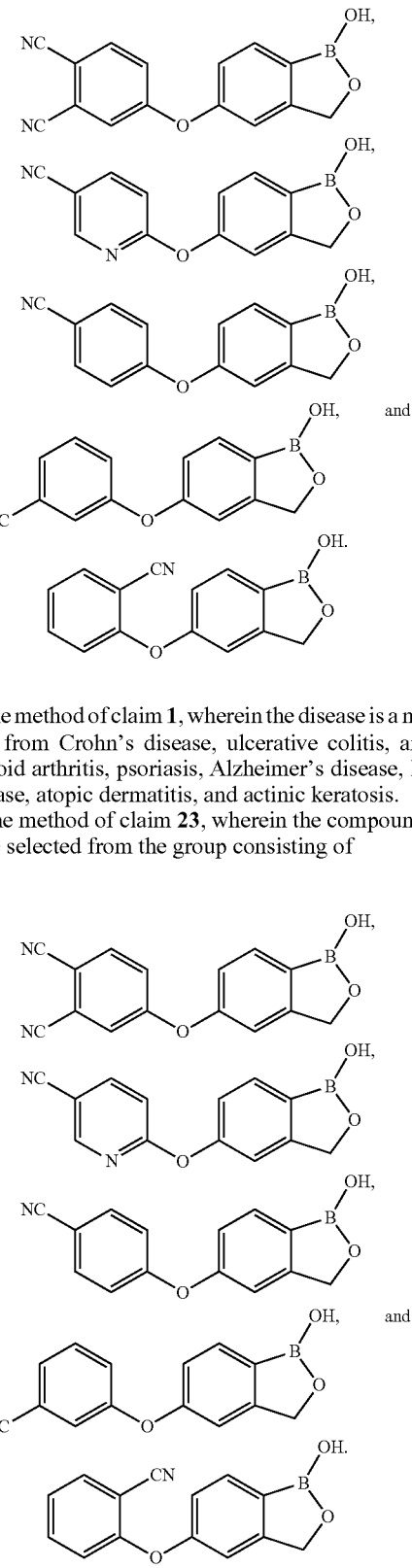

or a pharmaceutically acceptable salt thereof, wherein said inflammatory response is inhibited.

22. The method of claim 21, wherein the compound has a structure which is selected from the group consisting of 23. The method of claim 1, wherein the disease is a member selected from Crohn's disease, ulcerative colitis, arthritis, rheumatoid arthritis, psoriasis, Alzheimer's disease, Parkinson disease, atopic dermatitis, and actinic keratosis.

24. The method of claim 23, wherein the compound has a structure selected from the group consisting of 25. A method of treating an inflammatory-related disease in a human or an animal, said method comprising administering to the human or the animal a therapeutically effective amount of a compound having the following structure

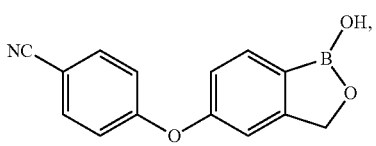

or a pharmaceutically acceptable salt thereof.

26. A method of treating an inflammatory-related disease in a human or an animal, said method comprising administering to the human or the animal a therapeutically effective amount of a compound having the following structure

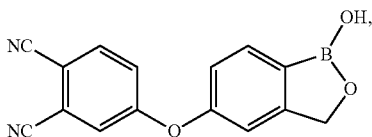

or a pharmaceutically acceptable salt thereof.

27. A method of treating psoriasis, comprising administering to the human or the animal a therapeutically effective amount of a compound having the following structure

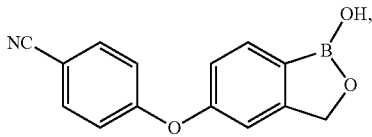

or a pharmaceutically acceptable salt thereof.

28. A method of treating psoriasis, comprising administering to the human or the animal a therapeutically effective amount of a compound having the following structure

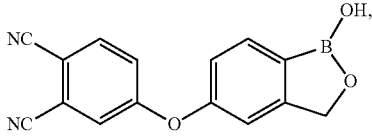

or a pharmaceutically acceptable salt thereof.

29. A method of treating atopic dermatitis, comprising administering to the human or the animal a therapeutically effective amount of a compound having the following structure

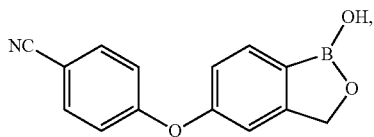

or a pharmaceutically acceptable salt thereof.

30. A method of treating atopic dermatitis, comprising administering to the human or the animal a therapeutically effective amount of a compound having the following structure

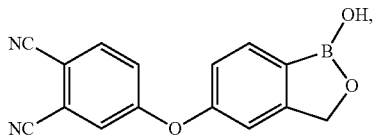

or a pharmaceutically acceptable salt thereof.

31. The method of claim 25, wherein the inflammatory-related disease is dermatitis or eczema.

32. The method of claim 25, wherein the inflammatory-related disease is contact dermatitis.

33. The method of claim 25, wherein the inflammatory-related disease is rheumatoid arthritis or psoriatic arthritis.

34. The method of claim 26, wherein the inflammatory-related disease is dermatitis or eczema.

35. The method of claim 26, wherein the inflammatory-related disease is contact dermatitis.

36. The method of claim 26, wherein the inflammatory-related disease is rheumatoid arthritis or psoriatic arthritis.

* * * * *